United States Patent
Scalese et al.

(10) Patent No.: US 6,247,246 B1
(45) Date of Patent: Jun. 19, 2001

(54) MICROWAVE MOISTURE ANALYZER: APPARATUS AND METHOD

(75) Inventors: Robert F. Scalese, Superior; Thomas B. Taylor, Golden; Tim Holzschuh, Littleton; Douglas E. Harbert, Denver; Thomas G. Playen, Littleton; Martin L. Maple, Aurora, all of CO (US); Jan Claesson, Granger, IN (US)

(73) Assignee: Denver Instrument Company, Arvada, CO (US)

( * ) Notice: Subject to any disclaimer, the term of this patent is extended or adjusted under 35 U.S.C. 154(b) by 0 days.

(21) Appl. No.: 09/086,756

(22) Filed: May 27, 1998

(51) Int. Cl.⁷ ........................................ F26B 3/34

(52) U.S. Cl. ................... 34/259; 34/265; 34/549; 34/574; 34/202; 219/678; 219/702; 219/704; 219/707; 219/708; 219/709

(58) Field of Search ................... 219/678, 690, 219/695, 696, 702, 704, 707, 708, 709; 34/245, 259, 265, 524, 549, 573, 574, 201, 202

(56) References Cited

U.S. PATENT DOCUMENTS

| | | |
|---|---|---|
| Re. 32,861 | 2/1989 | Collins et al. . |
| Re. 34,373 | 9/1993 | Collins et al. . |
| 3,652,940 | 3/1972 | Reiter et al. . |

(List continued on next page.)

FOREIGN PATENT DOCUMENTS

| | | |
|---|---|---|
| 44-23956 | 10/1969 | (JP) . |
| 3-172746 | 7/1991 | (JP) . |

OTHER PUBLICATIONS

Frank Reggia, Magnetically Tunable Microwave Bandpass Filter, Jan. 1963, pp. 72 through 74, The Microwave Journal.

H.G. Wiedemann, Universal Measuring Instrument for Gravimetric Investigations Under Variable Conditions 1964, Mettler Instrument Corporation.

Okress, Ernest C., Microwave Power Engineering, 1968, pp. 49–53, 63, 156 and 195, vol. 2, Academic Press, New York and London.

Leonhardt, G.F., et al., Microwave Drying of Microorganisms. II. The Use of Microwave Oven for the Determination of Moisture Content of Pressed Yeast, Journal of Microwave Power, 1978, 4 pages total, vol. 13(3), IMPI, Canada.

Risman, P.O., A Microwave Applicator for Drying Food Samples, Journal of Microwave Power, 1978, cover page, pp. 298–301, vol. 13 (4), IMPI, Canada.

Primary Examiner—Pamela Wilson
(74) Attorney, Agent, or Firm—Bernhard Kreten

(57) ABSTRACT

A toploading weighing instrumentality which determines loss on drying by a cylindrical microwave. The cylindrical cavity of the microwave includes a power supply, a magnetron, a power module operatively coupled between said power supply and said magnetron for driving said magnetron, a wave guide communicating with the magnetron and with a microwave containment chamber for delivering energy thereto, at least one microwave energy sensor for sensing microwave energy or magnetic and/or electric field strength within the chamber for controlling, inter alia, the loss on drying process of the sample being assayed and determining when the drying process is complete. A precision electronic balance is operatively disposed within the microwave chamber for allowing a specimen being assayed to be weighed. In addition, a ventilation chamber is provided for venting moisture from the microwave chamber. A processing unit and associated memory allows means for data acquisition, processing and storage of data from the power module driving the magnetron, the microwave energy sensor (s) for sensing magnetic and/or electric fields and the electronic balance for weighing the initial and final weights of the specimen for loss on drying moisture analysis. Both signaling the removal of microwave energy in the chamber.

44 Claims, 35 Drawing Sheets

U.S. PATENT DOCUMENTS

| | | |
|---|---|---|
| 3,680,012 | 7/1972 | Moreau . |
| 3,748,605 | 7/1973 | Baynham et al. . |
| 3,758,737 | 9/1973 | Ironfield . |
| 3,869,681 | 3/1975 | Klein et al. . |
| 3,890,825 | 6/1975 | Davis . |
| 3,909,598 | 9/1975 | Collins et al. . |
| 3,916,670 | 11/1975 | Davis et al. . |
| 4,037,182 | 7/1977 | Burnett et al. . |
| 4,106,329 | 8/1978 | Takahashi et al. . |
| 4,127,834 | 11/1978 | Stringfellow et al. . |
| 4,165,633 | 8/1979 | Raisanen . |
| 4,168,623 | 9/1979 | Thomas, Jr. . |
| 4,193,116 | 3/1980 | Funk . |
| 4,276,462 | 6/1981 | Risman . |
| 4,291,775 | 9/1981 | Collins . |
| 4,312,218 | 1/1982 | Eckles . |
| 4,316,384 | 2/1982 | Pommer et al. . |
| 4,390,768 | 6/1983 | Teich et al. . |
| 4,398,835 | 8/1983 | Athey et al. . |
| 4,413,168 | 11/1983 | Teich . |
| 4,438,500 | 3/1984 | Collins et al. . |
| 4,457,632 | 7/1984 | Collins et al. . |
| 4,485,284 | 11/1984 | Pakulis . |
| 4,521,746 | 6/1985 | Hwan et al. . |
| 4,554,132 | 11/1985 | Collins . |
| 4,565,669 | 1/1986 | Collins et al. . |
| 4,566,312 | 1/1986 | Collins et al. . |
| 4,566,804 | 1/1986 | Collins et al. . |
| 4,620,146 | 10/1986 | Ishikawa et al. . |
| 4,651,285 | 3/1987 | Collins et al. . |
| 4,681,996 | 7/1987 | Collins et al. . |
| 4,749,054 | 6/1988 | Virtanen et al. . |
| 4,750,143 | 6/1988 | Heitz et al. . |
| 4,753,889 | 6/1988 | Collins . |
| 4,835,354 | 5/1989 | Collins et al. . |
| 4,838,705 | 6/1989 | Byers, Jr. et al. . |
| 4,851,630 | 7/1989 | Smith . |
| 4,861,556 | 8/1989 | Neas et al. . |
| 4,882,286 | 11/1989 | Neas et al. . |
| 4,939,489 | 7/1990 | Gueble et al. . |
| 4,946,797 | 8/1990 | Neas et al. . |
| 5,085,527 | 2/1992 | Gilbert . |
| 5,176,146 | 1/1993 | Maurice et al. ..................... 128/736 |
| 5,211,252 | 5/1993 | Henderson et al. . |
| 5,215,715 | 6/1993 | Haswell et al. . |
| 5,216,388 | 6/1993 | Dipoala . |
| 5,256,978 | 10/1993 | Rose . |
| 5,293,019 * | 3/1994 | Lee ....................................... 219/708 |
| 5,318,754 | 6/1994 | Collins et al. . |
| 5,329,255 | 7/1994 | Hayes et al. . |
| 5,397,993 | 3/1995 | Tews et al. . |
| 5,420,039 | 5/1995 | Renoe et al. . |
| 5,632,921 | 5/1997 | Risman et al. . |
| 5,653,906 * | 8/1997 | Fowler et al. ....................... 219/716 |

\* cited by examiner

| Fig. 21A | Fig. 21C |
|---|---|
| Fig. 21B | Fig. 21D |

A/D CONVERTER

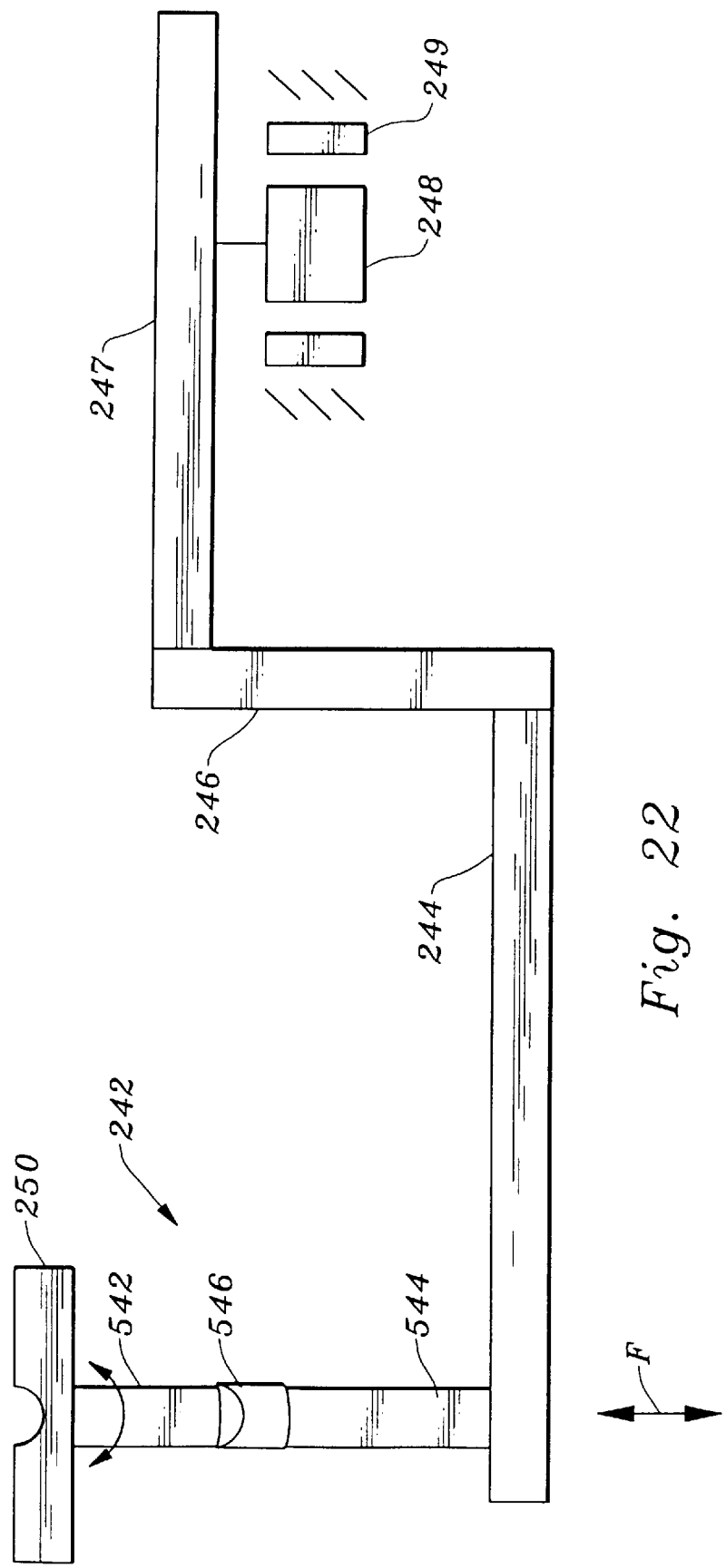

MICROWAVE MOISTURE ANALYZER: APPARATUS AND METHOD

FIELD OF THE INVENTION

The instant invention relates generally to a moisture analyzer and, in particular, to a microwave moisture analyzer for loss on drying applications.

BACKGROUND OF THE INVENTION

A multiplicity of devices and analytical methods have been developed in an attempt to obtain fast and accurate quantitative analysis of a vast array of products which are manufactured subject to strict control of moisture. For example, certain products have a specific range of moisture which dictates the taste and/or texture of the product. Thus, once the consumer associates a specific taste and/or texture to the product the uniformity of that taste and/or texture becomes a hallmark to the product's long term acceptance and ultimate success. Furthermore, moisture content is a specific process control in food processing, waste water treatment and materials processing.

Typically, these products require the volatilization of moisture or the like from the substance for moisture determination. In recent years, conventional microwave heating has been employed in the methods to remove various volatiles such as moisture followed by calculations of the amount of moisture lost. Conventional microwave heating requires the use of high power levels for providing effective drying due to the conventional microwave oven's employing random direction $T_e$ waves as the dominant energy field for the drying process. As a result, these microwave ovens produce hot and cold spots, over heating edges and charring of the products being analyzed. In addition, these conventional microwave ovens failed to provide a satisfactory solution which provided fast and accurate moisture determination of the product without the degradation of the product due to these problems.

Thus, there continues to be a need for an efficient microwave moisture analyzer which offers uniformity of microwave heating and rapid moisture determining analysis without the degradation of the product due to these problems. This is particularly important in light of the fact that most of the testing of products is related to process control in some form or another. Thus, the speed of the analysis and tests are hallmarks of high quality mass production. In addition, there is a need for a microwave moisture analyzer which provides timely feedback for maintaining tight tolerances of both the process and product produced thereby. Furthermore, a microwave moisture analyzer is needed which includes automated functions which simplify routine analysis thereby substantially eliminating the dependency of the result of the analysis on the skill and care exercised by the operator.

In addition, scales have been employed within these conventional microwave ovens to measure the weight of the product being analyzed. However, these devices have heretofore been susceptible to jarring and vibration in the working environment which resulted in anomalous weight readings. Such inconsistencies in operation result in unpredictable and unreliable moisture determination of the product.

Furthermore, none of the prior art which applicant is aware addresses the problem of continuing to dry the product after all of the moisture has been exhausted therefrom. This of course alters the mass which introduces an error in the final moisture calculation. Moreover, none of the prior art which applicant is aware addresses the possibility of a sample igniting in the chamber while doing a loss on drying process. Although the possibility of a sample igniting in the chamber while doing a loss on drying process is low, it does exist.

Therefore, not only does there continue to be a need for an efficient microwave moisture analyzer which offers uniformity of microwave heating and timely feedback for maintaining tight tolerances of the drying process, there also continues to be a need for a microwave moisture analyzer which is impervious to vibration and jarring and which addresses the problem of over drying the product and the possibility of the product igniting in the analyzer.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 3,909,598 | September 30, 1975 | Collins, et al. |
| 4,106,329 | August 15, 1978 | Takahashi, et al. |
| 4,165,633 | August 28, 1979 | Raisanen |
| 4,168,623 | September 25, 1979 | Thomas, Jr. |
| 4,193,116 | March 11, 1980 | Funk |
| 4,276,462 | June 30, 1981 | Risman |
| 4,291,775 | September 29, 1981 | Collins |
| 4,312,218 | January 26, 1982 | Eckles |
| 4,316,384 | February 23, 1982 | Pommer, et al. |
| 4,390,768 | June 28, 1983 | Teich, et al. |
| 4,398,835 | August 16, 1983 | Athey, et al. |
| 4,413,168 | November 1, 1983 | Teich |
| 4,438,500 | March 20, 1984 | Collins, et al. |
| 4,457,632 | July 3, 1984 | Collins, et al. |
| 4,554,132 | November 19, 1985 | Collins |
| 4,565,669 | January 21, 1986 | Collins, et al. |
| 4,566,312 | January 28, 1986 | Collins, et al. |
| 4,566,804 | January 28, 1986 | Collins, et al. |
| 4,651,285 | March 17, 1987 | Collins, et al. |
| 4,681,996 | July 21, 1987 | Collins, et al. |
| 4,749,054 | June 7, 1988 | Virtanen, et al. |
| 4,750,143 | June 7, 1988 | Heitz, et al. |
| 4,753,889 | June 28, 1988 | Collins |
| Re. 32,861 | February 7, 1989 | Collins, et al. |
| 4,835,354 | May 30, 1989 | Collins, et al. |
| 4,838,705 | June 13, 1989 | Byers, Jr. et al. |
| 4,861,556 | August 29, 1989 | Neas, et al. |
| 4,882,286 | November 21, 1989 | Neas, et al. |
| 4,946,797 | August 7, 1990 | Neas, et al. |
| 5,211,252 | May 18, 1993 | Henderson, et al. |
| 5,215,715 | June 1, 1993 | Haswell, et al. |
| Re. 34,373 | September 7, 1993 | Collins, et al. |
| 5,318,754 | June 7, 1994 | Collins, et al. |
| 5,420,039 | May 30, 1995 | Renoe, et al. |
| 5,632,921 | May 27, 1997 | Risman, et al. |

SUMMARY OF THE INVENTION

The instant invention is distinguished over the known prior art in a multiplicity of ways. For one thing, the instant invention provides a microwave moisture analyzer for loss on drying applications which provides fast and accurate quantitative analysis of a vast array of products which are manufactured subject to strict control of moisture. The instant invention also provides fast and uniform drying of product samples for real-time process control without degradation of the sample due to charring. In addition, the instant invention provides microwave energy means for providing real time feedback during the drying process of the sample thus, inter alia, maintaining tight tolerances of the drying process. Furthermore, the instant invention provides a microwave moisture analyzer which is impervious to vibration and jarring in the working environment thereby eliminating anomalous weight readings which result in unpredictable and unreliable moisture determination of the sample. Moreover, the instant invention solves the problem of over drying the product and the possibility of the product igniting in the analyzer. The instant invention also includes automated functions which simplify routine analysis thereby substantially eliminating the dependency of the result of the analysis of the skill and care exercised by the operator.

In a preferred form, the microwave moisture analyzer of the instant invention includes, a power supply, a magnetron, a power module operatively coupled between said power supply and said magnetron for driving said magnetron, a wave guide communicating with the magnetron and with a microwave containment chamber for delivering energy thereto, at least one microwave energy sensor for sensing microwave energy or magnetic and/or electric field strengths within the chamber for controlling, inter alia, the loss on drying process of the sample being assayed and determining when the drying process is complete. A precision electronic balance is operatively disposed within the microwave chamber for allowing a specimen being assayed to be weighed. In addition, a ventilation chamber is provided for venting moisture from the microwave chamber. A processing unit and associated memory allows means for data acquisition, processing and storage of data from the power module driving the magnetron, the microwave energy sensor(s) for sensing magnetic and/or electric fields and the electronic balance for weighing the initial and final weights of the specimen for loss on drying moisture analysis, both signaling the removal of microwave energy in the chamber.

In addition, the microwave moisture analyzer of the instant invention includes a sample rotation module which rotates the sample during the drying process. Furthermore, a smoke/gas detector module and a flash detector module can be operatively disposed within the analysis chamber 260. The smoke/gas detector module provides means indicating endpoint runover. The flash detector module provides means for providing a warning if a sample begins to ignite within the analysis chamber.

The microwave containment chamber is partitioned into a lower chamber and an upper chamber wherein the upper chamber is pivotally coupled to said lower chamber such that said upper chamber can move from a closed substantially horizontal position to an opened upright positioned for toploading of a specimen faster. The upper and lower chamber when in a closed position define a internal cavity having a base, cylindrical sidewalls extending from said base and operatively coupled thereto and a perforated top wall wherein moisture can be aspirated therethrough without allowing microwave leakage. The base of the cylindrical chamber includes a pair of portals disposed approximately ninety degrees apart such that the energy delivered from the magnetron can be guided to the portals via a bifurcated wave guide for delivering energy within the cylindrical cavity of the microwave containment chamber. At least one microwave energy sensor is disposed in operative communication with the microwave containment chamber for sensing microwave energy therein for controlling the drying process and determining when a drying cycle is complete.

In addition, a pair of tuning rods are disposed within the interior of the containment chamber at a location above the portals. The tuning rods are used to set-up the microwave mode entering the chamber into a resonance condition. Specifically, the tuning rods set-up two resonances such that they interact with one another to create a magnetic stirring without the use of a mechanical stirrer. Preferably, the tuning rods traverse a median of the portals.

Furthermore, an attenuator is provided within one of the two bifurcated members of the waveguide communicating energy between the magnetron and the microwave chamber. The tuning stub is used to attenuate a third mode of energy within a wave guide to increase the efficiency of the dual mode wave guide field creating a cylindrical stirring effect.

OBJECTS OF THE INVENTION

Accordingly, a primary object of the instant invention is to provide a new, novel and useful microwave moisture analyzer apparatus and method for loss on drying applications.

A further object of the instant invention is to provide a self contained, programmable moisture analyzer apparatus with microwave radiation and automatic determination of weight loss, suitable for non-flammable and non-toxic samples.

Another further object of the instant invention is to provide the apparatus and method as characterized above in which samples are heated using microwave energy to liberate moisture or other volatiles while sensing microwave energy until endpoint conditions are met.

Another further object of the instant invention is to provide the apparatus and method as characterized above which employs microwave energy sensor means for controlling the drying process and determining that a drying cycle is complete.

Another further object of the instant invention is to provide the apparatus and method as characterized above which employs microwave energy sensor means for sensing magnetic and/or electric fields.

Another further object of the instant invention is to provide the apparatus and method as characterized above which employs the microwave energy sensor means to detect an increase in unabsorbed energy by a load.

Another further object of the instant invention is to provide the apparatus and method as characterized above which employs the microwave energy sensor means for controlling the microwave power shut off.

Another further object of the instant invention is to provide the apparatus and method as characterized above which employs a sample rotation module which rotates the sample during the drying process.

Another further object of the instant invention is to provide the apparatus and method as characterized above which employs a smoke/gas detector module for providing means indicating endpoint runover.

Another further object of the instant invention is to provide the apparatus and method as characterized above which employs a flash detector module for providing a warning if a sample begins to ignite within the analysis chamber.

Another further object of the instant invention is to provide the apparatus and method as characterized above which uses a high percentage of $T_m$ waves for allowing a lower power usage relative to conventional microwaves.

Another further object of the instant invention is to provide the apparatus and method as characterized above which includes a tuned wave guide and a tuned cylindrical induction microwave chamber.

Another further object of the instant invention is to provide the apparatus and method as characterized above which substantially reduces drying time compared with known methodologies.

Another further object of the instant invention is to provide the apparatus and method as characterized above which substantially reduces drying time without degradation of samples due to, inter alia, a reduced cavity size (e.g. 10% of a conventional oven cavity) of a micro wave containment chamber thereby resulting in a favorable filling factor, i.e., the sample size divided by the cavity volume.

Another further object of the instant invention is to provide the apparatus and method as characterized above which is fast, accurate and easy to use.

Another further object of the instant invention is to provide the apparatus and method as characterized above which automatically calculates loss on drying moisture determination and documents the analysis on, inter alia, an internal printer and a video graphics array (VGA) display for providing good lab practice (GLP) and ISO support.

Another further object of the instant invention is to provide the apparatus and method as characterized above which allows setup by merely selecting an appropriate routine from a menu-driven software displayed on a backlit LCD display.

Another further object of the instant invention is to provide the apparatus and method as characterized above which allows the user to enter drying parameters by entering them through a keypad either by touching a corresponding number or entering the exact value with numeric keys.

Another further object of the instant invention is to provide the apparatus and method as characterized above which provides a development screen which conveniently illustrates the drying parameters including units, a plurality of temperatures and end-point selection for defining drying procedures.

Another further object of the instant invention is to provide the apparatus and method as characterized above which allows the drying procedures to be stored in the memory for later recall via meaningful alphanumeric program names.

Another further object of the instant invention is to provide the apparatus and method as characterized above which allows one key actuation of a drying procedure which has been established and recalled from memory with meaningful alphanumeric program names.

Another further object of the instant invention is to provide the apparatus and method as characterized above which provides easy operator ergonomics and cleaning via top entry of samples.

Another further object of the instant invention is to provide the apparatus and method as characterized above which provides meaningful recall from memory/data acquisition and graphical/plotting displays.

Viewed from a first vantage point, it is an object of the present invention to provide a loss on drying apparatus, comprising in combination: a microwave chamber; a microwave energy source operatively coupled to the chamber for delivering microwave energy thereto for drying a sample therein; a microwave energy sensor operatively disposed within the microwave chamber.

Viewed from a second vantage point, it is an object of the present invention to provide a method for loss on drying, the step including: placing a specimen in a cylindrical microwave; monitoring the microwave energy within the cylindrical microwave while powering the microwave to dry the specimen; venting moisture from the microwave during a drying process.

Viewed from a third vantage point, it is an object of the present invention to provide a microwave moisture analyzer, comprising in combination: a cylindrical microwave containment chamber; the cylindrical microwave containment chamber including a pair of portals disposed therein; a microwave energy source; a wave guide operatively coupled between the microwave energy source and the portals for delivering microwave energy to the chamber; means for supporting a sample within the chamber; means for sensing microwave energy for controlling the amount of microwave energy delivered to the chamber as a function of the sample being analyzed.

Viewed from a forth vantage point, it is an object of the present invention to provide a method for loss on drying, the steps including: placing a specimen in a cylindrical microwave; delivering microwave energy to the cylindrical microwave; monitoring the microwave energy within the cylindrical microwave; controlling a drying process of the specimen as a function of the monitored microwave energy.

Viewed from a fifth vantage point, it is an object of the present invention to provide a method for loss on drying, the steps including: placing a sample in a chamber; weighing the sample to obtain an initial weight thereof; applying microwave energy to a chamber containing the sample; sensing the microwave energy within the chamber for controlling a drying process of the sample to a endpoint by modifying the amount of applied microwave energy; reweighing the sample at an end of the drying process to obtain a final weight thereof.

Viewed from a sixth vantage point, it is an object of the present invention to provide a method for loss on drying, the steps including: applying microwave energy to a sample having a known weight; monitoring the microwave energy; surceasing the applied microwave energy as a function of the monitored microwave energy.

Viewed from a seventh vantage point, it is an object of the present invention to provide a method for loss on drying, the steps including: applying microwave energy to a sample having a known weight and contained with in a chamber; sensing the energy within the chamber and outputting a signal correlative to the sensed energy; comparing the outputted signal to a predetermined signal level; regulating the applied microwave energy as a function of the comparison step for drying the sample.

Viewed from a eighth vantage point, it is an object of the present invention to provide a method for loss on drying, the steps including: establishing an algorithm correlative to a change in radiation as function of load absorbability; sensing radiation correlative to an absorbability of a load being radiated within a chamber; comparing the sensed radiation to the algorithm for determining a benchmark correlative to an endpoint condition.

Viewed from a ninth vantage point, it is an object of the present invention to provide a method for loss on drying, the steps including: establishing a characteristic radiation curve of a sample type correlative of its radiation absorbability; radiating a specimen of the sample type; developing a specimen radiation curve by monitoring a change in radiation correlative to radiation absorbability of the specimen; comparing a transition of slope on the characteristic radiation curve with a transition of slope on the specimen radiation curve; continuing to radiate the specimen until a predetermined endpoint condition has been met based on the comparison step.

Viewed from a tenth vantage point, it is an object of the present invention to provide a method for loss on drying, the steps including: establishing a benchmark correlative to a level of microwave energy sensed by a sensor; employing the sensor to monitor a level of microwave energy within a chamber wherein a sample is being radiated; comparing the monitored energy level with the benchmark level for controlling a drying process of the sample.

Viewed from a eleventh vantage point, it is an object of the present invention to provide a method for loss on drying, the steps including: establishing a characteristic radiation curve of a sample type correlative of its radiation absorbability; radiating a sample contained within a chamber; comparing subsequently sensed levels of radiation within the chamber with the characteristic curve for determining an endpoint condition.

These and other objects will be made manifest when considering the following detailed specification when taken in conjunction with the appended drawing figures.

BRIEF DESCRIPTION OF THE DRAWINGS

FIG. 20b is a front plan view of the sample rotation module shown in FIG. 20a.

FIG. 22 is a block diagram of a balance including a two piece weighing rod according to the instant invention.

DESCRIPTION OF PREFERRED EMBODIMENTS

Figure 1:
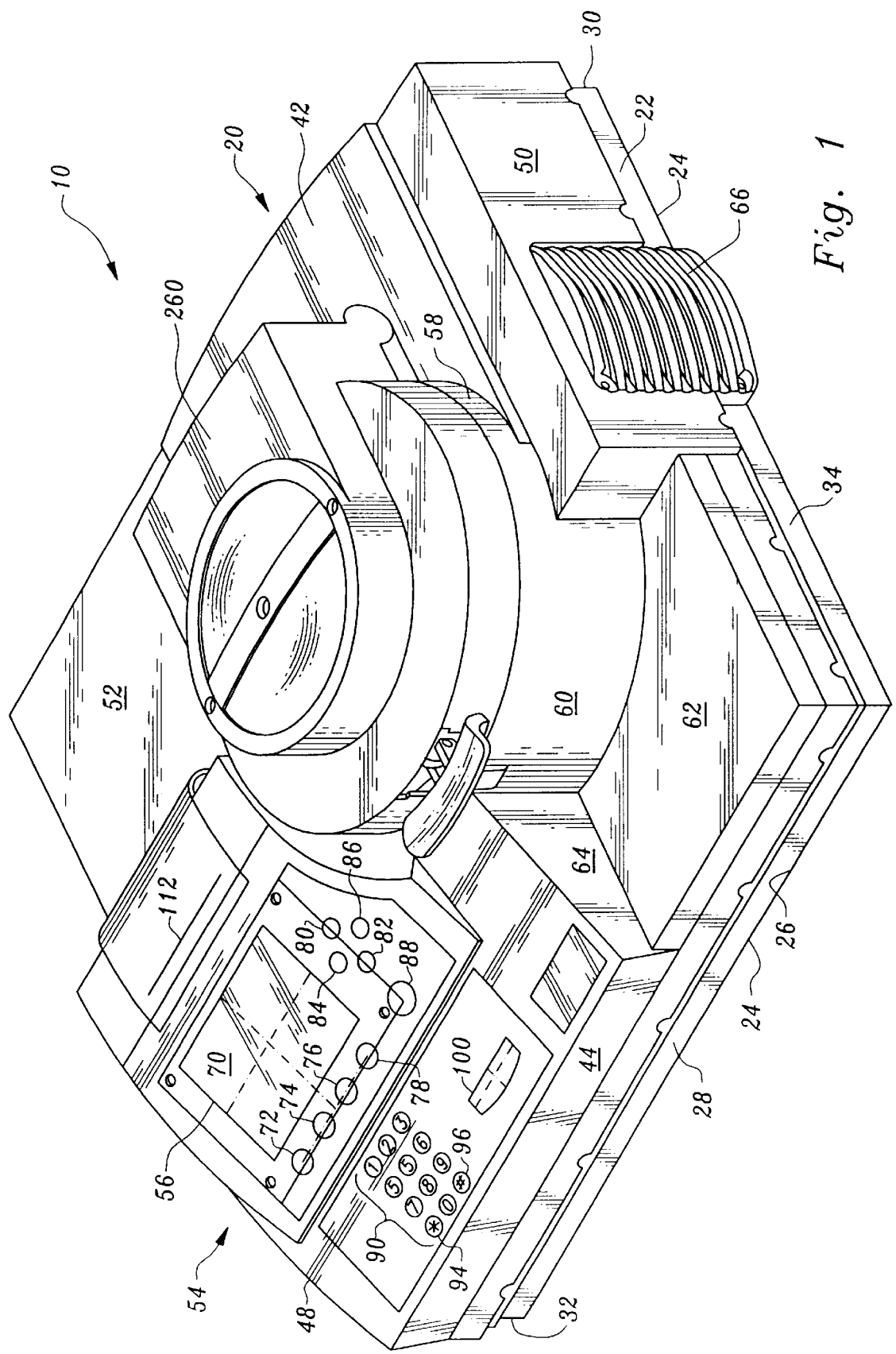
FIG. 1 is an elevational view from a front and side of the microwave moisture analyzer apparatus.

Considering the drawings, wherein like reference numerals denote like parts throughout the various drawing figures, reference numeral 10 is directed to the microwave moisture analyzer apparatus according to the instant invention.

Figure 2:
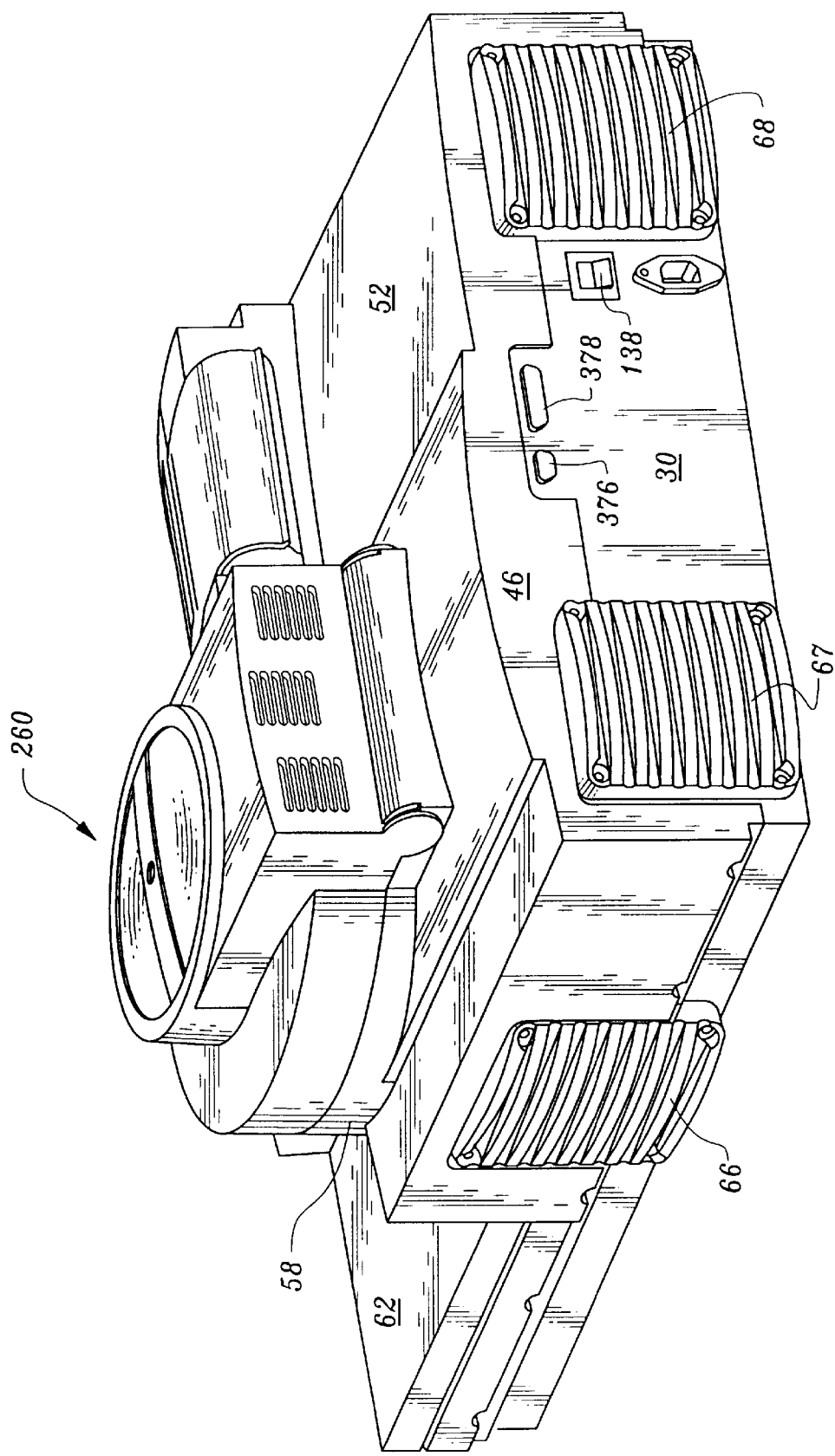
FIG. 2 is an elevational view from a side and rear of the apparatus.

In its essence and referring to FIGS. 1 and 2, the apparatus 10 according to the instant invention includes an enclosure 20 which includes a lower housing 22 and an upper housing 42. The lower housing 22 includes a planar bottom surface 24 having an outer periphery 26 with upwardly extending walls 28, 30, 32, 34 integrally formed with the periphery, thereby defining an opened top box (please see FIG. 5). The opened top box includes a plurality of partitioned areas which sequester different parts of the apparatus 10 into sectors. For example, one sector is an area where a the power supply 120 is located and includes a ventilation means including a fan 152 passing through one of the side walls 30 to preclude adverse thermal excursions. Similarly, a second sector is provided which circumscribes a magnetron 170 and is similarly equipped with ventilation by means of a fan 176 to prevent unwanted temperature build-up and extend the life of the magnetron. A third sector is where an integral precision electronic balance 240 and a sample rotation module 540 is housed which both communicate with the analysis chamber 260. The wave guide 200 communicates with a base 262 of a analysis chamber 260 which includes first and second portals 264, 266 and a centralized bore 270 in which a two piece weighing rod 242 passes therethrough. The two piece weighing rod 242 communicates with both the electronic balance 240 and the sample rotation module 540. The wave guide 200 substantially divides in quadrature, 90 degrees offset branches 204, 206 and portals 264, 266 from the base plate 262 extend upwardly to provide radiation to the sample being assayed and subsequently manipulated for a loss on drying analysis. Each of the partitioned areas are independently accessible depending on requisite need, whether it be for maintenance or subsequent utilization in its intended working environment. The area above the balance 240 and where the microwave power is outputted includes a hinged and spring lift covered microwave analysis chamber 260 (please see FIG. 8). The hinged cover or upper chamber 300 includes a vent means 312 (FIG. 11) associated therewith and circulatory means to remove moisture during a loss on drying analysis. The hinged cover 300 protects the user by a plurality of micro-switches which disable the magnetron 170 should the cover 300 be opened while the apparatus 10 is in operation or if the cover 300 is improperly closed.

Figure 6:
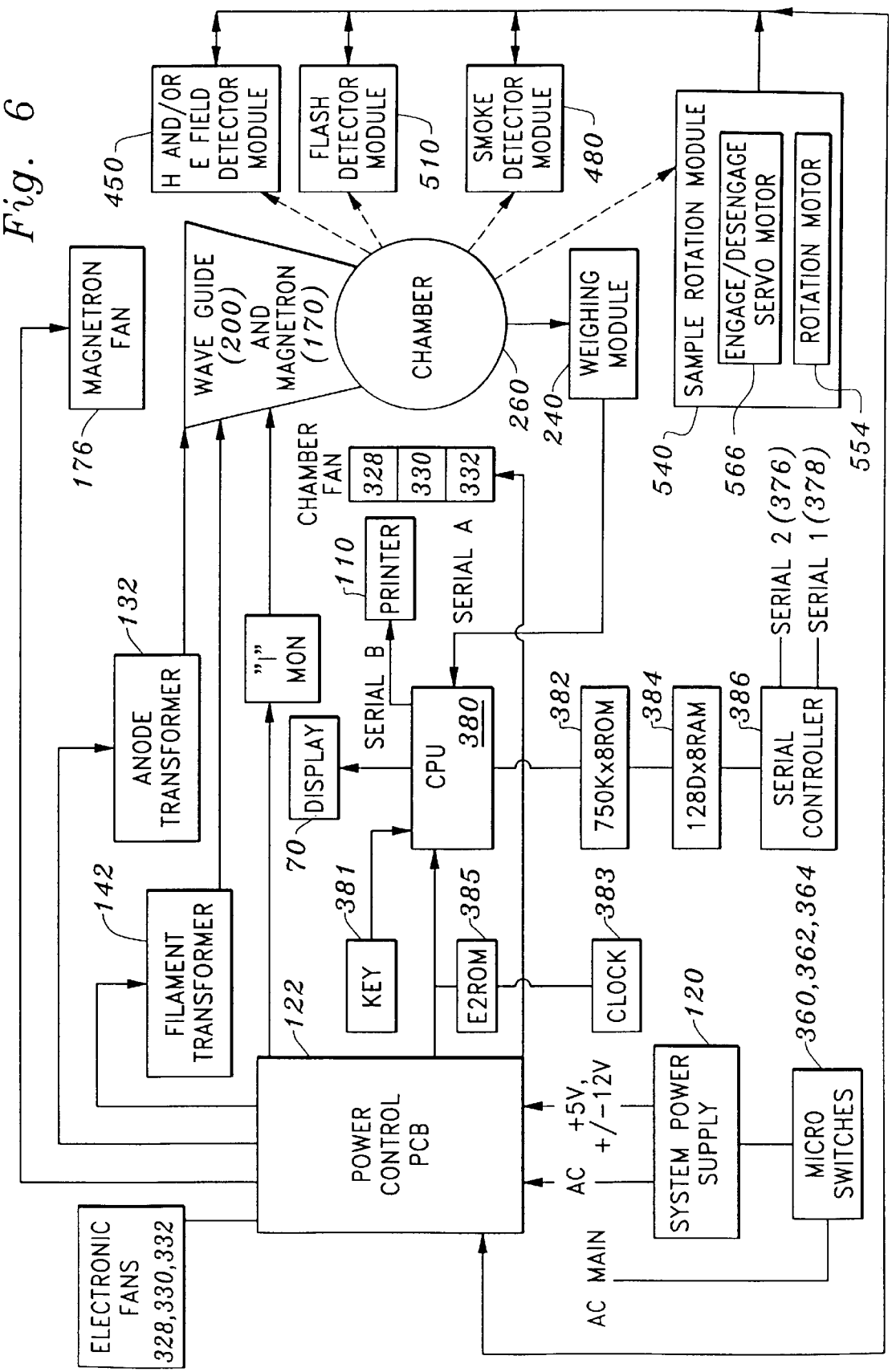
FIG. 6 is a system schematic of the apparatus including a microwave energy detector module, a smoke/gas detector, a flash detector module and a sample rotation module.
Figure 11:
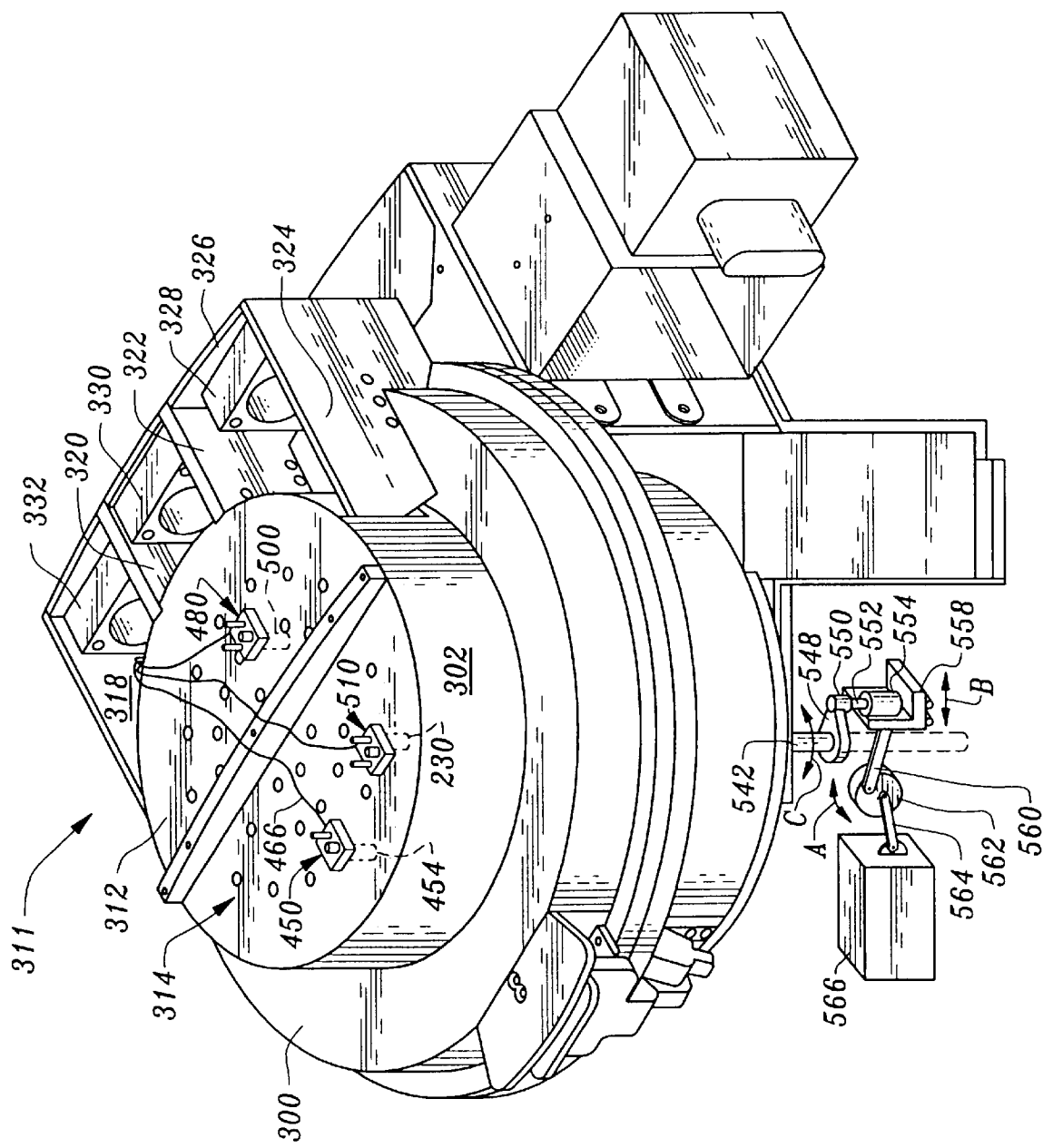
FIG. 11 is a front side elevational view of the microwave containment chamber, with a top cover removed therefrom and the sample rotation module.

In addition, and referring to FIGS. 1, 6 and 11, the apparatus 10 includes a microwave energy module 450 operatively disposed within the analysis chamber 260. The microwave energy module 450 controls, inter alia, the loss on drying process of the sample being assayed and determines when the drying process is complete by sensing magnetic and/or electric field strength, i.e., energy within the microwave analysis chamber 260. One principal analogy of this sensing technique is that the module 450 will sense energy heretofore allocated to drying the sample wherein the sensed energy is correlative to the energy unabsorbed by the load.

Prior to the drying process sample is placed between two glass pads and disposed on a carriage 250 within the chamber 260. The carriage communicates with the electronic balance and a sample rotation module 540 via the two piece weighing rod 242. The sample is weighed prior to and after the drying process. During the drying process of the sample it is preferred that the carriage 250 is rotated by the sample rotation module 540. Thus, the two piece weighing rod 242 serves a dual purpose: providing a support member for the sample to be weighed by the electronic balance and providing a rotatable member for the sample rotation module 450 to couple to for rotating the sample.

Furthermore, a smoke/gas detector module 480 and a flash detector module 510 can be operatively disposed within the analysis chamber 260. The smoke/gas detector module 480 provides means for detecting a gas product in the form of, for example, carbon dioxide. Thus, the smoke/gas detector module 480 provides means for indicating endpoint runover. The flash detector module 510 provides means for measuring and/or detecting radiant energy particularly in the form of light. Thus, the flash detector module 510 provides us a warning if a sample begins to ignite within the analysis chamber 260.

More specifically and referring to FIGS. 1 and 2, the upper housing 42 includes a top surface 52 and a circumscribing well 58 for receiving the analysis chamber 260. The top surface 52 of the upper housing 42 includes a user access area 54 for allowing a user to have access to a display 70, a plurality of soft keys 72, 74, 76, 78, direction keys 80, 82, 84, 86, an enter key 88, a numeric keypad 90 and a start key 100 and a printer slot 112 for receiving printed output. This area is downwardly sloped so that the user may easily view the display 70 and operate the plurality of keys before, during and after assaying the sample. The keys are surface mounted to protect against spillage. The display 70 is viewed through a display window 56 disposed in the top surface 52 of the upper housing 42. Preferably, there are four soft keys 72, 74, 76, 78 which are disposed directly under the display 70. In addition, the direction keys 80, 82, 84 and 86 are disposed through the top surface 52 of the upper housing 42 in a cruciform configuration. The enter key 88 is located to the right of the display 70 and below the directional keys. The numeric keypad 90 is disposed through the top surface 52 of the upper housing 42 at a location beneath both the display and the plurality of soft keys. The numeric keypad 90 includes ten numeric keys and a decimal and asterisk key 94, 96 allocated in four rows of three keys each thereby defining a 4 by 3 matrix. Furthermore, an oversized start key 100 is located to the right of the 4 by 3 matrix of keys 90.

The circumscribing well 58 of the upper housing 42 receives the analysis chamber 260. The upper housing 42 includes an integrally formed horizontally disposed planar work surface 62 located at the front right hand corner of the upper housing 42. The work surface 62 is formed at a lower elevation than the sloped user access area 54 and the upper chamber 300 of microwave analysis chamber 260 and can be employed as, inter alia, an area where a sample is placed between two quartz (glass) pads and/or plastic pans which are both microwave transparent. The work surface 62 transitions into a substantially planar vertically extending sidewall 64 and a front circular wall 60 of the circumscribing well 58 receiving the analysis chamber 260. In addition, the upper housing 42 includes an outer periphery with downwardly extending side walls 44, 46, 48, 50. The downwardly extending side wall 50 that defines the right side of the upper housing 42 includes an opening covered by a first air grill 66. In addition, the upper housing 42 is provided with a pair of spaced apart openings disposed in a back wall 46 for receiving a second and third air grill 67, 68 which communicate with a fan 152 cooling the electronics and power supply and the fan 176 providing temperature stability of the magnetron 170. The right side grill 66 allows air to enter through perforations disposed in side wall 34 and then into the magnetron sector, over the magnetron 170 and then out through the fan 176 disposed on the back wall 30 of the lower housing 22 and back into the environment for providing cooling of the magnetron 170.

Figure 3:
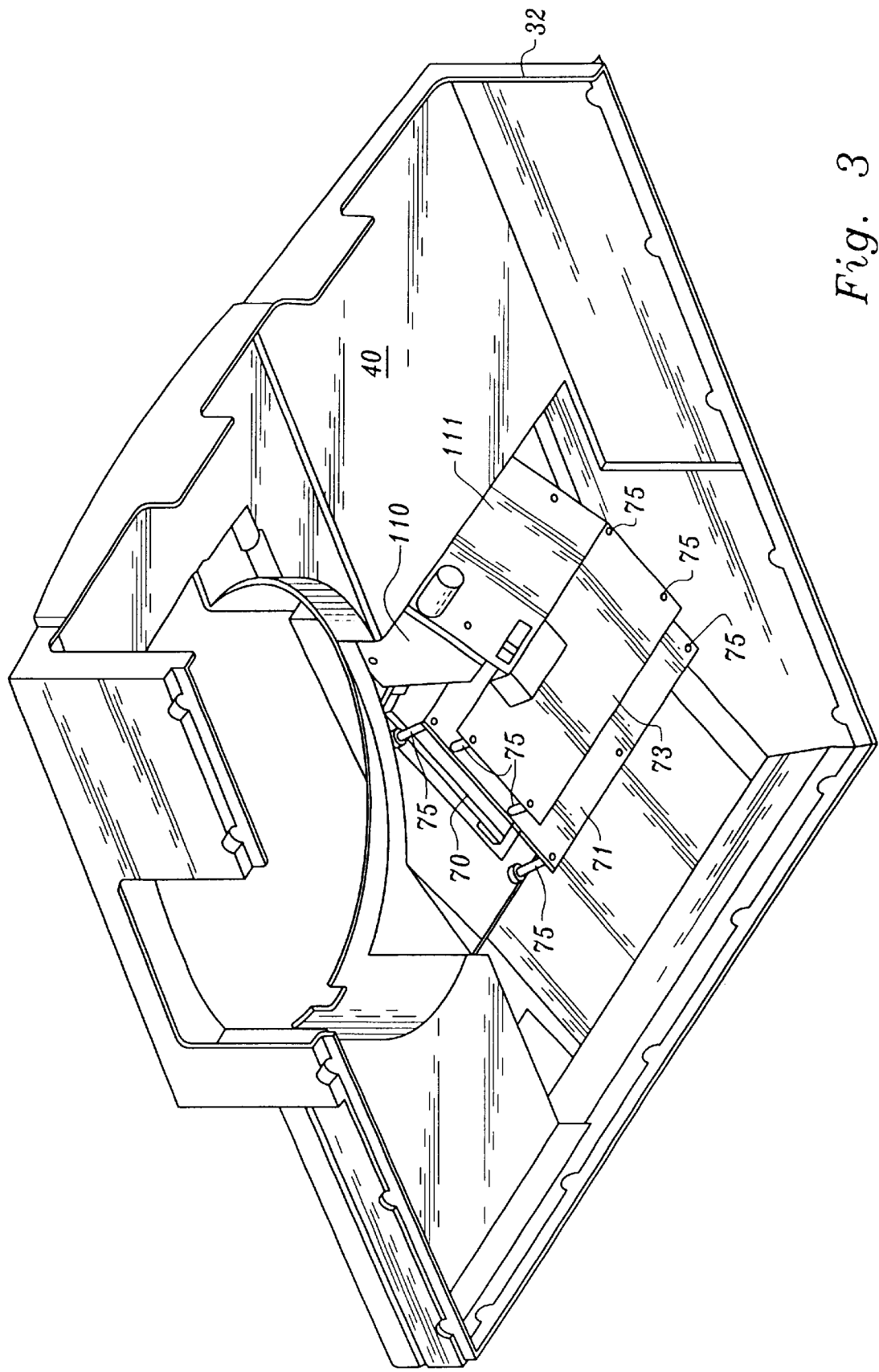
FIG. 3 is an elevational view of an underside of an upper housing according to the instant invention.

Referring to FIG. 3, an underside 40 of the upper housing 42 is shown. The underside of the upper housing 42 supports the display 70, a digital board 71 and a display driver board 73 for driving the display 70. A plurality of stand-offs 75 are used as known in the art to connect the display 70, the digital board 71 and the driver board 73 in a parallel spaced apart relationship with respect to one another. In addition, the underside of the cover supports the printer 110 which is preferably a two hundred fifty six dot wide thermal graphics printer and a printer controller board 111 which are shown to be disposed above the display 70.

Figure 4:
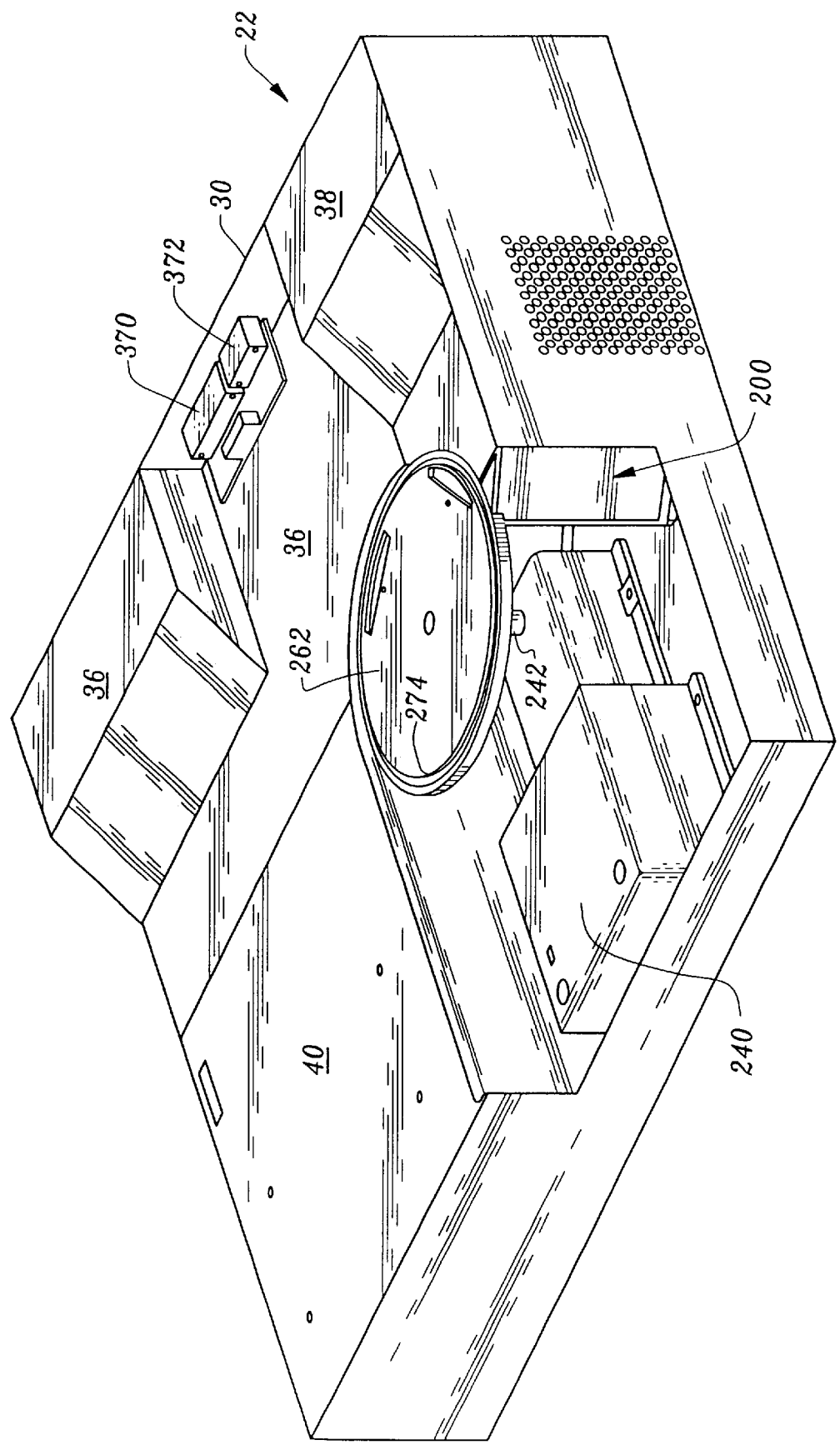
FIG. 4 is an elevational view from a front and side of the apparatus with the upper housing removed.

Referring to FIG. 4, the electronic balance 240 is shown disposed in a right front sector of the apparatus 10. The electronic balance 240 communicates with the base 262 of the analysis chamber 260 via a weighing rod 242 and the base 262 is directly coupled to the quadrature wave guide 200. In addition, a plurality of fan covers 36, 38 and an electronic cover 40 precludes access to the components therein when the upper housing 42 is removed from the lower housing 22. Furthermore, a plurality of serial communication ports 370, 372 are disposed in the back wall 30 of the lower housing 22 and interposed between the fans covers 36, 38.

Figure 5:
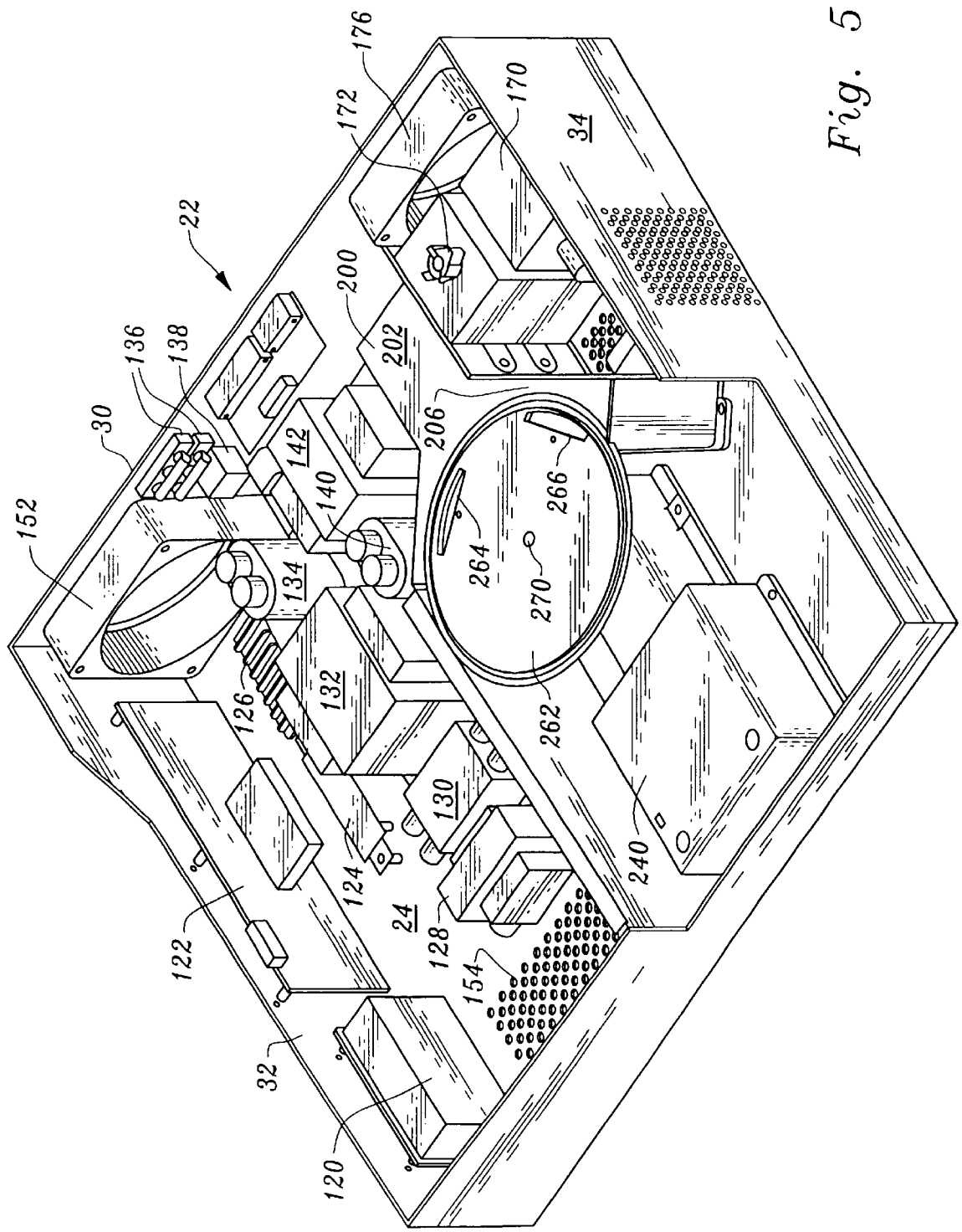
FIG. 5 is a front side elevational view of the apparatus with the upper housing and cover plates removed.

Referring to FIG. 5, the lower housing 22 is shown with the upper housing 42 and covers 36, 38, and 40 removed therefrom thereby defining the open boxed structure. The power supply fan 152 is disposed on the back wall 30 of the first sector to provide ventilation for the components located therein. The first sector also includes a fuse block 136 for holding the fuses shown in FIGS. 20 and 21 and a power or on/off switch 138 which are disposed in the back wall 30 of the lower housing 22. In addition, the first sector includes a filament transformer 142, a capacitor 134, a back up capacitor 140, a terminal block 126, an anode transformer 132, a resistor bar 124, a filter 130, an isolation transformer 128, a power supply 120 and a power supply module or board 122. Preferably, the power supply module 122 and the power supply 120 are connected to a side wall 32 of the lower housing 22. Specifically, the left side wall 32 when viewed from the front of the apparatus 10. The filament transformer 142, capacitor 140, back-up capacitor 134, anode transformer 132, filter 130 and isolation transformer 128 are spaced apart from the power board 122 and power supply 120 and interposed therebetween and coupled to bottom surface 24 along with the resistor bar 124 and terminal block 126. Thus, the ventilation fan 152 receives air from a perforated opening 154 disposed in surface 24 towards, the front of the sector and induces air to flow over the components and through the fan 152 into the environment without the heat removal being impeded by the components contained therein.

Referring to FIGS. 5 and 22, the second sector includes the integral electronic balance 240 which communicates with a carriage 250 holding the sample to be assayed by way of a weighing rod 242. The weighing rod 242 extends through the centralized bore 270 of the base 262 of the analysis chamber 260 and is connected to a substantially horizontal lever arm 244 of the balance 240. The lever arm 244 of the balance is operatively coupled to a vertically extending arm 246 which in turn is operatively coupled to a beam 247 connected to a coil 248 circumscribed by a winding 249. Thus, weight disposed on the pan will cause motion along the arrow F which effects torque on a rod which displaces the coil 248 which is disposed in a field wherein the displacement on the coil 248 can be translated into a current or voltage correlative to the sample weight disposed on the pan. This type of electronic balance is known in the art as a toploading electronic balance. The balance 240 in combination with the top loading microwave chamber 260 allows a sample to be loaded into the camber 260 and onto the carriage coupled to the weighing rod 242 without damaging or breaking flexural bearings springs of the balance. In addition, balance is guarded against vibration and electrical noise effects of the magnetron.

The third sector of the lower housing 22 includes the magnetron fan 176 disposed in the back wall 30 of the lower housing 22, the magnetron 170, a thermal switch 172 and the quadrature wave guide 200. Air enters through a perforated right side wall 34 of the lower housing 22 and flows over the magnetron 170 through the fan 176 and back into the environment via fan operation. The thermal switch 172 is coupled to the main power supply 120 to provide protection so that the magnetron is shut off if excessive temperatures are reached. The magnetron 170 couples to a side 208 of a base 202 of a substantially Y shaped wave guide 200. The base 202 of the wave guide 200 bifurcates into the first wave guide channel 204 and the second wave guide channel 206. The first and second wave guide channels 204, 206 both communicate with the canoe shaped openings or portals 264, 266 disposed in the base 262 of the analysis chamber 260 such that radiation is emitted therethrough.

Referring to FIG. 6, a system schematic is shown of the apparatus according to the instant invention. The system includes a central processing unit 380 operatively coupled to a read only memory (ROM) 385, a random access memory (RAM) 384 and a serial controller 386 thereby allowing means for data acquisition, processing and storage. In addition, the serial controller 386 is operatively coupled to the serial ports 376, 378 for allowing bi-directional communication between the central processor 380 and an external computer or peripheral. In addition, the central processor 380 is operatively coupled to keys 381 which include the soft keys 72, 74,, 76, and 78, direction keys 80, 82, 84 and 86, enter key 88, numeric keypad 90 and start key 100 disposed on the top surface 52 of the upper housing 42. In addition, the central processor 380 is operatively coupled to the display 70 and to the printer 110 for providing the display of information on the display 70 and a hard copy readout of information via the printer 110. Furthermore, an electrically erasable read-only memory 385 is operatively coupled between a power control board 122 and the central processing unit 380 for providing, inter alia, preprogrammed LOD routines. Clock 383 provides the timing for memory 385.

The central processing unit 380 receives data from the balance or weighing module 240 and the power control module or board 122. The power control module 122 is operatively coupled to the system power supply 120 and is directly interrupted by at least one of the micro-switches 360, 362, 364, and 366 located on the lower chamber 280 of the microwave containment chamber 260. The power control board 122 is operatively coupled to an anode transformer 132 and the filament transformer 142 which are in turn connected to the magnetron 170 disposed on the wave guide 200. In addition, the power control board is operatively coupled to the magnetron fan 176 for controlling the temperature of the environment in which the magnetron 170 is disposed. The details of the power control board, the filament transformer 142, the anode transformer 132 and the magnetron 170 will be described infra.

The central processing unit 380 receives signals from the balance 240 which are indicative of the weighing of the sample being assayed within the microwave containment chamber 260. Thus, the central processing unit 380 receives signals from both the power control module 122 and the balance 240 which are indicative of the power being supplied to the magnetron 170 and thus the microwave containment chamber 260 while assaying the sample and also the weight of the sample before and after assaying of the sample.

Figure 7:
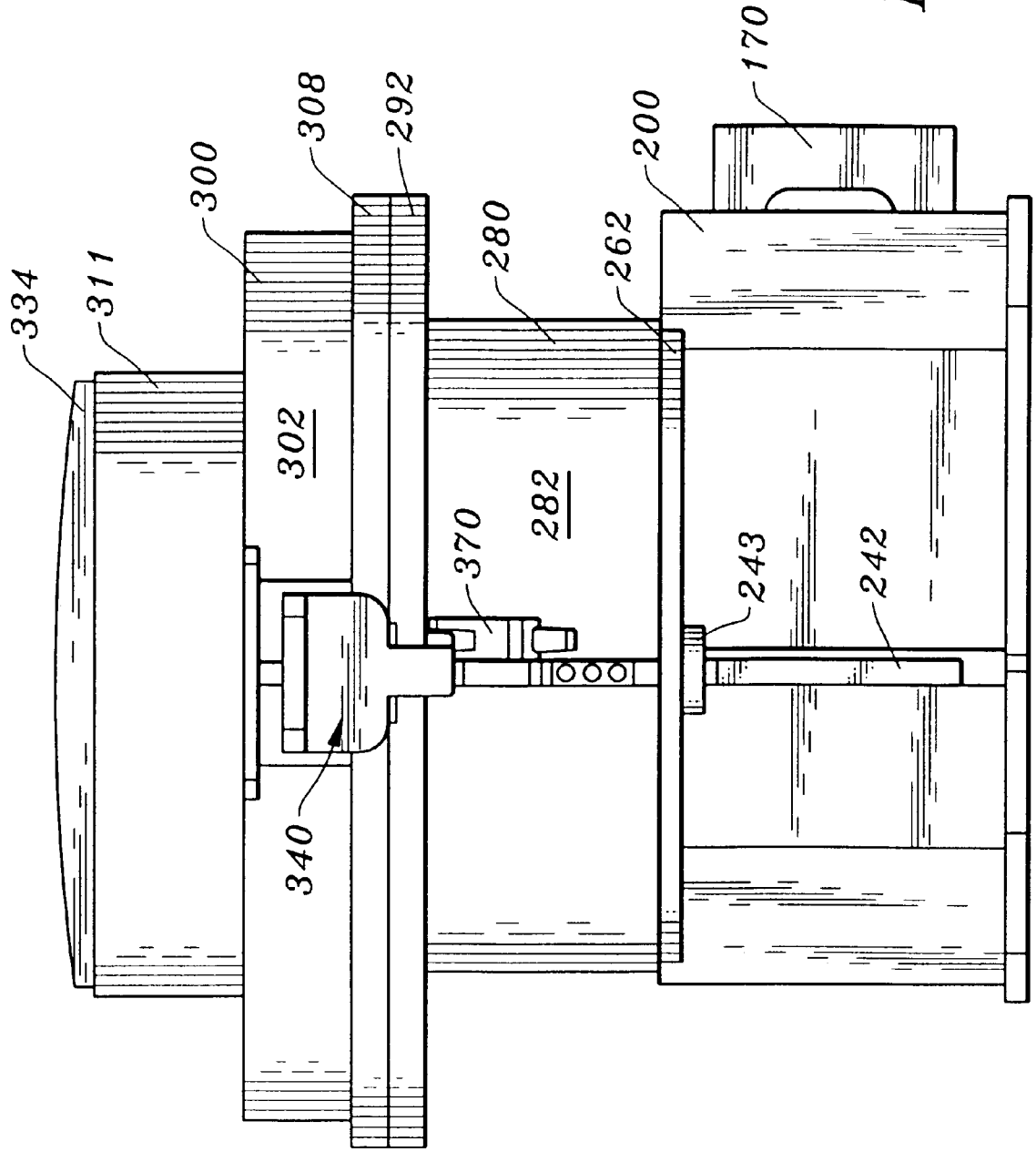
FIG. 7 is a front plane view of a microwave containment chamber and a wave guide.

Referring to FIG. 7, a front plane view of the microwave containment chamber 260 is shown operatively coupled to both the weighing rod 242 of the balance 240 and the wave guide 200 interposed between the microwave containment chamber 260 and the magnetron 170. The weighing rod 242 passes through a collar 243 prior to extending into the chamber 260 via the centralized bore 270. The microwave containment chamber 260 is partitioned into the lower chamber 280 and the upper chamber 300. The lower chamber 280 includes the base 262 having an outer peripheral annulus groove 274 (see FIG. 4) coupling to a side wall 282 having an interior cylindrical side wall 286 (see FIG. 14) vertically extending upwards to a lower sealing flange 292. The upper chamber 300 has a complemental sealing flange 308 including a choke 310 which defines the partition between the upper and lower chambers 300, 280 respectively. The upper sealing flange 308 transitions into a cylindrical wall 302 also having an interior cylindrical side wall 306 defining a partitioned cylindrical microwave cavity of the containment chamber 260 along with the lower interior cylindrical wall 286. The upper cylindrical wall 302 transitions into a moisture evacuation compartment 311 via a perforated top 312 which is covered by a lid 334. The upper chamber 300 is coupled to the lower chamber 280 via a latch means 340 which interacts with at least one micro-switch 370 which is directly coupled to the main power supply 120 delivering power to the magnetron 170 wherein the power supply 120 is inoperative when at least the one micro-switch 370 is in an opened positioned thereby disallowing false starts of the magnetron 170.

Figure 8:
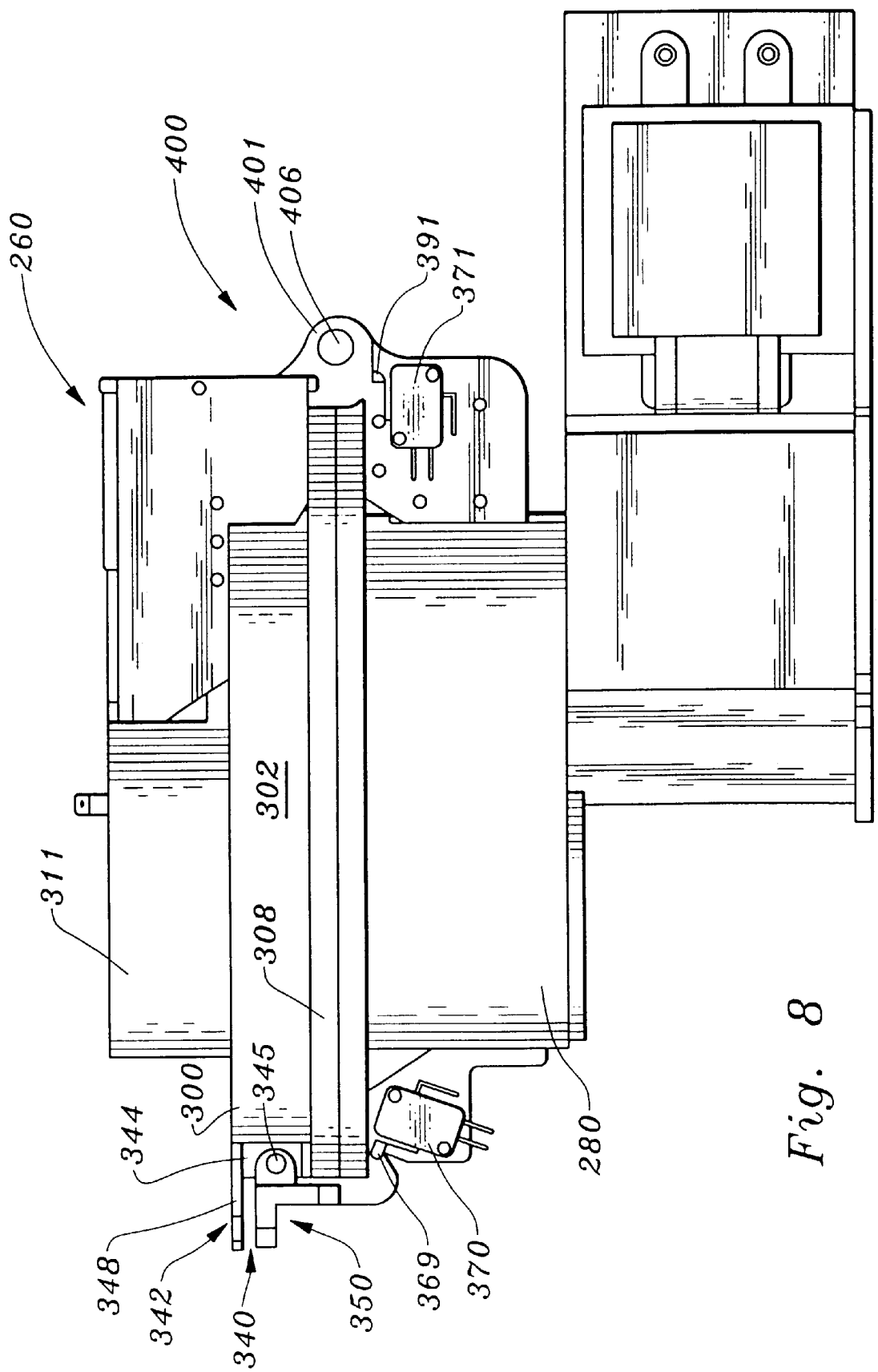
FIG. 8 is a right plane view of the microwave containment chamber, the wave guide, and a magnetron.
Figure 9:
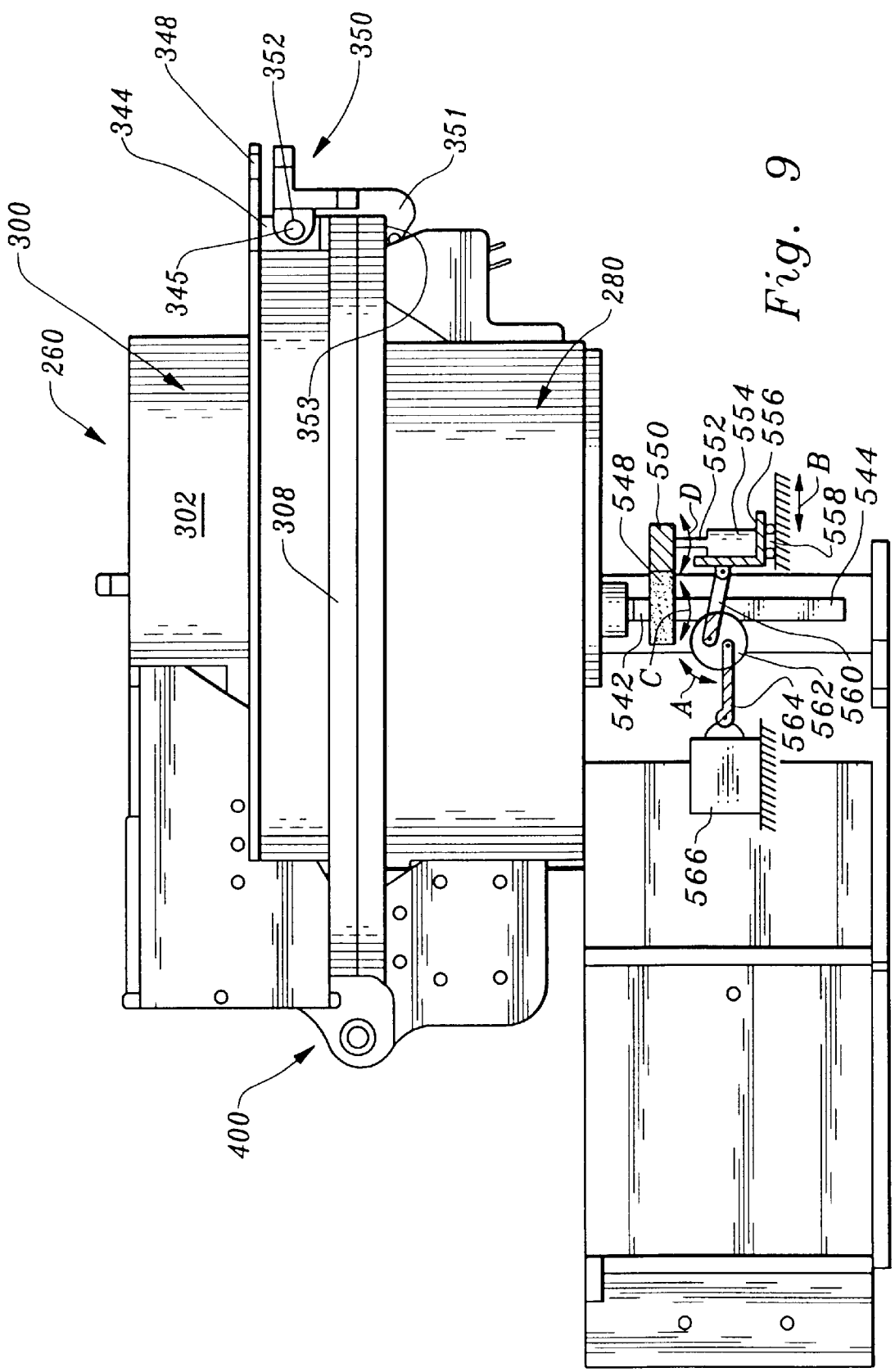
FIG. 9 is a left plane view of the microwave containment chamber, the magnetron and a sample rotation module according to the instant invention.

Referring to FIGS. 8 and 9, a right plane view of the containment chamber is shown with the latch means 340 securing the upper chamber 300 to the lower chamber 280. The latch is comprised of a stationary member 342 and a pivotable member 350. The stationary member 342 is substantially L shaped and includes a vertical member 344 extending up from the upper sealing flange 308 and transitioning into a horizontally extending member 348 which extends away from the cylindrical side wall 302 of the upper chamber 300. The stationary member 342 is provided with a pivot pin 345 in which the pivotable member 350 rotates thereabout for unlatching the upper chamber 300 from the lower chamber 280 thereby allowing the upper chamber to be moved from a substantially horizontal position to an upward vertical position. The pivotable member 350 is substantially J shaped and includes a pivot hole 352 operatively couple to the pivot pin 345. In a closed position, the J shaped member is rotated counter-clockwise such that an innerside of the tip 351 of the J shaped member is received on an underside 353 of the lower sealing flange 292 for locking the upper chamber to the lower chamber. Note that the outer side of the tip 351 of the J shaped member interacts with on/off lever of at least the micro-switch 370 thereby closing the micro-switch and allowing power to be transferred to the power control module 122.

Figure 10:
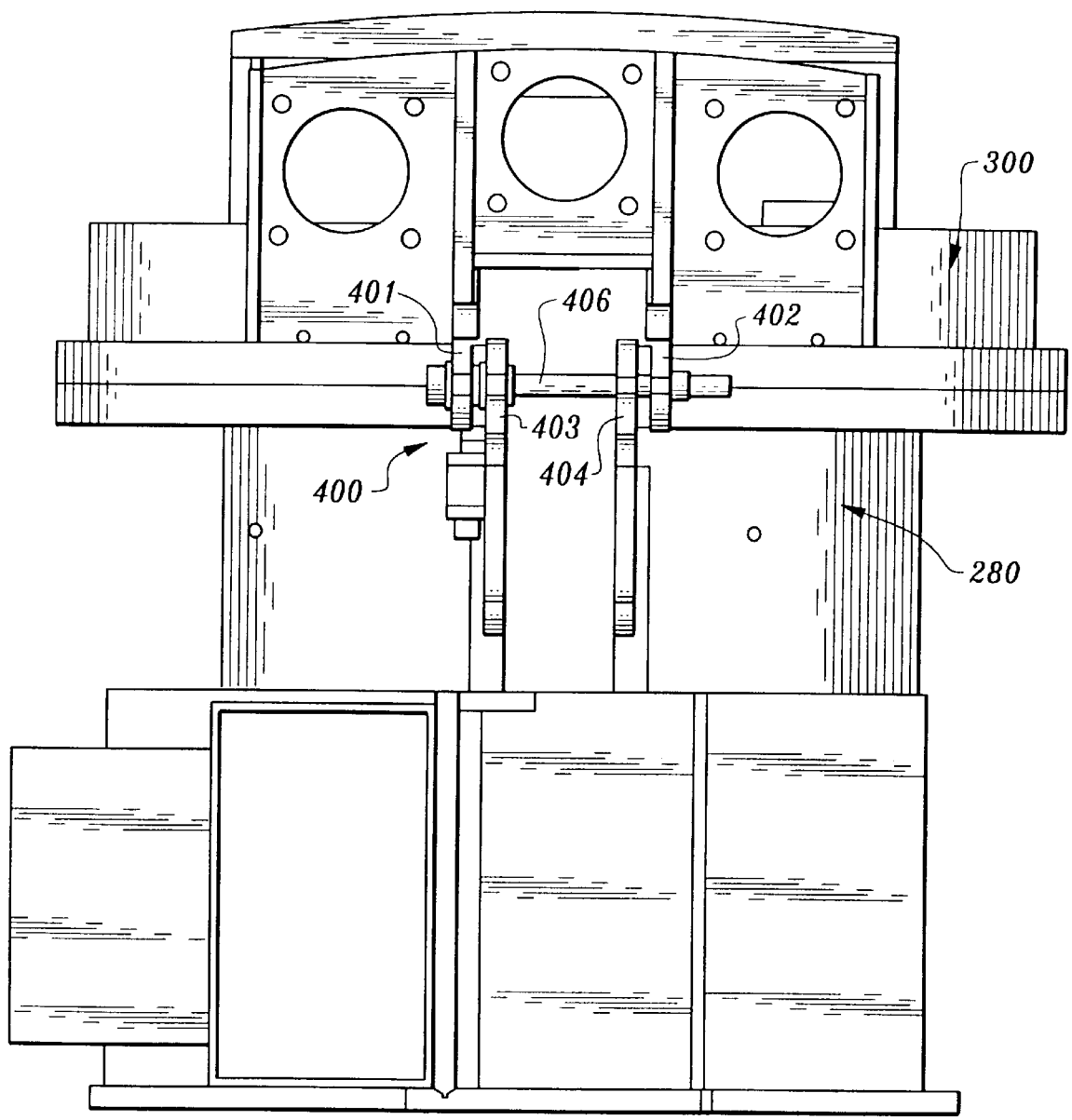
FIG. 10 is a back plane view of the microwave containment chamber, the magnetron and the wave guide.

Referring to FIGS. 8, 9 and 10, the upper chamber 300 is rigidly coupled to the lower chamber 280 via a pivotable hinge 400. The hinge 400 includes a pair of spaced apart upper flanges 401, 402 having holes disposed therein which are in axial alignment. A lower portion of the hinge 400 includes a pair of spaced apart lower flanges 403, 404 which reside within the spaced apart upper flanges 401, 402 of the upper portion of the hinge. The spaced apart flanges 403, 404 include holes which are axially aligned thereby allowing a pin 406 to extend through a first upper flange 401, a first lower flange 403, a second lower flange 404 and then a second upper flange 402 thereby allowing pivotable motion of the upper chamber 300 with respect to the lower chamber 280. The outer upper flanges of the hinge include outer lower surfaces which contact with an on/off lever 391 of at least the one micro-switch 371 for providing redundant protection from the magnetron being engaged prior to the sealing of the upper chamber with the lower chamber.

Referring to FIGS. 10 and 11, the upper chamber 300 includes a moisture evacuation chamber 311 disposed on top of the upper cylindrical wall 302 defining the microwave containment cavity of the upper chamber. The top plate 312 of the upper chamber is perforated in a manner which allows moisture to pass therethrough without the exhausting of microwaves. The moisture is aspirated by a plurality of fans 328, 330 and 332 disposed on a back wall 326 of each of the three evacuation channels defined by a pair of out channel walls 318, 324 and a pair of inner channel walls 320, 322 as shown in FIG. 11. Preferably, the fans are on continuously during moisture volatilization. A dome shaped lid 334 covers the perforated top plate 312 of the upper chamber 300 and the evacuation channels wherein the fans are disposed.

The fans 328, 330 and 332 can be operatively coupled to the power control module or to the central processing unit for delivering power to the fans either in a direct or controlled manner.

Figure 12:
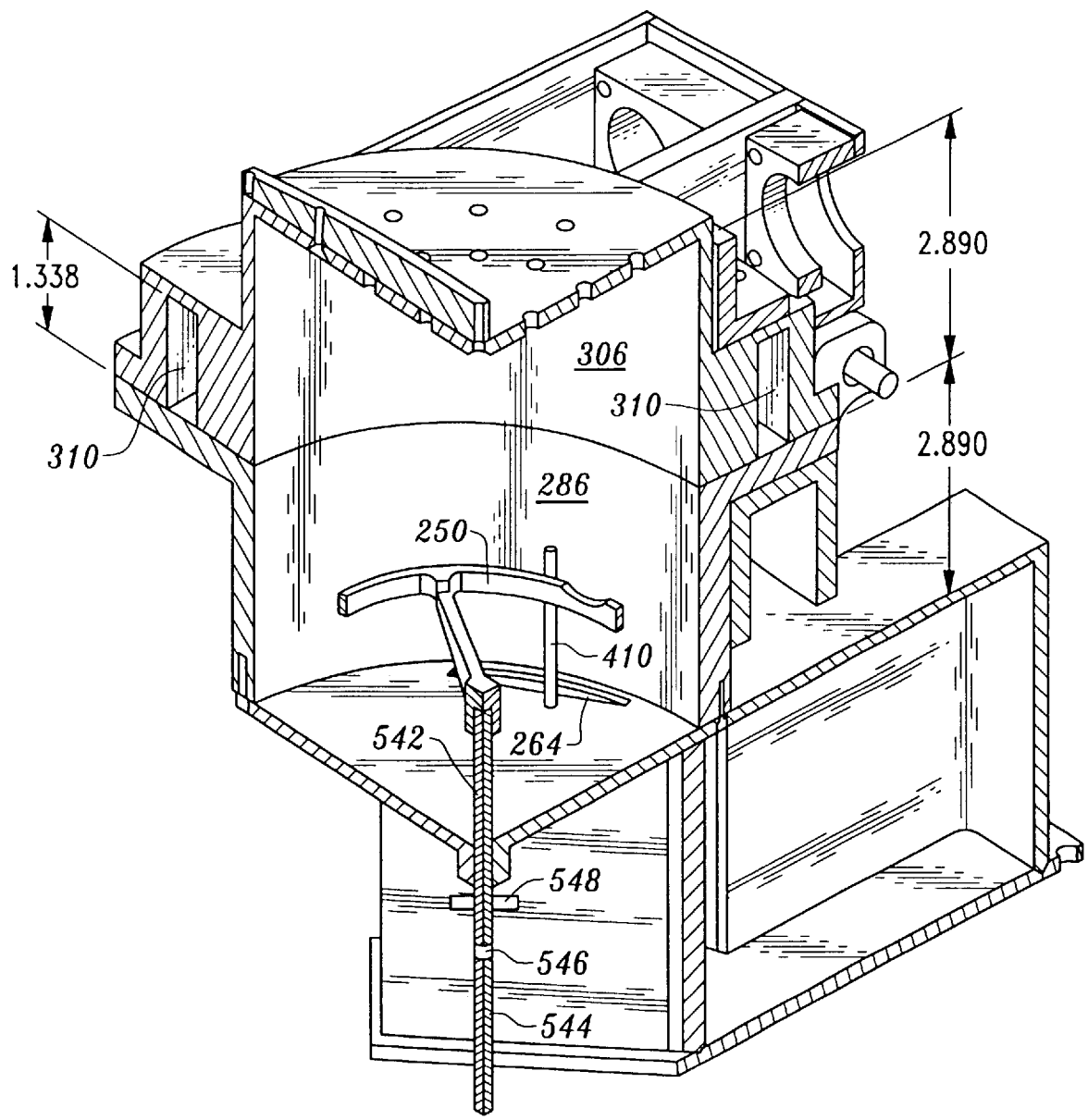
FIG. 12 is a cut-away view of the microwave containment chamber according to the instant invention.

Referring to FIG. 12, a cut-away view of the microwave containment chamber in a closed position is shown thereby revealing the microwave choke channel 310 disposed in the upper sealing flange of the upper chamber and having a height of 1.338 inches. The choke geometry traps and reflects microwave energy at ¼ wavelength to cancel the effectiveness of the energy. The choke channel 310 is a re-active choke system which presents a short-circuit impedance between the sealing flanges of the chamber 260 even if they are slightly separated or misaligned. In addition, the cut-away view reveals a first tuning rod 410 and portal wherein the tuning rod extends from the base plate across the portal opening and into the cylindrical side wall defining the lower chamber of the microwave containment chamber. In addition, a cut-away view of the carriage for supporting a sample is shown wherein the carriage 250 is operatively coupled to the weighing rod 242 extending through the centralized bore 268 of the base 262 of the lower microwave containment chamber 280.

Figure 13:
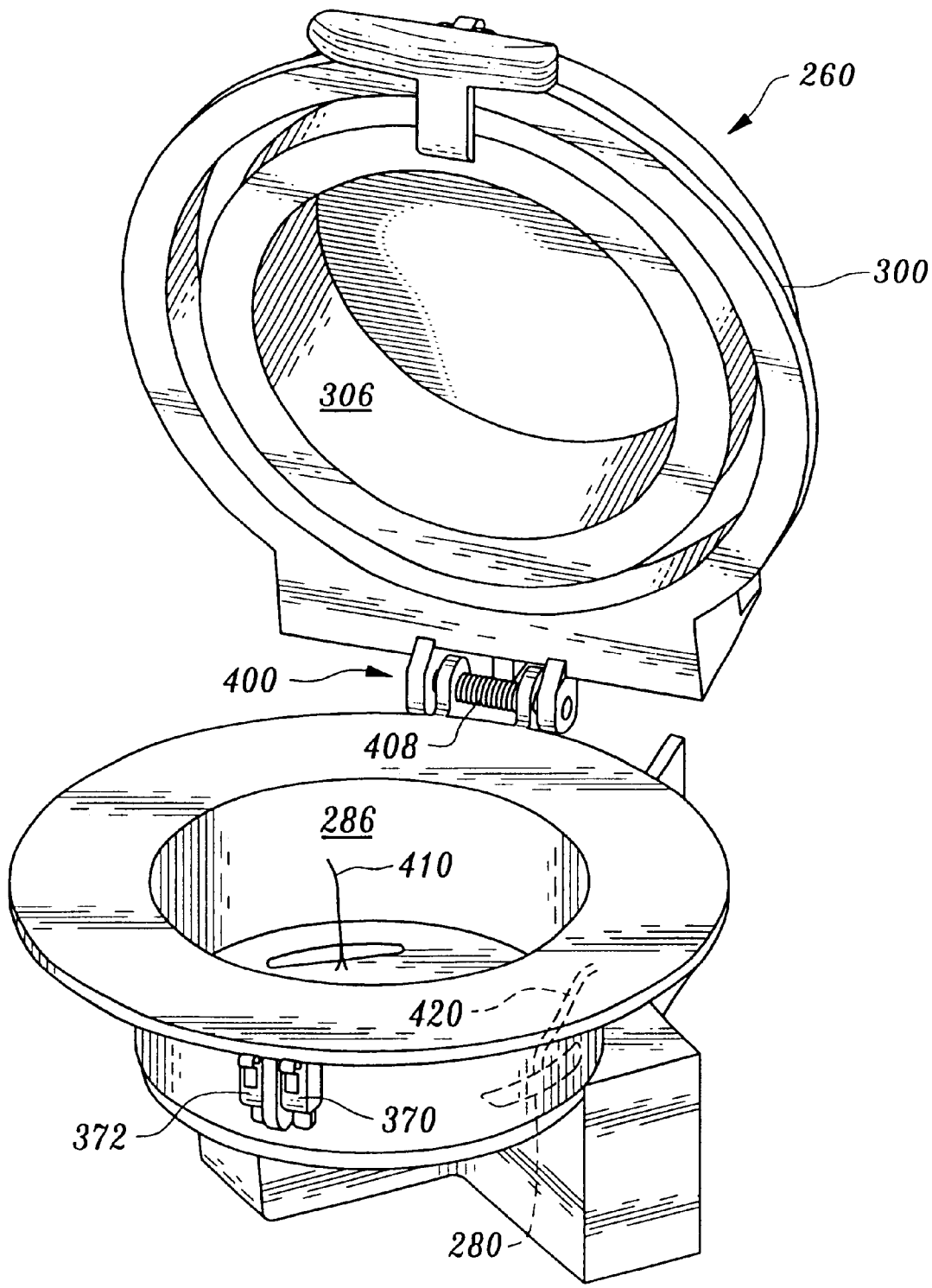
FIG. 13 is a front side elevational view of the microwave containment chamber in an open position and revealing a pair of tuning rods.

Referring to FIG. 13, the microwave containment chamber 260 is shown in an opened position thus revealing the spring bias means 408 coupled to the hinge 400 rigidly attaching the upper microwave chamber 300 with the lower microwave chamber 280 and providing means for retaining the upper microwave chamber in an opened position for ease of loading a sample onto the carriage 250. The interior cylindrical wall 306 of the upper chamber has a height of 2.890 inches and an interior diameter of 6.340 inches. The annulus choke channel 310 circumscribing the cylindrical wall of the interior of the upper chamber is spaced therefrom and has an inner diameter of 8.023 inches and an outer diameter of 8.887 inches thereby defining the choke channel 310 having a circular width of 0.864 inches and a height of 1.338 inches. The interior cylindrical wall 286 of the bottom chamber 280 has a diameter of 6.340 inches which is the same diameter of the interior cylindrical wall 306 of the upper chamber 300. The height of the interior cylindrical wall 286 of the lower chamber 280 is 2.890 inches which is also equal to the height of the interior wall 306 of the upper chamber 300. FIG. 13 also reveals a pair of tuning rods disposed substantially in quadrature specifically, separated by 93.4 degrees. The tuning rods 410, 420 will be delineated in detail infra. Furthermore, note that two micro-switches 370, 372 are provided to interact with the latch 340 for securing the upper chamber 300 to the lower chamber 280.

Figure 14:
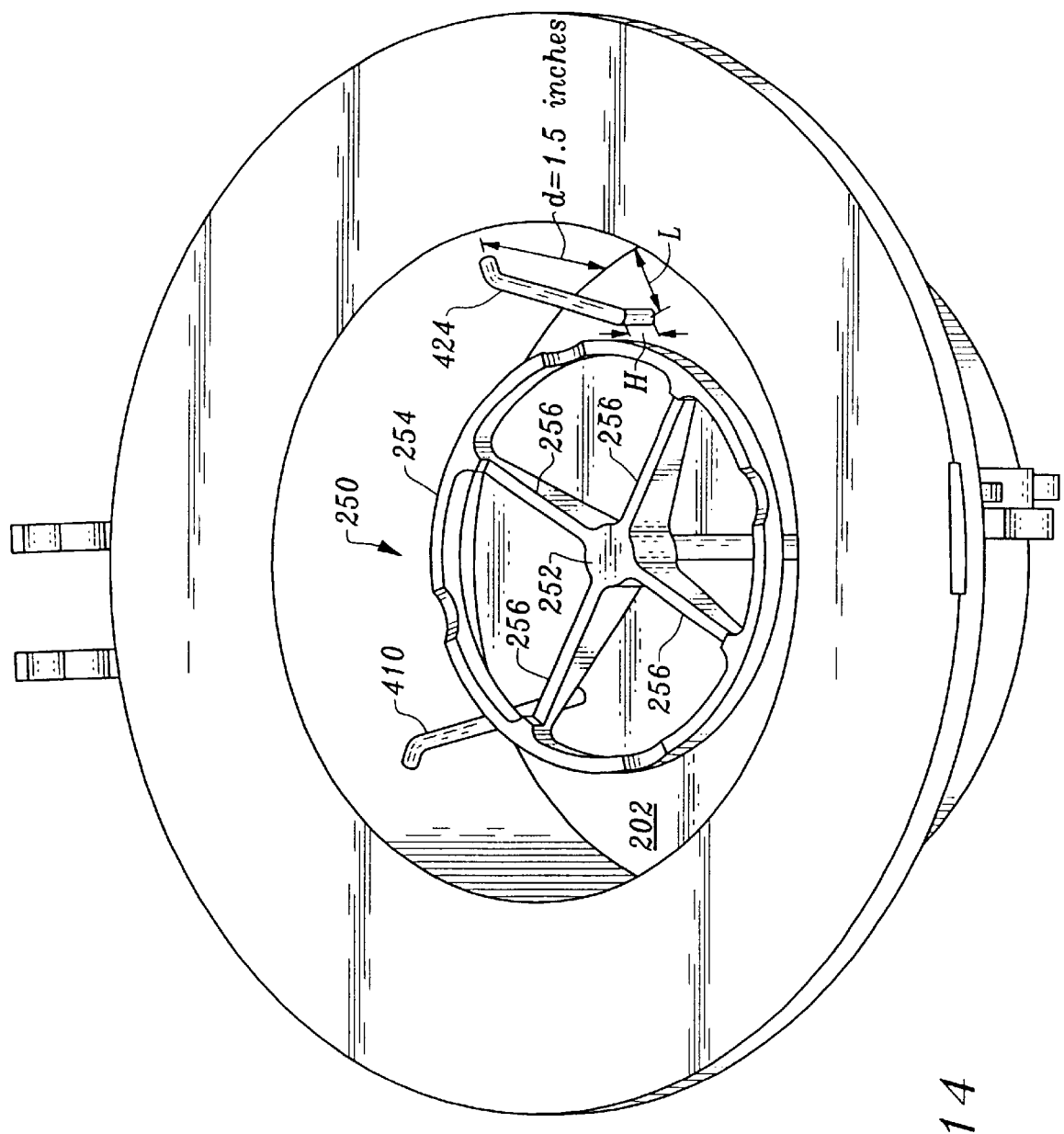
FIG. 14 is a top elevational view of the lower microwave chamber showing the carriage operatively coupled to a wave rod and tuning rods disposed within a lower base plate and a cylindrical side wall.
Figure 15:
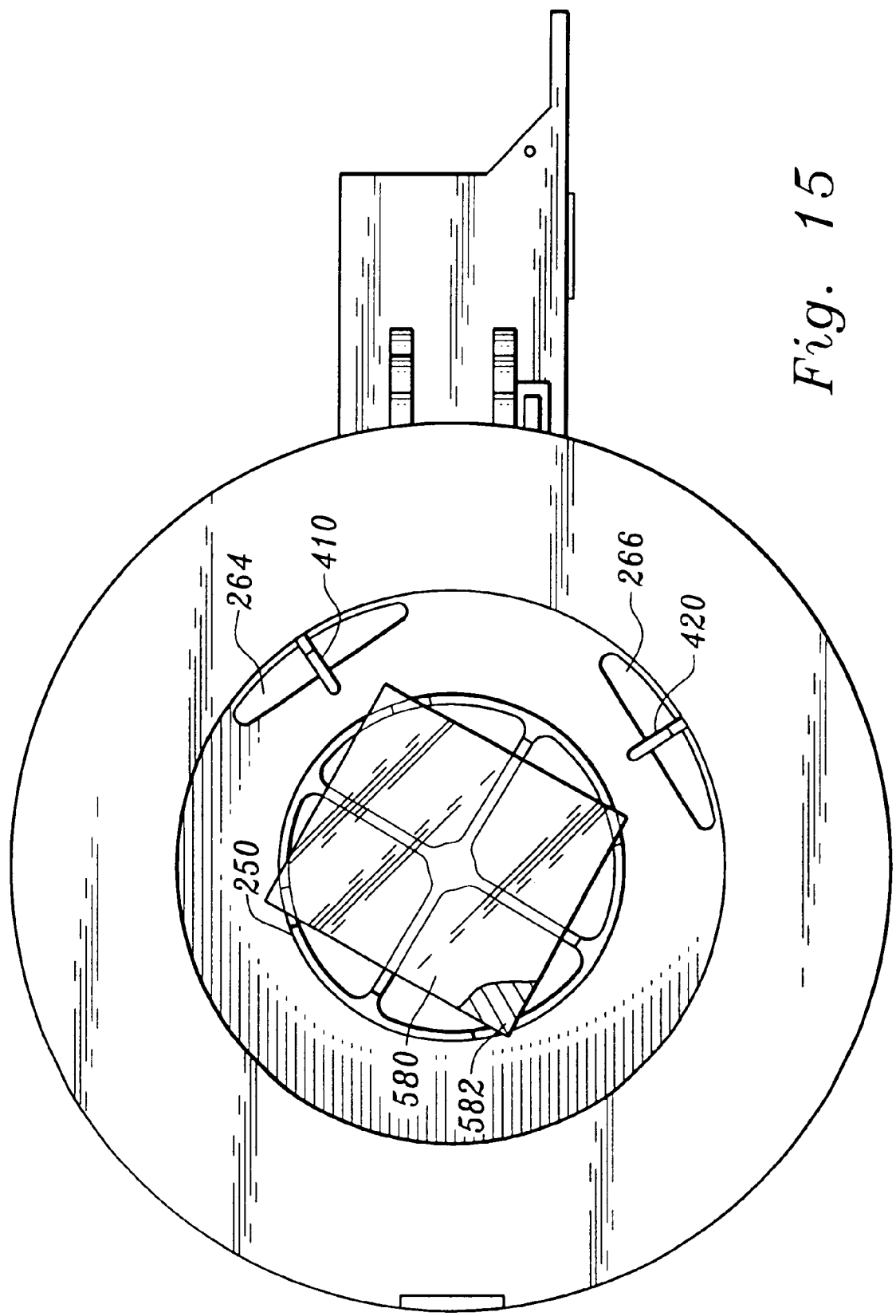
FIG. 15 is a top plane view of the lower microwave chamber showing the tuning rods traversing a pair of portals.
Figure 16A:
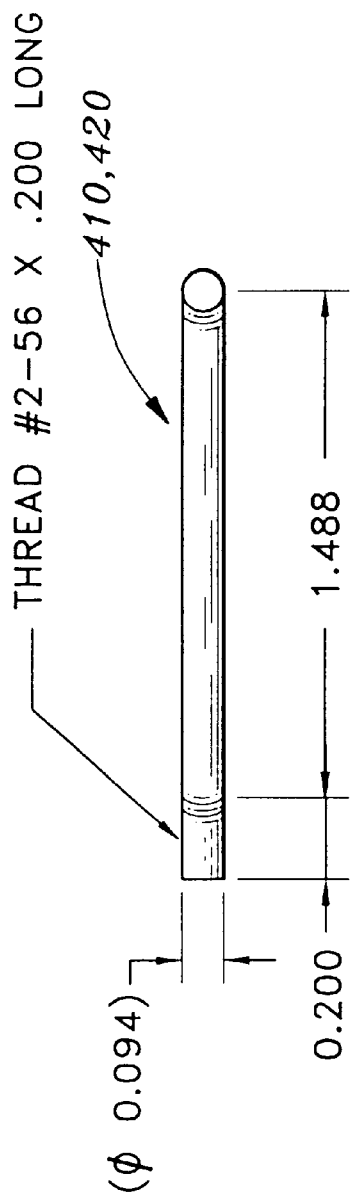
FIG. 16a is a detailed front plane view of a tuning rod according to the instant invention.
Figure 16B:
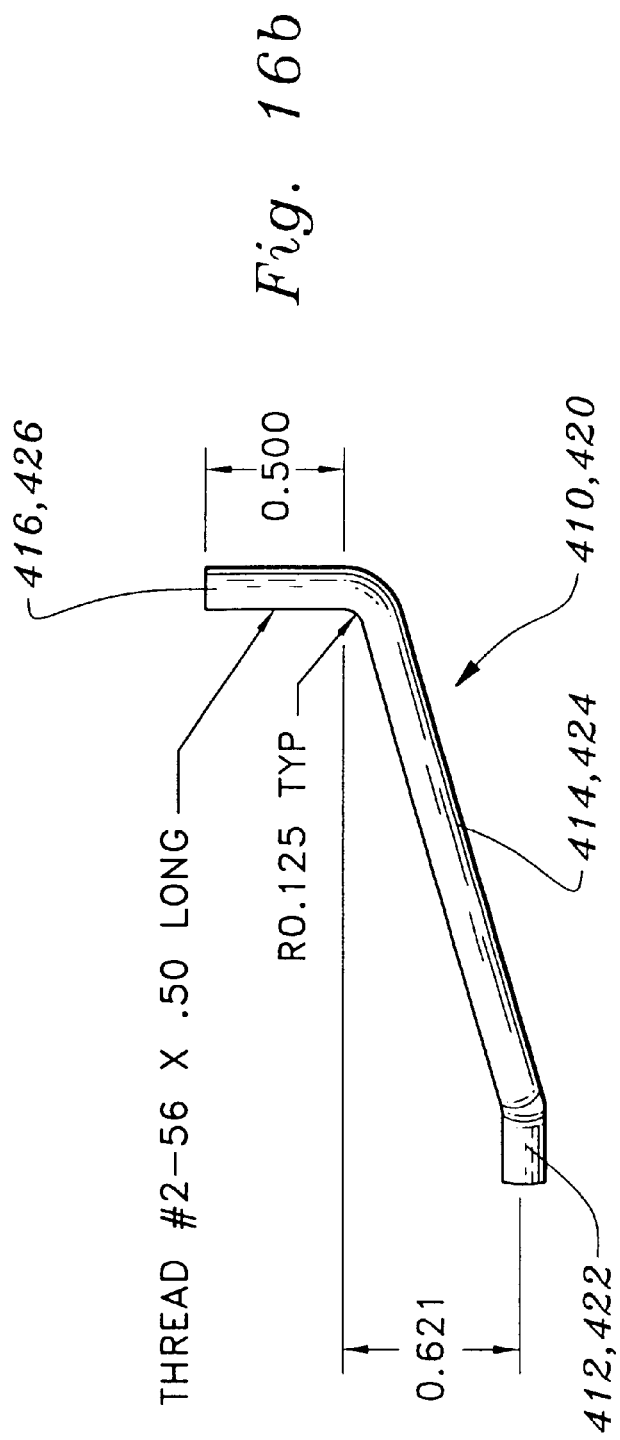
FIG. 16b is a detailed side plane view of a tuning rod according to the instant invention.

Referring to FIGS. 14 and 15, the carriage 250 is configured as a spoked shaped wheel having a central hub 252, a plurality of spokes 256 and an outer rim 254 wherein the central hub transitions into preferably four equally spaced apart spokes 256 terminating into the substantially circular outer rim 254. The outer rim 254 is provided with a plurality of notches 258 off set from the spokes and preferably equally spaced one from another. The hub 252 of the carriage includes a blind bore which couples to the weighing rod 242 extending through the base 262 of the lower chamber 282. In addition, and referring to FIGS. 14, 16a and 16b, the tuning rods 410, 420 are shown to be disposed in the base plate of the lower chamber at a distance distal from the interior cylindrical wall thereof. The tuning rods each include a first end and a second end. The first ends 412, 422 of the tuning rods are disposed in the base 262 of the lower chamber 282 and then transitions into medial portions 414, 424 which are angled toward the interior side wall of the lower chamber wherein the tuning rods terminate into substantially horizontal ends 416, 426 which are received in apertures disposed in the cylindrical side wall of the lower chamber. Note that each tuning rod has a height H in which it vertically extends from the base before transitioning into its medial portion which angles toward the cylindrical lower interior wall of the lower chamber. The tuning rods are toleranced around a nominal diameter. In addition, the tuning rods are spaced a distance L away from the cylindrical interior wall such that the rods 410, 420 straddle the portals 264, 266 respectively.

The tuning rods preferably bisect the portals at a median location wherein the portals are divided into equally spaced sectors. The tuning rods 410, 420 have a diameter of 0.094 inches. As shown, the tuning rods include medial portions 414, 424 with first ends 412, 422 and second ends 416, 426. Each first end has a length of 0.200 inches and the second end of a length of 0.500 inches. The height between the first end and a bend interposed between the medial portion and the second end is equal to 0.621 inches. The length between the second end and the bend interposed between the first end and the medial portion is equal to 1.488 inches. Thus, an angle between the base plate and the tuning rod can be defined as approximately the inverse tangent of the length of the side opposite the angle divided by the height between the first bend and the second bend as shown in the drawing.

Tuning Rod Description

The apparatus 10 has a cylindrical microwave applicator including two control rods. Most microwave applicators (cavities) are of the type "multi-mode", which refers to the amount of different mode patterns that can exist in the cavity for a given frequency. In our application we have two basic modes, one being $TMO_{012}$ and the other being $TM_{111}$. To be able to optimize the heat-distribution it is essential to be able to control the mode balance between the two modes. This is normally practiced by designing the microwave inlet coupling (particular the position) in such a way that desired balance is maintained for some predefined conditions. In this case with the specific modes its not possible to achieve suitable balance with traditional means.

The instant invention includes the use of coupling-hole(s) (irises) or portals between the waveguide(s) and cavity. The basic idea with the tuning rod is to disturb the electric field of mode that is to be suppressed (in this case $TMO_{012}$). This mode has its electric field going in an arc of the total height of the cavity (rotational symmetrical), side wall of the cylinder. By introducing a metal rod semi parallel to the electrical field, one will disturb the mode and with that suppress its existence. The more parallel and the closer to its maximum of the effective to place the control rod in the near field of the inlet-coupling hole or portal than arbitrarily in the cavity. The preferred placement is just in front of the coupling hole on the cavity side of the coupling hole.

Figure 23:
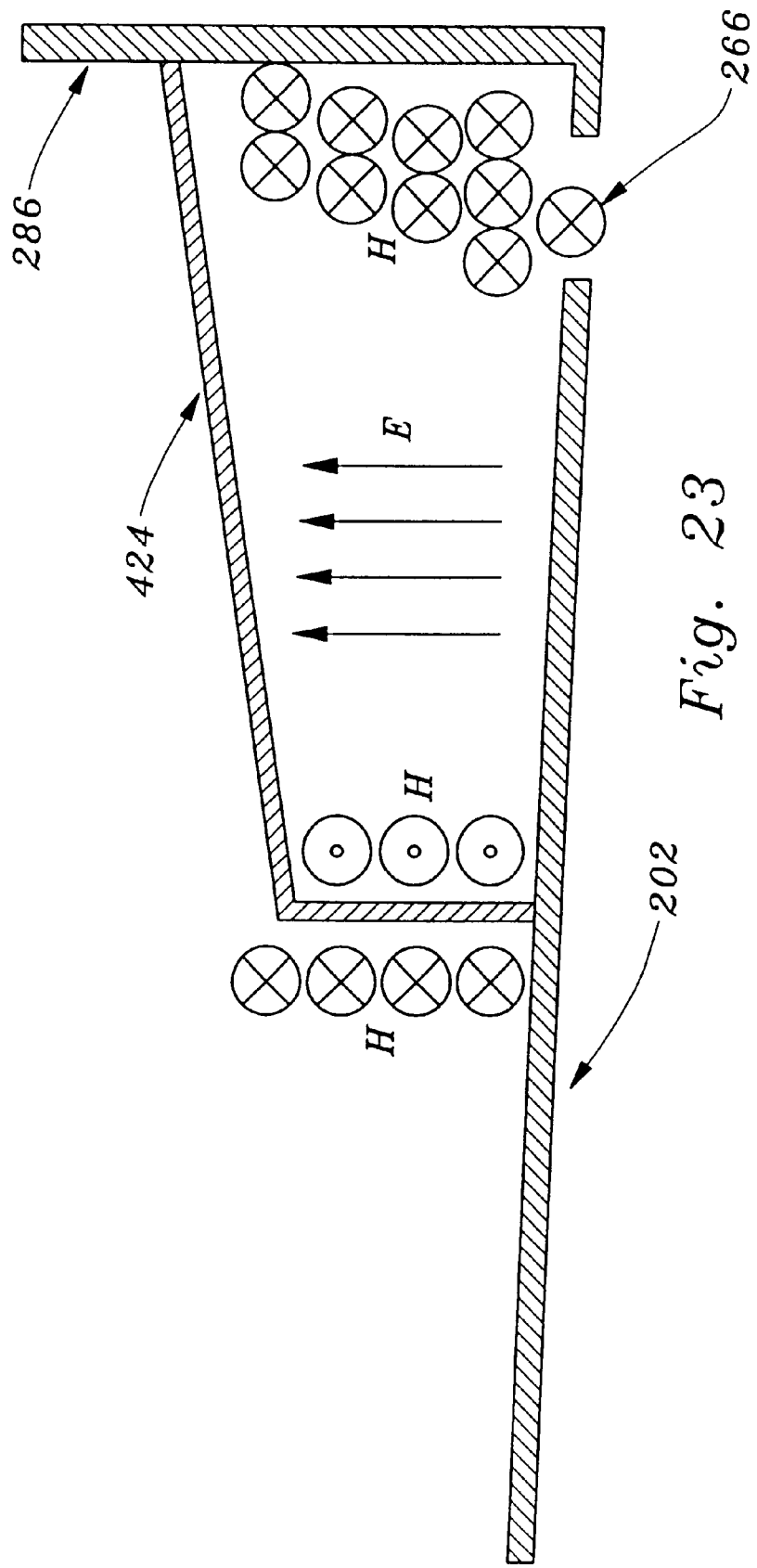
FIG. 23 is a side view of a tuning rod disposed over a portal.

Referring to FIGS. 13 through 17 the tuning rods 410, 420 are between the cylindrical side wall above the coupling slots or portals and the flat circular wall or base some distance inwards radially. The general geometry is shown in FIG. 14, 16a and 16b. There are two perpendicular slots or portals fed in (almost) quadrature. The system in FIG. 23 is doubled.

It has been found that the tuning rods provide a positive action, resulting in a stabilization of the impedance matching of the apparatus 10 (this is crucial, since the load is small).

The Cavity Feed and Possible Modes

The apparatus is supposed to have two resonances: $TM_{111}$ and $TMO_{012}$.

Resonant Action of the Device Structure

One may envision the tuning rod situation by supposing that two oppositely propagating waves from one narrow wall to the other interface in such a way that maximum field strength is obtained with minimum energy input—which is a very suitable way of defining resonance here.

What does the resonance result in?—The simplest answer is that a maximum part of the available power flow is "converted" to the resonant filed pattern; when this happens there will be less impinging power left so that the resonance will be self-limiting in amplitude. Generally, there will be an almost full nulling of one impinging filed component by the resonant field. This situation is shown in FIG. 23.

In effect, the incoming H field from each slot or portal will create a resonance (if the device dimensions are right) which will weaken the total H field at the wall in the region. Instead, there will be a strong H field around (and particularly outside) the "inner leg" 412, 422 of the device, where there is no strong field without the device.

It is readily seen that the inner leg will act as a quite powerful excitor of a circulating H field, which will go over into a vertical E field upwards. This combination of E and H fields may couple quite well to a H field loop (with accompanying vertical E field) of the $TMz_{11}$ mode. There will thus be a good field matching from the device region (medial portion 414, 424 ) to the desired cavity mode.

The Coupling Between the Cavity and Device Region Resonances

This coupling function can be explained as follows: the coupling factor (in principle: transmission impedance equality) between the resonant device region and the cavity resonance will become quite frequency-sensitive, due to the reasonably high Q value of the device region. If the device region is now chosen to be resonant at a frequency some ten(s) of MHz away from 2460 MHz, the cavity resonance with a changing (i.e. drying) load will move along the resonant curve of the device region.

If the Q value of the cavity is high, its own resonance will dominate and the coupling is good. When the cavity Q value goes down, the coupling will typically be less (since high coupling for a small sample is desirable). However, the overall resonant frequency will change less due to the resonance coupling between the two resonances. Furthermore, the coupling can be made to increase (due to the slope of the device region being active at the "start" of the process), and the impedance matching can be made fairly constant during the whole process.

There are thus several parameters which together determine if the combination of cavity and device region will work well:

The resonant frequency of the cavity resonance without device (and at strong undercoupling), as a function of the load variations.

The Q value of the cavity resonance, and its variation with the specified load variations.

The field matching of a primary (slot) feed to the resonant mode(s) (this contributes to the determination of also the coupling factor).

The field matching of the device region to the cavity mode (this contributes to the determination of also the coupling factor).

The resonant frequency of the device region (under conditions of removed cavity).

The internal Q value of the device region.

The coupling factor from the slot to the cavity resonance, as a function of the load variations.

The coupling factor from the slot to the device region (i.e. how much of the overall coupling is determined by the device region).

Figure 17:
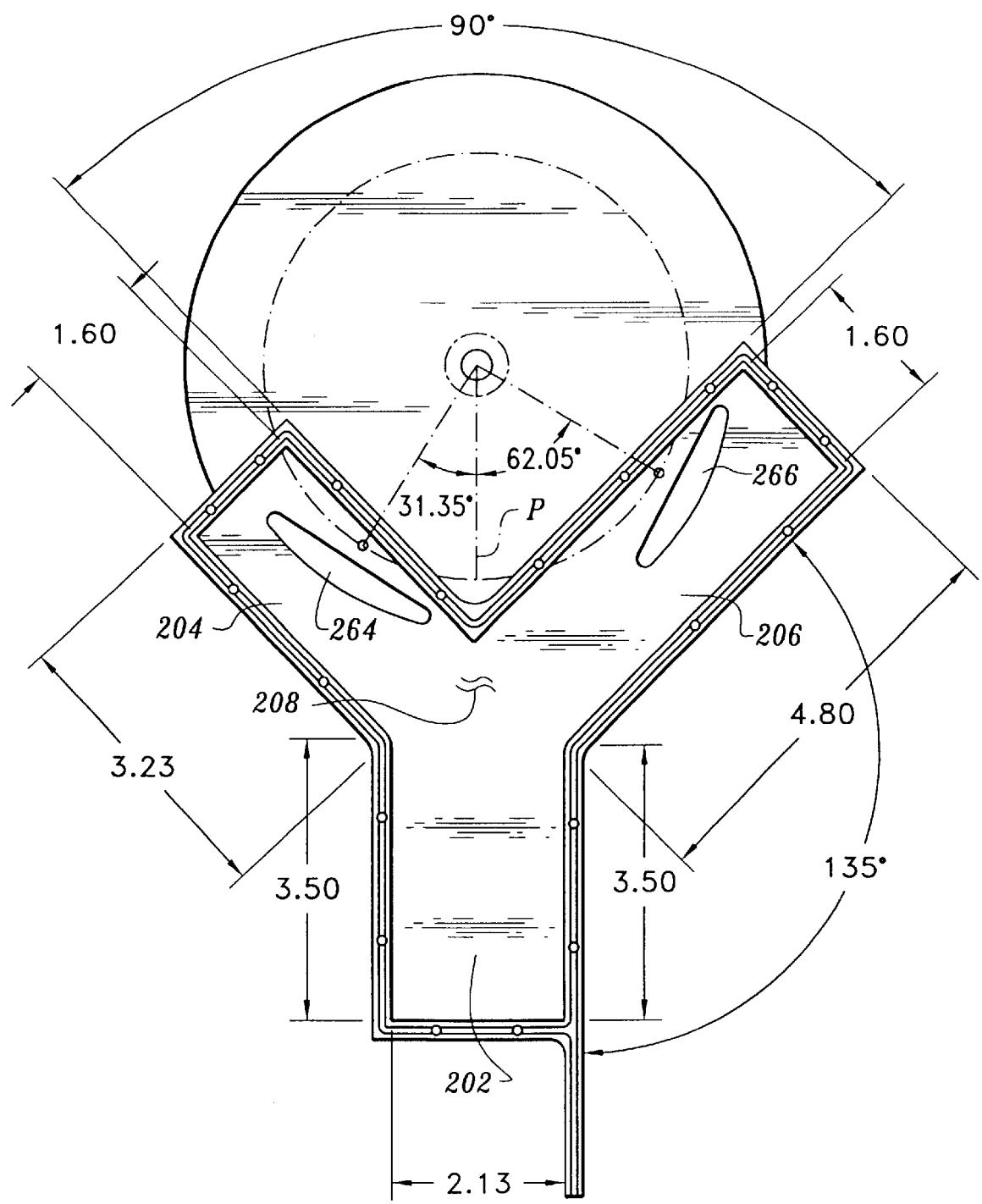
FIG. 17 is a bottom plane view of the microwave containment chamber and the wave guide with important dimensions delineated thereon.
Figure 18:
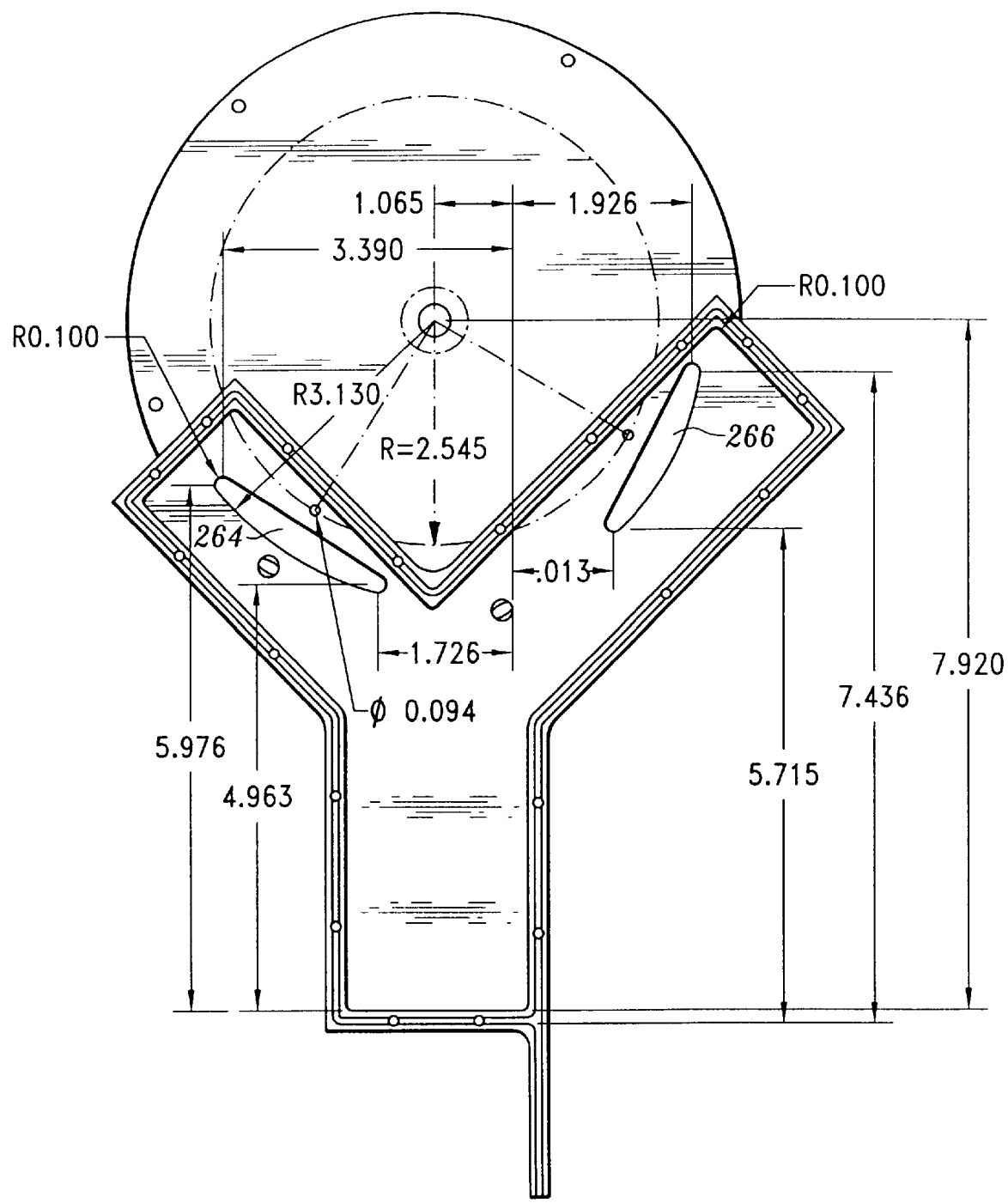
FIG. 18 is a bottom plane view of that which is shown in FIG. 9 with further dimension depicted thereon.

The unique configuration and dimensions of the wave guide will be delineated with the help of FIGS. 17 and 18. The wave guide is substantially Y shaped having a base wave guide 202 which is approximately 3.5 inches in length and 2.13 inches in width, the first wave guide feed 204 having a length of 3.23 inches and a width of 1.6 inches, and the second wave guide feed 206 having a length of 4.8 inches and a width of 1.6 inches. The first and second wave guide feeds 204, 206 bifurcate from the main wave guide at a intermediate junction 208. A splitter can be added at the junction to assist in setting up the phase shift. The first wave guide feed 204 transitions into the first portal 264 disposed in the base 262 of the lower chamber 280 while the second wave guide feed 206 transitions into the second portal 266 disposed in the base plate 262 of the lower chamber 280. The mid-point of the first portal is at a 31.35 degree angle with respect to a plane P bisecting the transitional area of the first wave guide feed and the second wave guide feed. The mid-point of the second portal has an angle of 62.05 degrees with respect to this bisecting plane as is shown in FIG. 17.

Referring to FIG. 18, the portals 264, 266 of the base 262 provide openings for delivery of microwave energy to the sample being assayed and subsequently manipulated for a loss on drying analysis. The portals 264, 266 are substantially canoe shaped openings having radiused bottoms of preferably 3.130 inches away from a mid-point of the centralized bore disposed in the base of the lower chamber. The radiused bottom transitions into radiused corners having a 0.1 inch radius and a chord extending from one radiused edge to the other thereby forming a closed canoe shaped opening.

Figure 19:
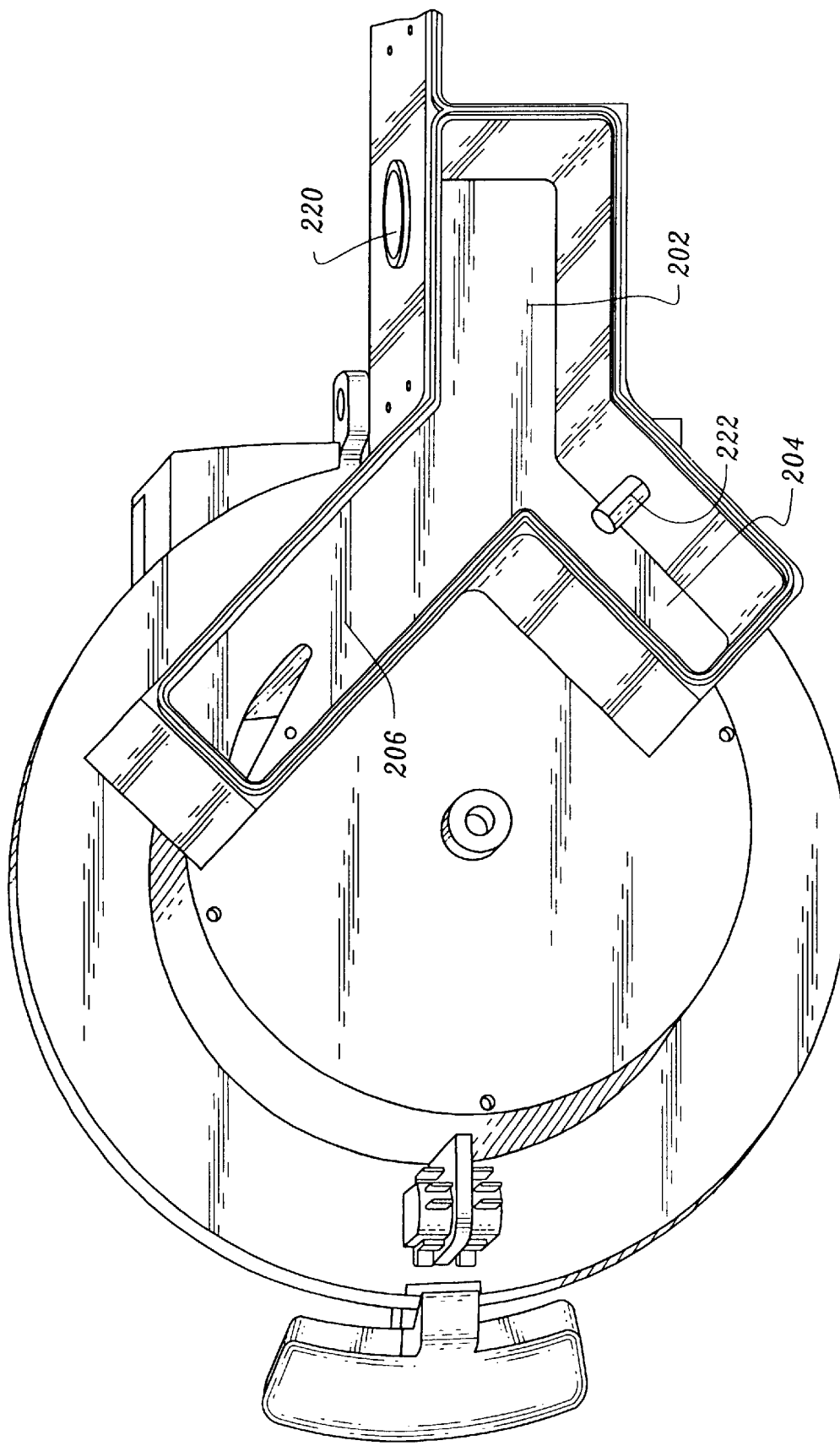
FIG. 19 is a bottom view of the wave guide with a base of the wave guide removed therefrom for showing a tuning stub disposed through an outer peripheral wall of one branch of the wave guide.

Referring to FIG. 19, the magnetron is operatively coupled to an outside wall of the base branch of the quadrature wave guide and communicates with the base branch of the quadrature wave guide via a magnetron antenna hole 220 disposed through a side wall of the base branch of the wave guide. In addition, a tuning stub 222 extends through an outside wall and into the first branch 204 of the wave guide 200 at a location proximate the bifurcation of the wave guide into the first and second branches. The tuning stub 222 is dimensioned to attenuate a third energy mode such that there are only two substantial energy modes being delivered to the chamber. In other words, tuning stub 222 filters out measurably a third mode, assuring only two modes enter chamber at peak efficiency. The third mode used to have a drastic effect of sample position tolerance and uniform drying.

Figure 20A:
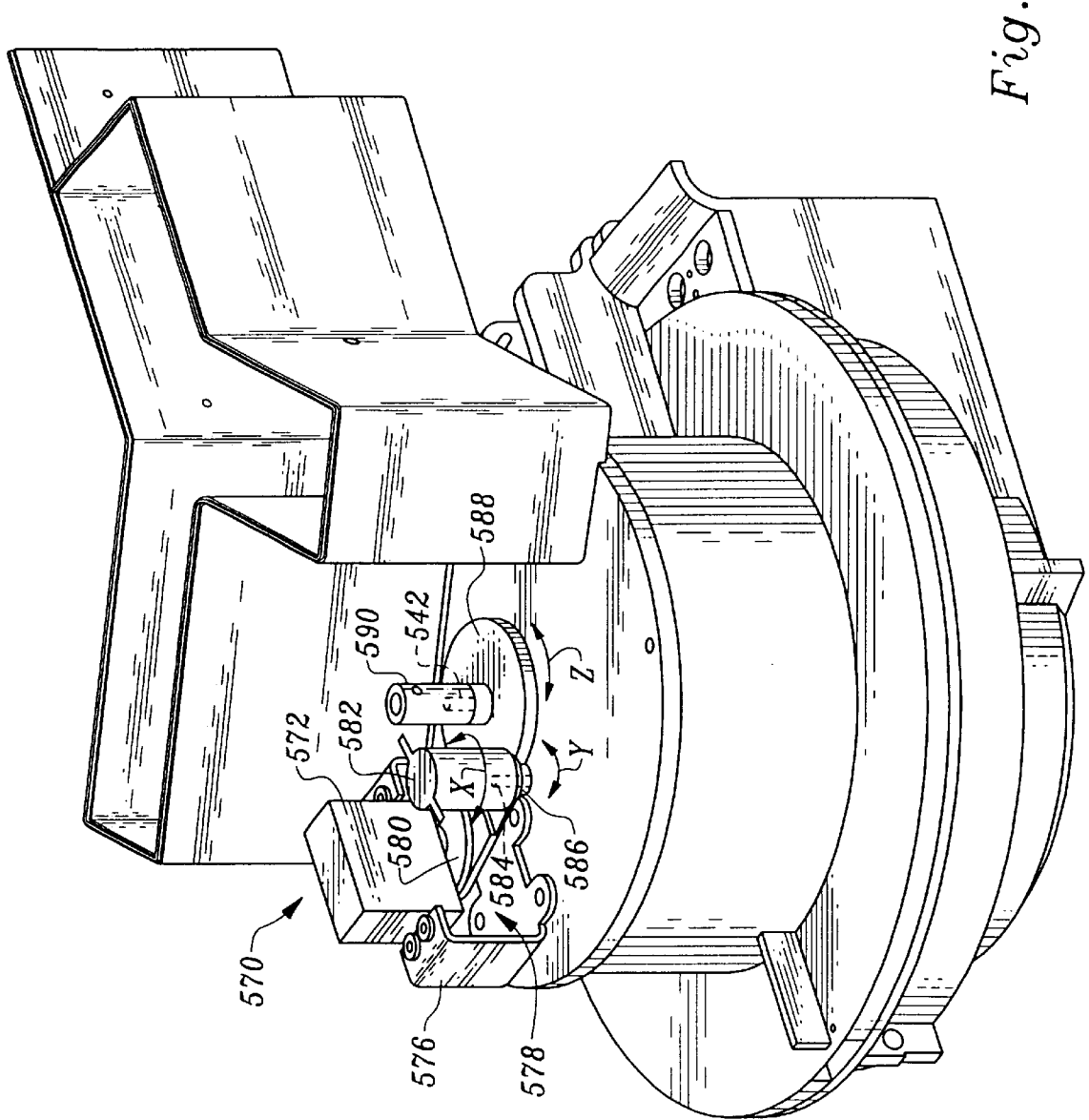
FIG. 20a is an isometric view of a sample rotation module according to the instant invention.
Figure 20B:
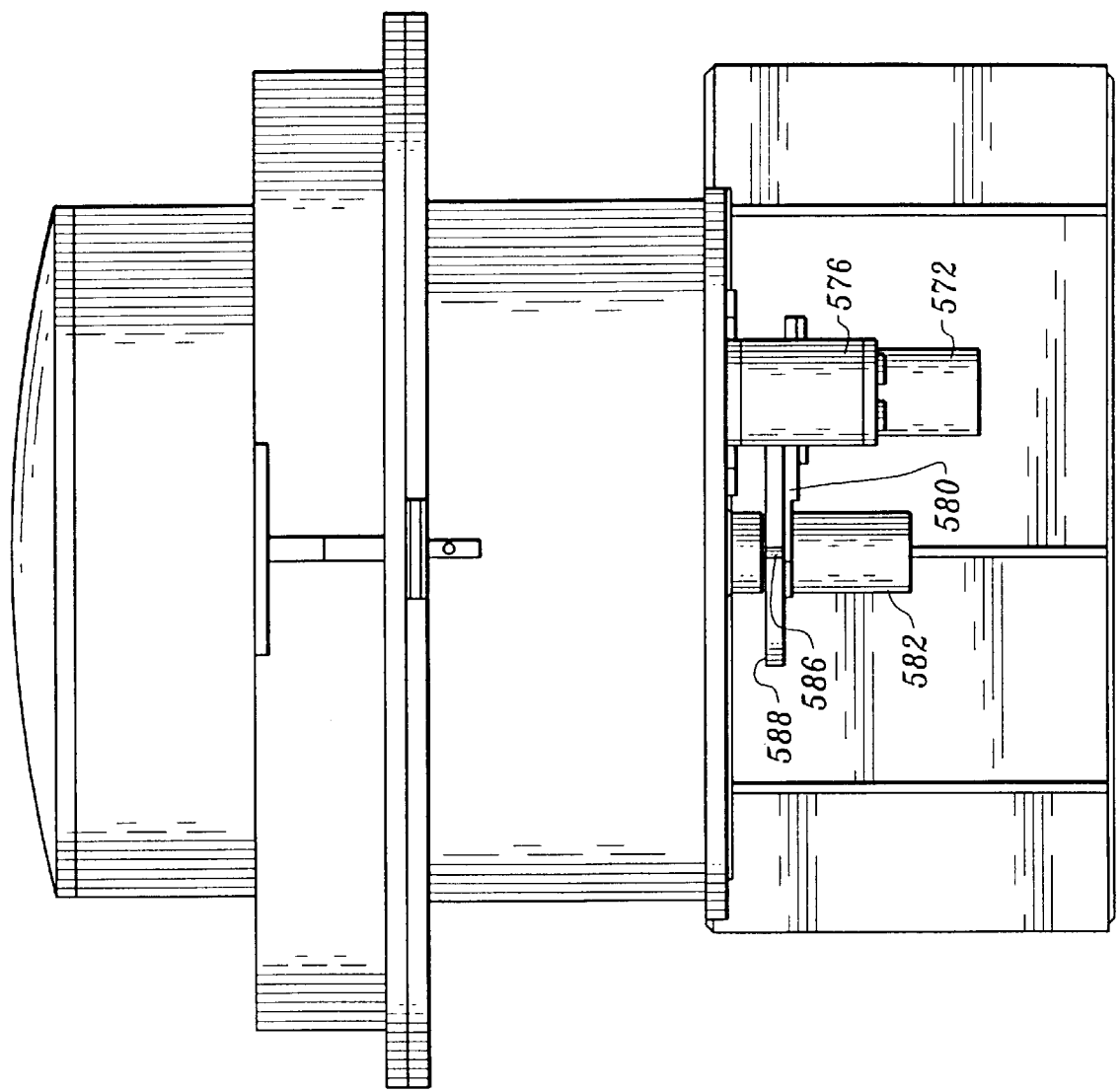

A preferred embodiment of the rotation means 450 is shown as 570 in FIGS. 20a through 20d. Referring to FIG. 20a, rotation means 570 includes an engage/disengage servomotor 572 which is coupled to the bottom of the chamber via a bracket 576. The bracket 576 includes an interior hollow area 578 which allows a shaft 574 of the servomotor 572 to couple to a drive motor 582 via a rotatable platform 580. The drive motor 582 includes a shaft 584 coupled to a drive motor wheel 586. The drive motor wheel 586 coacts with a friction drive wheel 588 which is coupled to the upper member 542 of weighing rod 242 for rotating the carriage 250 and thus the sample. The drive motor 582 preferably has bi-directional capability for clockwise or counterclockwise rotation of the carriage 250 and variable speed control (angular velocity) for variable clockwise or counterclockwise rotative speed of the carriage 250.

The upper member 542 is coupled to the lower member 544 via sleeve 590 wherein the upper member is allowed to turn within the sleeve when the friction drive wheel 588 is rotated.

Figure 20C:
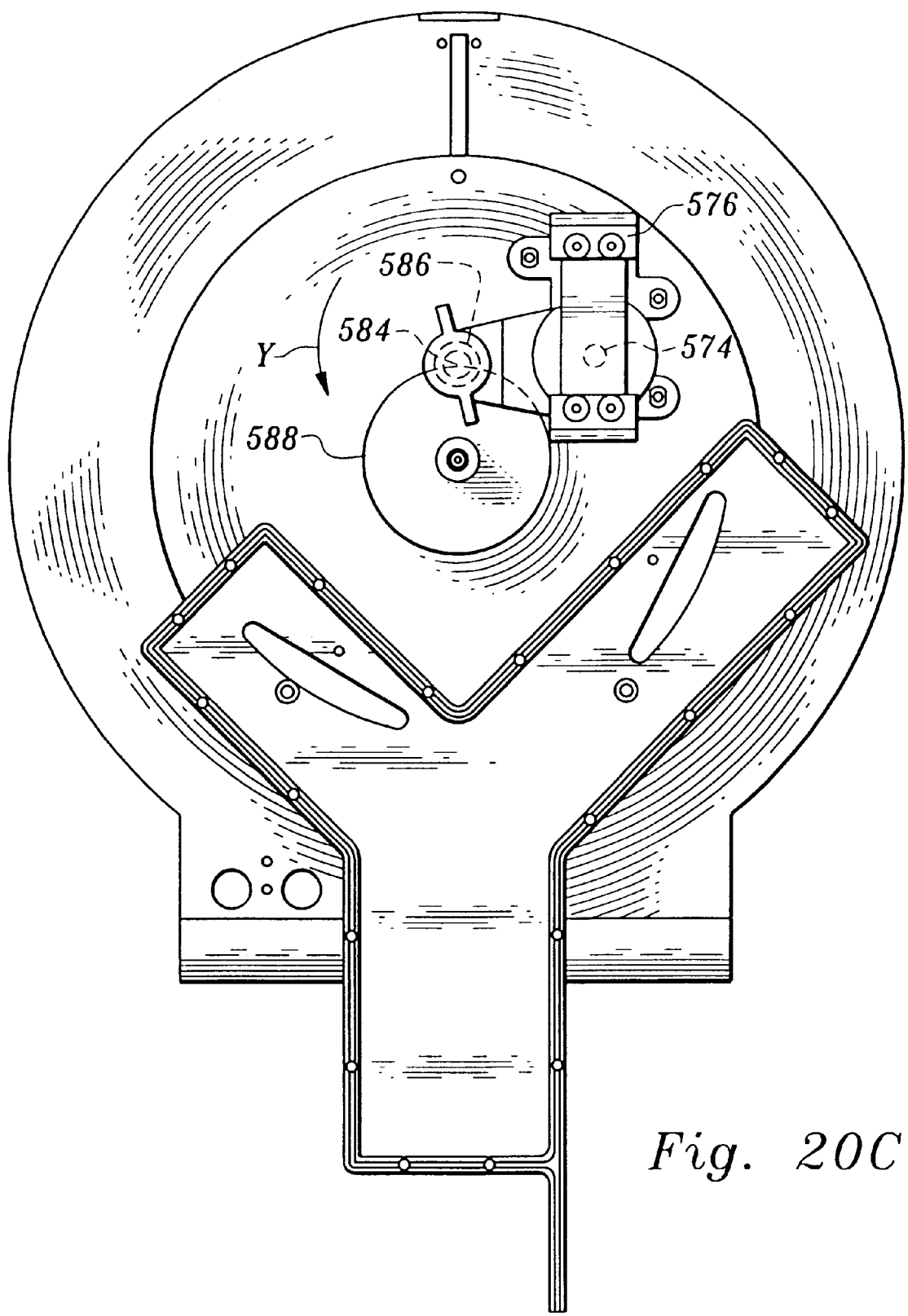
FIGS. 20c and 20d are bottom plane views of that which is shown in FIG. 20a with the sample rotation module shown in an engaged and in a disengaged position respectively.

Referring to FIG. 20a, when the rotation means is actuated the engage/disengage servomotor 572 rotates the drive motor 582 in a clockwise or in a counterclockwise direction along double ended arrow "X". In an engage mode the power control board signals the servomotor 572 to rotate the platform 580 in a counterclockwise direction such that the drive motor wheel 586 contacts the friction drive wheel 588. Simultaneously, the drive motor is activated by the power control board to rotate the drive motor wheel 586 in a clockwise or counterclockwise direction along double ended arrow "Y". Thus, when the motor wheel 586 contacts the friction drive wheel 588 it is rotated in a clockwise or counterclockwise direction along double ended arrow "Z"thereby rotating the carriage 250. FIG. 20c shows the rotation means 570 in an engage position while FIG. 20d shows the rotation means in a disengage position.

Figures 20D, 21:
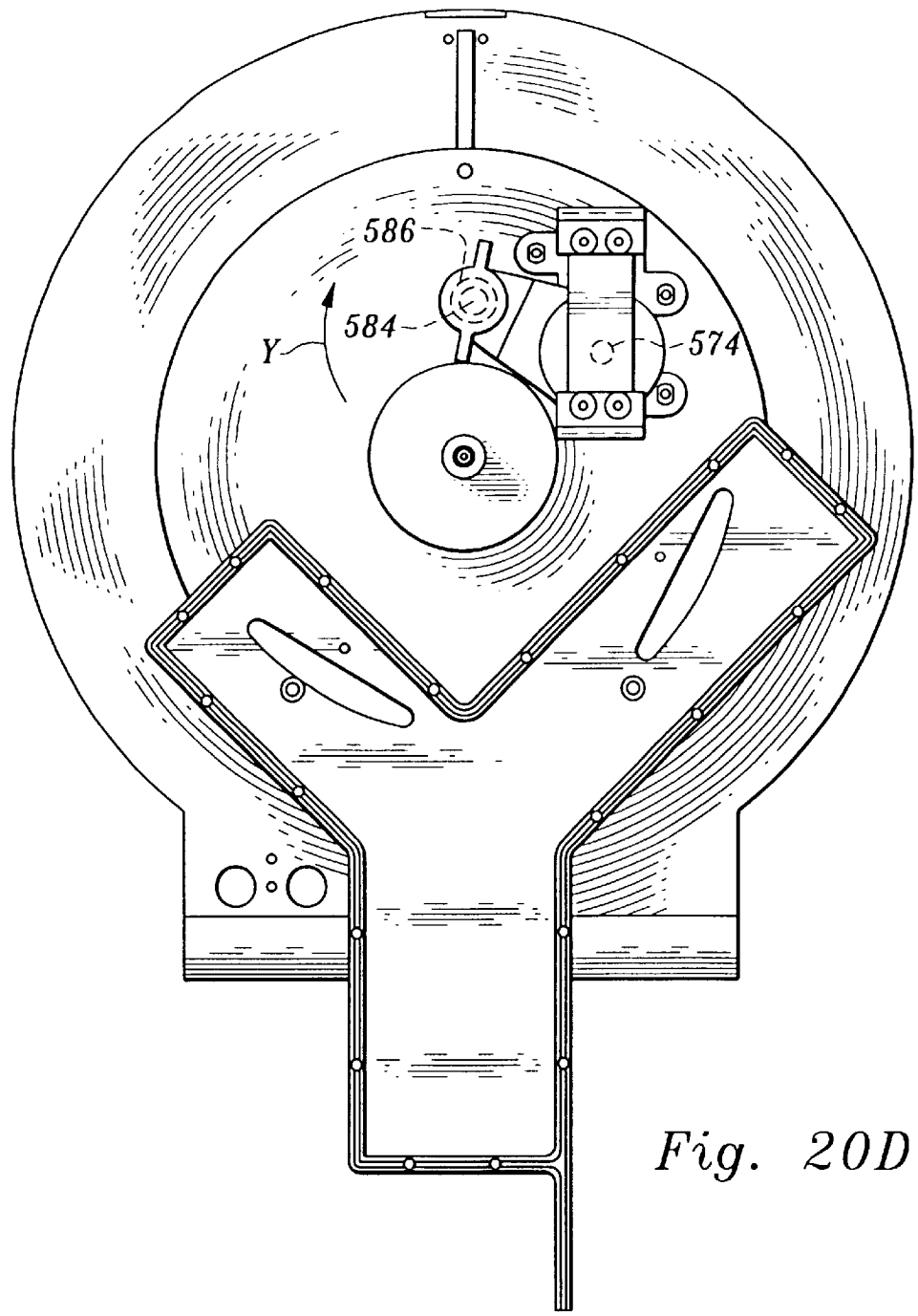
FIG. 21 is a schematic of the power control module shown in FIG. 6.
Figure 21A:
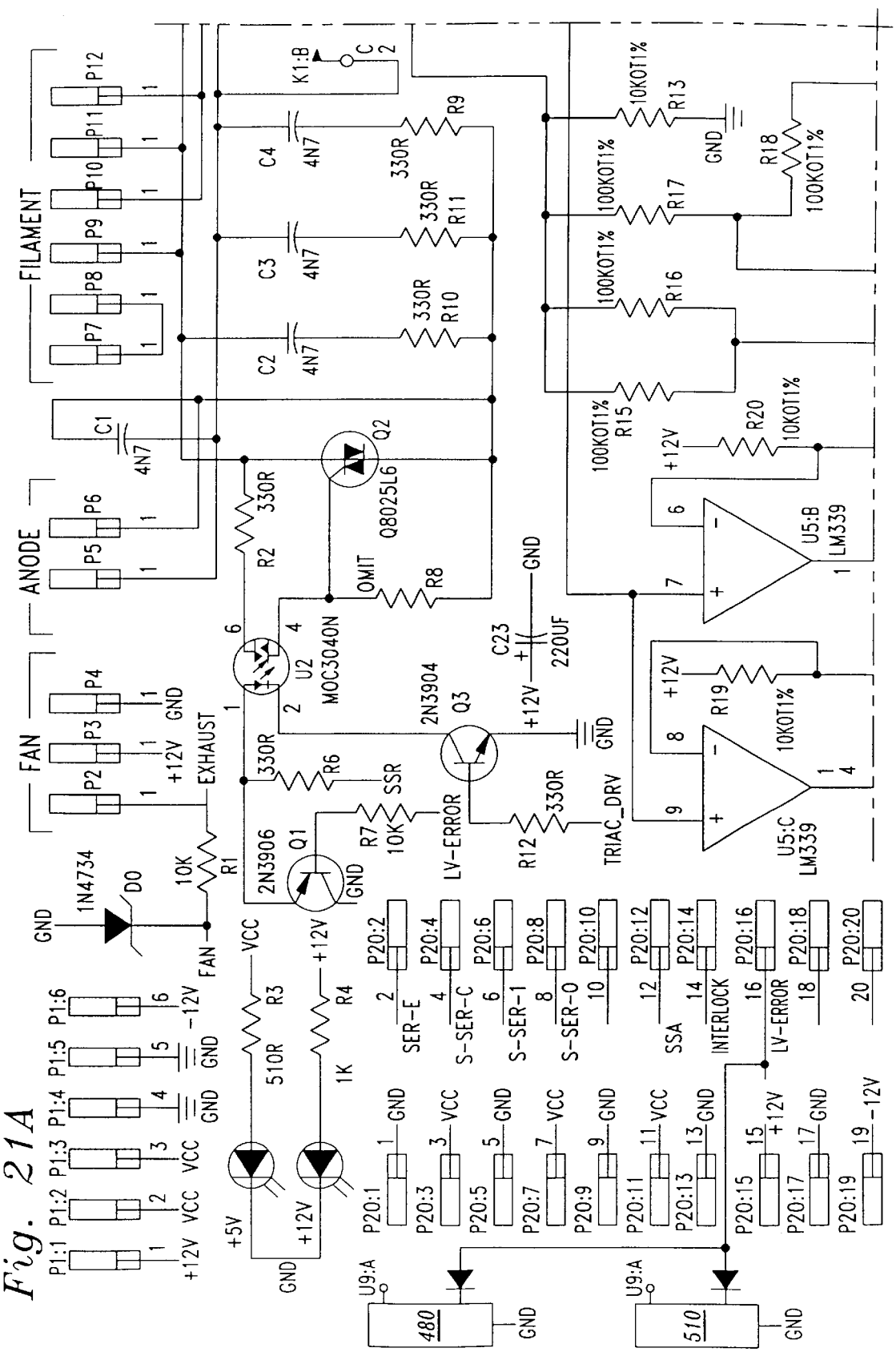
Figure 21B:
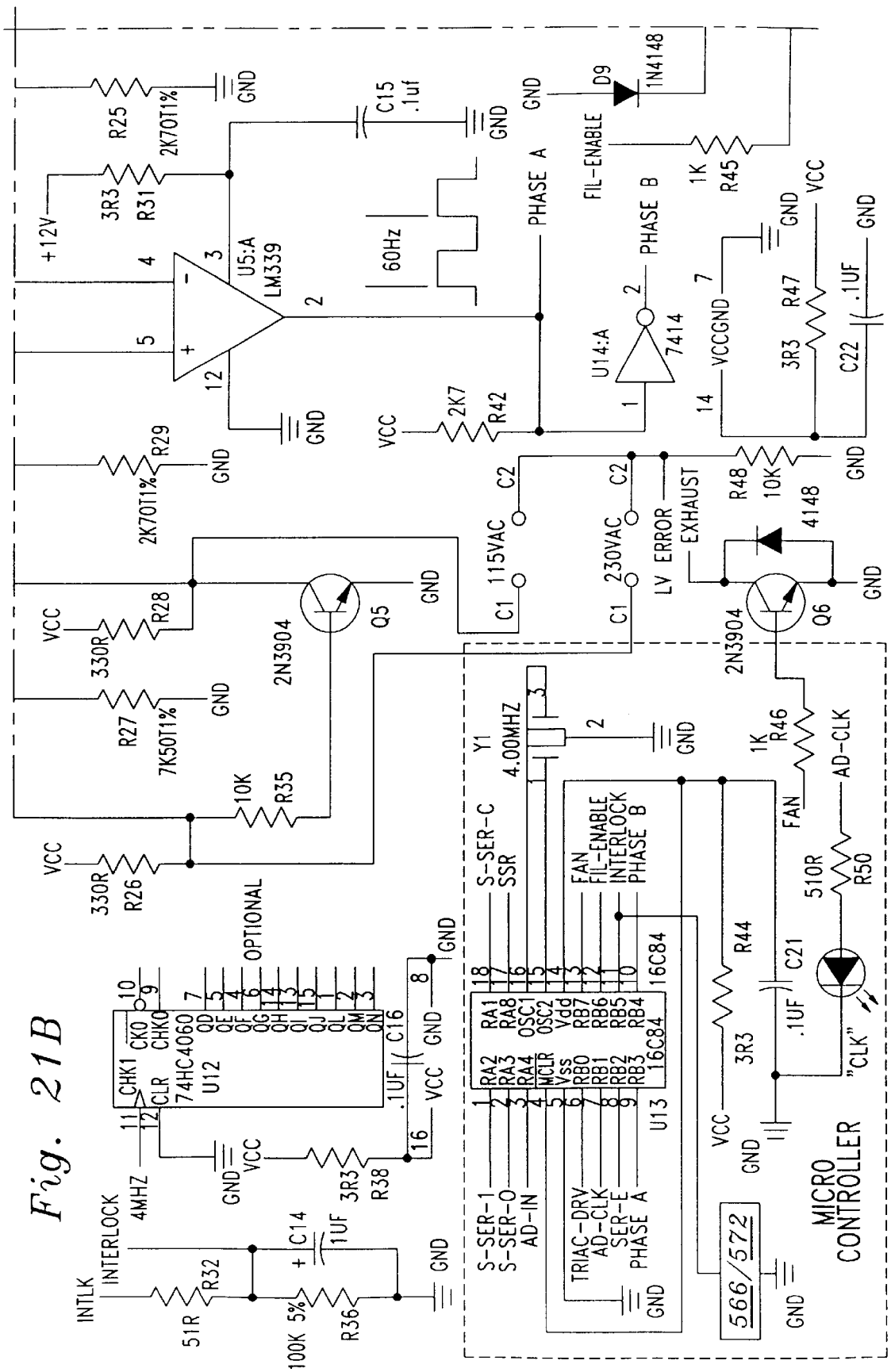
Figure 21C:
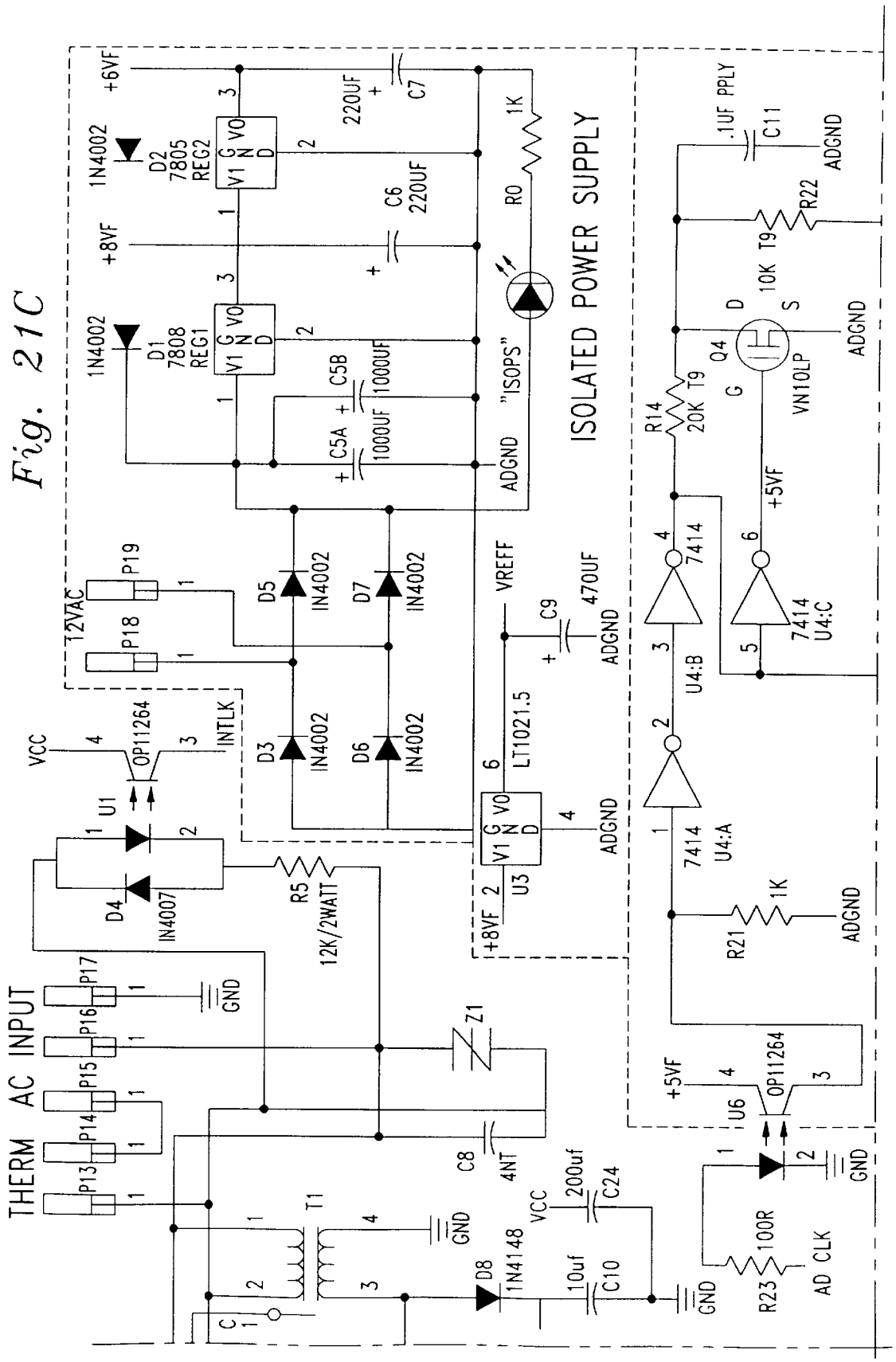
Figure 21D:
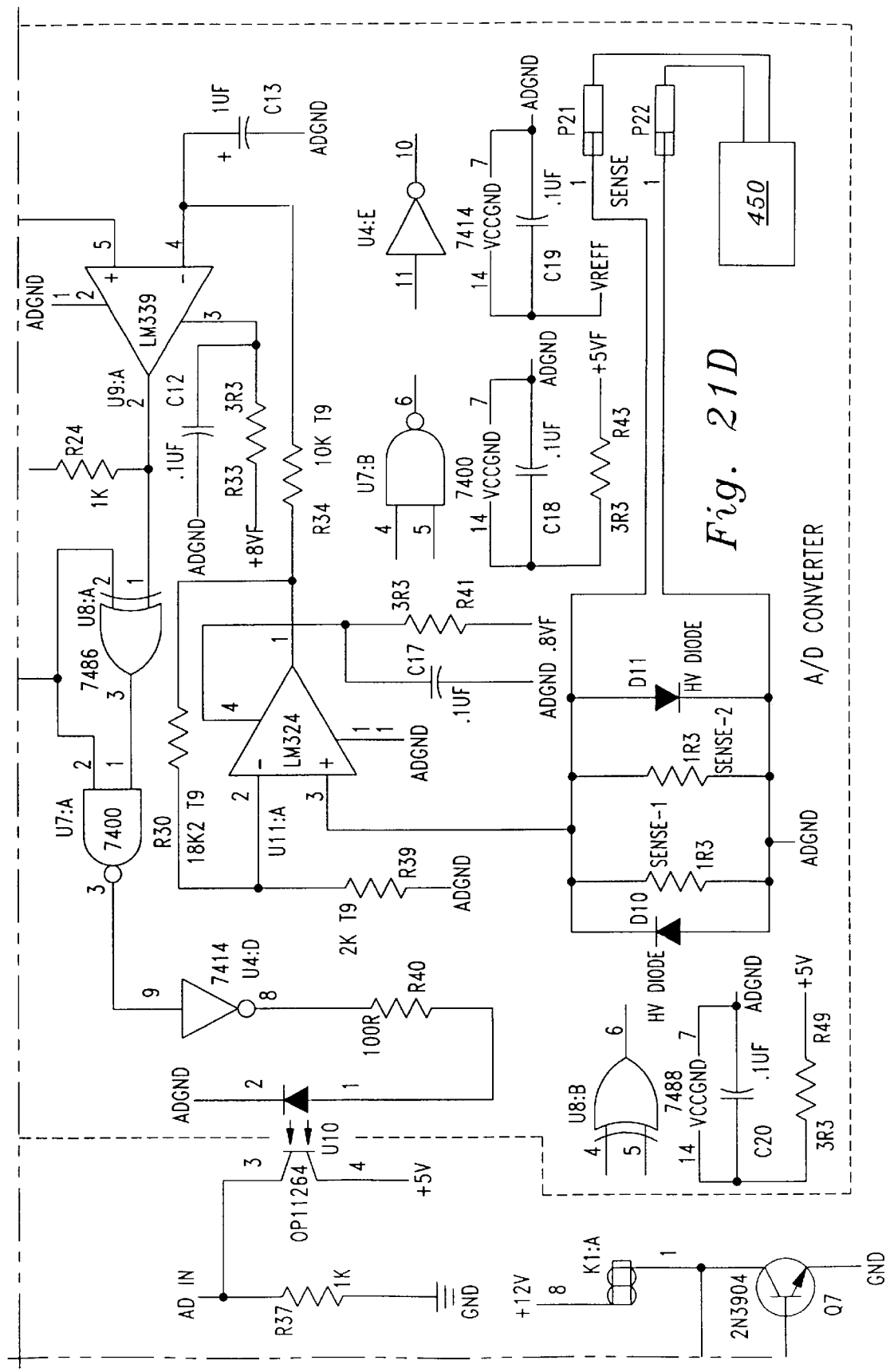

Referring to FIG. 21, a preferred embodiment of the microwave phase controller is designed to drive the microwave chamber. The concept of controlling the average output power of the magnetron with a TRIAC topology is proven. The microwave phase controller design is made up of six building blocks.

System power

Line sync detector

Micro-controller pulse width modulator

Line voltage detection

TRIAC module

Isolated Anode current A/D

Each of the building blocks will be discussed in detail.

System Power:

The system power is supplied by an off the shelf universal switching power supply. The outputs are +5 volts, +12 volts, and −12 volts. Primary is fuse protected.

Line Sync Detector

The 50/60 hz ac input is sampled by a small icon core transformer (T1). Referenced to earth ground, the signal is fed to a comparator (U5). The same signal is also rectified and filtered (D8, C10) to provide a line amplitude "regulated" reference voltage with respect to the input ac amplitude. Pull up resistor (R42) provides the TTL level conversion. The output of the comparator (U5) is a crisp 60 hz square wave. The signal is fed directly into the 16C84 processor (U13), it is also sent to an inverter (U14) to provide the complement for the opposite phase detection. This detection of the line frequency is necessary for TRIAC turn on timing, explained later.

Micro-Controller Pulse Width Modulator

The micro-controller PWM is designed around a PIC 16C84 micro-processor (U13). Phase detection signals arrive at pins 9 and 10, 60 hz square waves 180° out of phase from each other. In software, a delay is created after the rising edge of one of the phase signals is detected (zero crossing point). This process is completed for both the phases in the same manner. The longer the delay value, the less average power delivered to the magnetron. The desired power level, is received via synchronous serial communication, from the digital board micro-processor (Z-180). This power level value is actually sent as desired Anode current A/D counts. The 16C84 matches the power level counts to the Anode current A/D counts received from the isolated A/D circuit, constantly adjusting the delay time from the phase signal zero crossing to when the TRIAC is turned on. This is the topology of regulation.

Line Voltage Detection

Transformer (TI), diode (D8) and capacitor (C10) provide a filtered DC voltage that represents the input line voltage amplitude. An average voltage of about 3vdc is recovered with an input voltage of 115vac, and about 6vdc for an input voltage of 230vac. U5:B and U5:C are comparing a fixed reference voltage to the recovered input line voltage sample. The board can be configured for two different line voltages by selecting jumper "115VAC" or "230VAC". If the sampled line voltage does not match the selected configuration, the 16C84 will not allow the TRIAC to turn on, and the Z-180 receives the error message prompting the user that the configuration is mismatched.

TRIAC Module

The TRIAC module consists of an optical coupler (U2) for isolation and drive of the TRIAC gate. Pin 1 is pulled high with a 330 ohm resistor (R6) only when the SSR "set system run" line is set high by the Z-180. The drive can be aborted if the line voltage status fails by turning on Q1. The TRIAC (Q2) is a 800 volt, 25 amp, isolated case device from Motorola. A 3 square inch heat sink provides moderate thermal dissipation for the device. R2 provides gate current when the opto-coupler turns on. The components that make up the snubber network are R9, R10, R11, C2, C3 and C4. These components provide protection to the TRIAC from voltage spikes generated by the huge inductive load. A series power resistor (0.5 ohm/55 watt) is added between the TRIAC and the Anode high voltage transformer to increase the protection and lower the conducted emissions. The TRIAC power source is independently fused at 10 amps.

The anode current can be used to monitor and the average power the magnetron delivers. For example, the current that the Anode receives flows through the sense resistors "SENSE1, SENSE2". The voltage across the sense resistors represent the Anode current. Should the sense resistors open up, a lethal potential would be present at the isolated A/D circuit. To provide a measure of safety, two high voltage diodes (D10, D11) clamp across the sense resistors to hold the high voltage to a safe level of about +/−2 v. The A/D also is optically isolated by U6 and U10. After the voltage is recovered from the sense resistors, it can be fed to an OP-AMP (U11:A) which can boost the signal to a more workable level. A ramp generator is made up of U4:A,B,C, C11, R14, U11:B and Q4 is the switch. A ramp clock can be provided by the 16C84 (AD-CLK). The voltage reference IC (U3) provides a voltage for U4 so the ramp generator does not drift with temperature. The ramp slope can be compared to the amplified analog voltage at U9:A. The output of the comparator (U9:A) stays high until the ramp slope matches the analog voltage amplitude, then the output switches low. If the analog voltage is low in amplitude, the comparator switches low sooner. If the amplitude is higher, then the comparator switch time is longer. Synchronizing the output of the comparator with the A/D clock takes place at U8:A and U7:A. The output of U7:A is a pulse width modulator that operates at the A/D clock frequency with a pulse width that is proportional to the average current that flows across the sense resistors. In the 16C84 software, an 8 bit timer starts counting at the beginning of the pulse width received, and stops when the pulse goes away.

Figure 24:
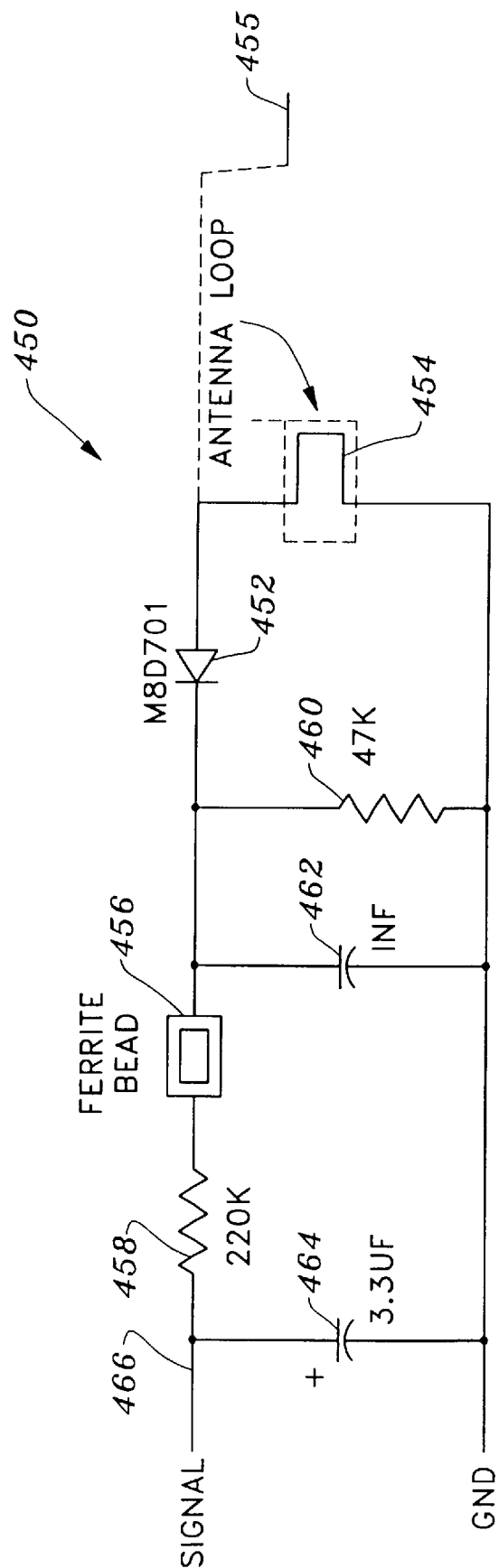
FIG. 24 is a schematic of a microwave energy detector module or magnetic and/or electric field strength detector module according to the instant invention.

Referring to FIGS. 6, 11 and 24, the microwave energy module 450 is operatively disposed within the analysis chamber 260 for controlling, inter alia, the loss on drying process of the sample being assayed and determining when the drying process is complete by sensing microwave energy or magnetic and/or electric field strengths within the chamber 260. Note that a plurality of microwave modules can be deployed to monitor microwave energy within the containment chamber and will operate in the same manner as described hereinbelow with respect to the single microwave energy module 450.

As the sample or load in which the magnetron 170 is delivering power to begins to diminish (i.e., moisture from the sample is being liberated) a field of reflected energy begins to build. Referring to FIG. 24, the microwave energy module 450 is designed to receive this reflected microwave energy and convert the energy into a usable, proportional voltage for regulation purposes. This is accomplished by placing the small loop antenna 454 and/or a pin antenna 455 of the microwave energy module 450 in close proximity with or into at least one of the existing top vent holes 314 disposed in the lid 312 of the chamber 260. The loop antenna senses magnetic fields or H-fields within the analysis chamber 260 and the pin-type antenna senses electric fields or E-fields within the analysis chamber 260.

Note that the microwave energy module 450 operates in a similar manner when either the pin antenna 455 or the loop antenna 454 is employed. Thus, the functionality of the module 450 will be described using the loop antenna with the understanding that the same description applies when the pin antenna is used in place of the loop antenna 454. In addition, both the small loop antenna 454 and the pin antenna 455 can be employed by a pair of microwave energy modules 450 for sensing microwave energy within the chamber 260.

In one embodiment, the small loop antenna 454 of the microwave energy module 450 is placed into one of the existing top vent holes 314 disposed in the lid 312. The loop antenna 454 is connected in a series configuration with a fast schottky barrier diode or UHF detector diode 452 and a ferrite bead 456. The loop antenna 454 senses the microwave energy within the chamber 260 and converts it into a current which is fed to the schottky diode 452. The schottky diode 452 rectifies the current into a voltage which is fed to the ferrite bead 456. The ferrite bead 456 provides fast attenuation of high frequency noise.

More specifically, one end of the loop antenna 454 is connected to an anode of the diode 452 and the other end is connected to ground. The ferrite bead 456 includes a first end connected to a cathode end of the diode 452 and a second end connected to a first end of a resistor 458. The loop antenna 454 and the diode 452 have a resistor 460 and a capacitor 462 coupled in parallel therewith which act as a local filter for the voltage signal. A second capacitor 464 is connected between ground and a second end of the resistor 458. Capacitor 464 and resistor 458 serve to average out and condition an output signal which is taken at an output terminal 466 which is located at the second end of the resistor 458.

The signal output terminal 466 of the module 450 is operatively coupled to the power control board 122 which in turn is coupled to the central processing unit 380. The output signals outputted from the module 450 are analog voltage signals which can be used for regulating the output power of the magnetron 170 as a function of the energy sensed within the containment chamber 260. In addition, the magnetron is completely turned off as a function of the signals received from the microwave energy module 450.

Alternatively, the analog signals outputted from the module 450 can be digitized by the analog to digital converter of the power control board 122 or, in the alternative, by the central processing unit 380. The power control board 122 can use the digitized signals for controlling and regulating the magnetron 170 as a function of the energy sensed within the containment chamber 260. In addition, the power control board 122 can turn off the magnetron as a function of the signals received from the microwave energy module 450. Thus, the power control board 122 can provide full control of the magnetron 170 in direct response to the signal(s) received from the microwave energy module 450 or can do this under the orchestration of the central processing unit 380 processing the signals received from the microwave energy module 450. In other words, the apparatus 10 employs a closed loop system for controlling, inter alia, the loss on drying process of the sample being assayed and determining when the drying process is complete.

Specifically, the power control board 122 provides the input signal for controlling the magnetron. The magnetron 170 outputs energy to the chamber 260 during the drying process. As the sample or load in which the magnetron is delivering power to begins to diminish (i.e., moisture from the sample is being liberated), a field of reflected energy begins to build. The microwave energy module 450 senses this reflected microwave energy and converts the energy into a usable output signal. The output signal is fed to the power control board 122 which in turn feeds a signal to the magnetron 170 for providing a closed loop system and control of the loss on drying process. Thus, the closed loop system allows the output energy of the magnetron 170 to be regulated and turned off in response to the energy sensed in the chamber 260 by the module 450 for providing a superior closed loop loss on drying process. The central processing unit can be employed in this closed loop system by communicating with the power control board 122 as delineated hereinabove.

The central processing unit 380 ultimately collects data from the microwave energy module 450 correlative to the energy in the containment chamber 260 and can use this data for controlling, inter alia, the loss on drying process in a variety of ways which will be delineated infra.

Referring to FIGS. 6, 9 and 11 a sample rotation module 540 or sample rotation means 540 is preferably provided for rotating the carriage 250 during the drying process. Referring to FIGS. 12 and 15, the carriage 250 supports the sample within the chamber 260. The sample is preferably placed between two glass pads 580,582 which are placed on top of the carriage. The carriage is connected to the two piece weighing rod 242 which extends through the bottom of the chamber and then into operable communication with both the electronic balance and the sample rotation module 540. Thus, the two piece weighing rod 242 couples the carriage 250 with the electronic balance for weighing the sample. In addition, the two piece weighing rod operatively couples to the rotation means 450 for rotating the sample.

Referring to FIGS. 9 and 22, the rotation means 450 includes a bearing or a sleeve 546 which is operatively interposed between an upper member 542 of the weighing rod 242 which couples to the carriage 250 and a lower member 544 of the weighing rod 242 which couples to the horizontal lever arm 244. Thus, a motor 554 can be engaged with the upper member 542 of the weighing rod 242 to rotate the carriage 250 during the drying process and disengaged from the upper member 542 when, for example, the sample is being weighed.

More specifically, and referring to FIGS. 9 and 11, the carriage 250 is rotated by motor 554 which includes a shaft 552 having a rubber wheel or gear 550 disposed thereon. The wheel 550 can be brought into communication with the upper member 542 of the weighing rod by engaging the upper member directly or by coupling to a complemental wheel or gear 548 disposed on the upper member 542. Preferably, the shaft 552 of the motor 554 is substantially parallel with the upper member 542 of the weighing rod 242 such that the motor 554 can be disposed on an upper surface 556 of a roller conveyor 558 and translated into and out of engagement with the upper member of the weighing rod by way of a servo-motor 566. The servo-motor 566 employs a crank 562 and a set of rods 560, 564 for translating the roller conveyor 558 into and out of engagement with member 542. Specifically, the conveyor rod 560 is pivotally coupled between the roller conveyor 558 and the crank 562 and the servo-motor rod 564 is pivotal coupled between the crank 562 and the servo-motor 566. Thus, the servo-motor 566 can be driven in a single direction along arrow "A" such that during one-half a revolution of the crank 562 the conveyor rod 560 is pushing the roller conveyor 558 away from the upper member 542 and during a second-half of the revolution of the crank the conveyor rod 560 is pulling the roller conveyor 558 towards the upper member 542 for translating the roller conveyor 558 and motor 566 in a fore and aft direction along double ended arrow "B".

Referring to FIG. 11, the smoke/gas detector module 480 and the flash detector module 510 are operatively disposed within the analysis chamber 260. The smoke/gas detector module 480 provides means for detecting a gas product within the chamber 260. Thus, the smoke/gas detector module 480 provides means for indicating endpoint runover. One detectable gas product takes the form of, for example, carbon dioxide. Therefore, the smoke/gas detector system provides means for detecting burning material, especially of organic origin, which is made visible by the presence of small particles of carbon. The flash detector module 510 provides means for measuring and/or detecting radiant energy particularly in the form of light. Thus, the flash detector module 510 provides us a warning of any ignition within the analysis chamber 260.

Figure 25:
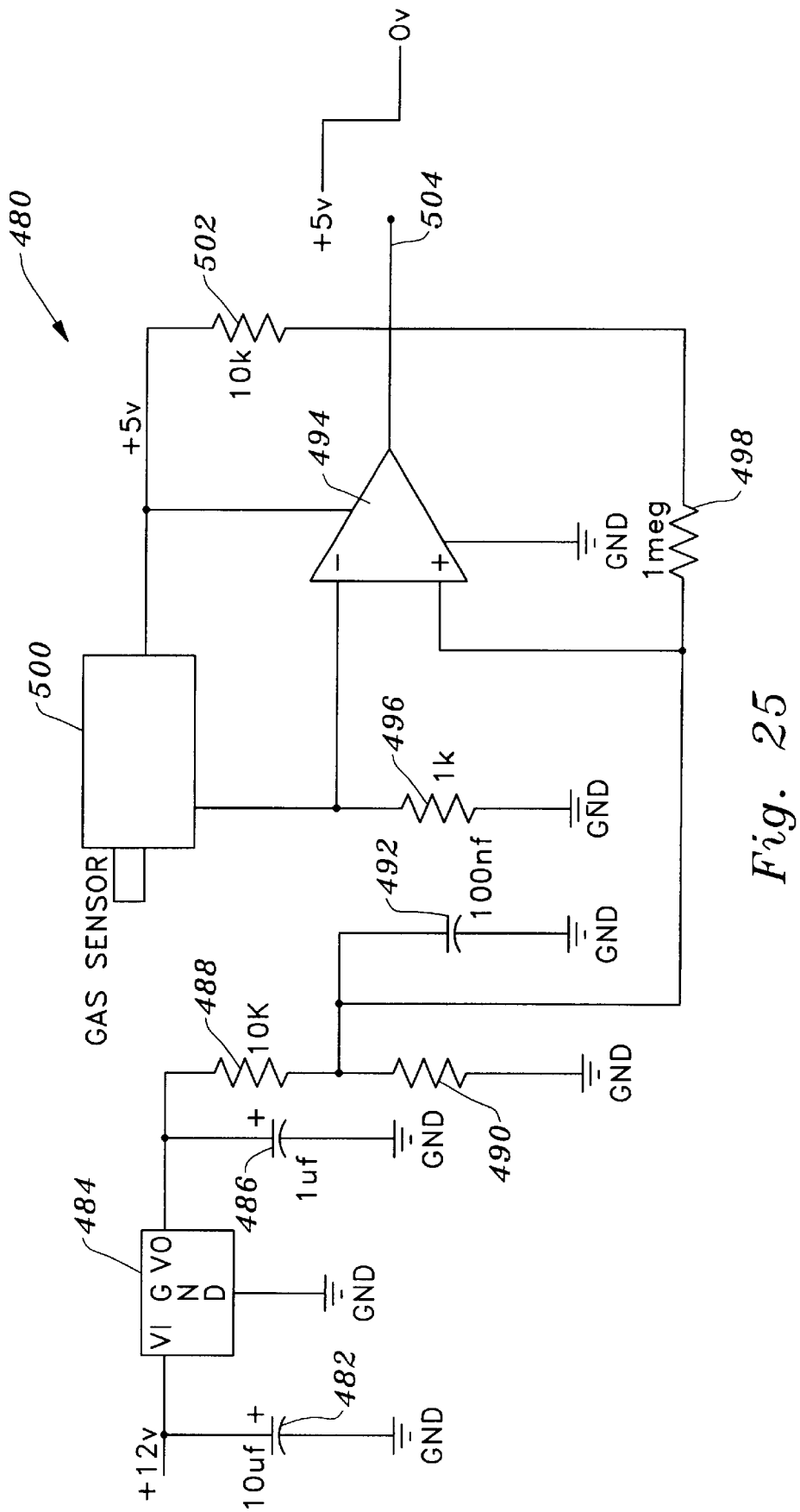
FIG. 25 is a schematic of a smoke/gas detector module according to the instant invention

A circuit schematic of the smoke/gas detector module 480 is shown in FIG. 25. The circuit is designed around a gas detector 500 to detect the gases created when, for example, a sample begins to burn. A positive 12 volt potential is fed into an input of a voltage regulator 484 to provide a stable solid positive 5 volt output used for reference. Capacitors 482 and 486 filter the DC voltage coming into and going out of the voltage regulator 484 respectively. A voltage divider is set up between resistor 488 and a variable resistor 490 to allow adjustability of a threshold point which is fed to a positive input terminal of a comparator 494. Note that capacitor 492 filters the divided voltage. A gas sensor 500 detects gas within the chamber via at least one ventilation hole 314 and applies a voltage at a negative input terminal of the comparator 494 proportional to the level of gas detected. Resistor 496 divides down this amplitude for adjustability. Resistor 498 provides feed back from the output 504 of the comparator 498 to the positive input of the comparator to preclude oscillation. Resistor 502 serves as a pull-up resistor to provide a positive 5 volt TTL logic levels for further circuitry to read. A logic high at the output 504 of the comparator 494 is a normal operating state for the gas detector module 480 while a logic low indicates a predetermined level of gas within the chamber 260. The input of the smoke/gas detector module 480 is preferably coupled to the power control board 122 which provides the positive 12 volt potential fed to the voltage regulator 484. The output of the smoke/gas detector module is coupled to the power control board 122. Thus, when a low is indicated by the output of module 480 the magnetron can be immediately turned off. Thus, the power control board 122 can turn off the magnetron 170 in direct response to the signal(s) received from the smoke/gas detector module 480 or can do this under the orchestration of the central processing unit. In addition, the smoke/gas detector module 480 can be coupled to an alarm which sounded when a logic low is indicated by the output of module 480. Furthermore, the output signals of the smoke/gas detector module 480 can also be fed to the CPU for recording the signals in memory.

Figure 26:
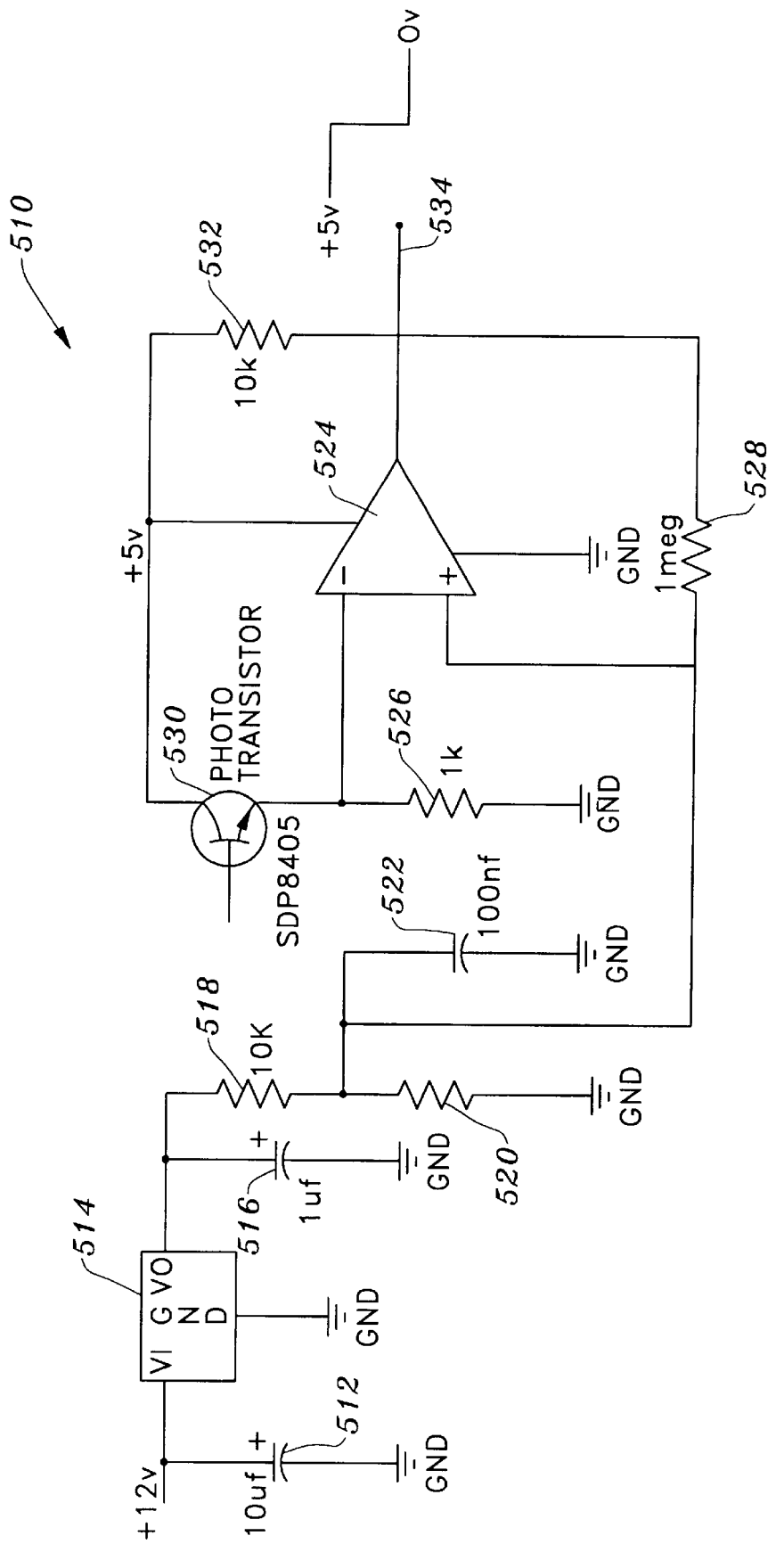
FIG. 26 is a schematic of a flash detector module according to the instant invention.

Referring to FIG. 26, a circuit schematic of the microwave flash detector 510 is shown which detects the presence of light generated when a sample begins to ignite.

The flash detector module 510 includes a regulator 514 having an input which receives a positive 12 volt potential from the power control board 122 and outputs a stable 5 volt potential at an output to be used for reference. Capacitors 512 and 516 filter the DC voltage coming into and going out of the regulator 514. A voltage divider is set up between resistors 518 and 520 to allow adjustability of a threshold point. Capacitor 522 filters the divided voltage. The reference voltage from the voltage divider is fed to a positive input terminal of a voltage comparator 524. A photo transistor 530 applies a voltage at the negative input of the comparator 524 as light excites a base of the photo transistor 530. The base of the photo transistor 530 communicates with the interior of the chamber 260 via at least one vent hole 314. Resistor 526 is used to divide down the amplitude of the output of the transistor 530 for adjustability. A feed back resister 528 precludes oscillation of the circuit. A pull-up resister 532 is used to provide a positive 5 volt TTL logic level for further circuitry to read. Preferably, a logic high at the output 532 is the normal operating state of the flash detector module 510 while a logic low indicates ignition in the chamber 260. When ignition in the chamber 260 is detected the module 510 sends a logic low signal to the power control board 122 to immediately turn off the magnetron 170. Thus, the power control board 122 can turn off the magnetron 170 in direct response to the signal(s) received from the flash detector module 510 or can do this under the orchestration of the central processing unit 380. In addition, the flash detector module 510 can be coupled to an alarm which is sounded when a logic low is indicated by the output of module 510. Furthermore, the output signals of the smoke/gas detector module 480 can collected by the CPU and stored in memory.

In use and operation, and referring to FIGS. 6, 11, 15 and 22, a sample to be assayed is placed between two glass pads 580, 582 which are disposed on the carriage 250. The carriage 250 is operatively coupled to the top loading electronic balance 240 and the rotation means 450 via a two piece weighing rod 242. The initial weight of the sample is determined by the electronic balance 240 and preferably stored in memory means 384 via the CPU 380.

After the initial weight of the sample has been determined the magnetron 170 is energized by the power control board 122. In addition, the rotation means 450 is actuated by the power control board signaling the engage/disengage servo motor 566 to position the rotation motor wheel 550 of the motor 554 into contact with the rod wheel 548 disposed on the rotatable upper member 542 of the weighing rod 242. Both of these actions can be orchestrated by the CPU 380. The same signal that initiates the engage/disengage servo motor 566 also activates the carriage rotation motor 554 thereby rotating motor wheel 550, rod wheel 548, upper member 542, carriage 250, glass pads 580, 582 and the sample which is to be radiated within the microwave chamber 260. Note that the hinged cover or upper chamber 300 must be in a closed position during the drying process and the plurality of micro-switches disable the magnetron 170 should the cover 300 be opened while the apparatus 10 is in operation or if the cover 300 is improperly closed. In addition, fans 328, 330 and 332 preferably provide continuous ventilation of moisture within the chamber 260 during the drying process.

As the sample or load in which the magnetron is delivering power begins to diminish (i.e., moisture from the sample is being liberated), a field of reflected energy begins to build which can be sensed by the microwave energy module 450 and converted into a usable output signal. Thus, microwave energy module 450 can be advantageously employed in a variety of different ways for superior loss on drying (LOD) moisture determination. For example, the microwave energy module 450 can used to monitor the microwave energy within the chamber 260 and control the drying process of the sample to an endpoint as a function of the monitored microwave energy. Once an endpoint has been determined the engage/disengage servo motor 566 receives a signal for disengaging the rotation motor wheel 550 from contact with the rod wheel 548 thereby ceasing carriage rotation. The sample is then reweighed to obtain the final weight and the moisture content is calculated from the stored initial weight and the final weight. The percentage of moisture or volatiles in the sample can be determined by the formula:

$$\% M = ((W_I - W_F)/W_I)(100)$$

where

%M is said percentage of moisture or volatiles in the sample, $W_I$ is said initial weight of the sample, and $W_F$ is said final weight of the sample.

In a further embodiment, the method for loss on drying can include establishing a benchmark correlative to a level of microwave energy sensed by a sensor, employing the sensor to monitor a level of microwave energy within a chamber wherein a sample is being radiated and comparing the monitored energy level with the benchmark level for controlling a drying process of the sample.

Figure 28:
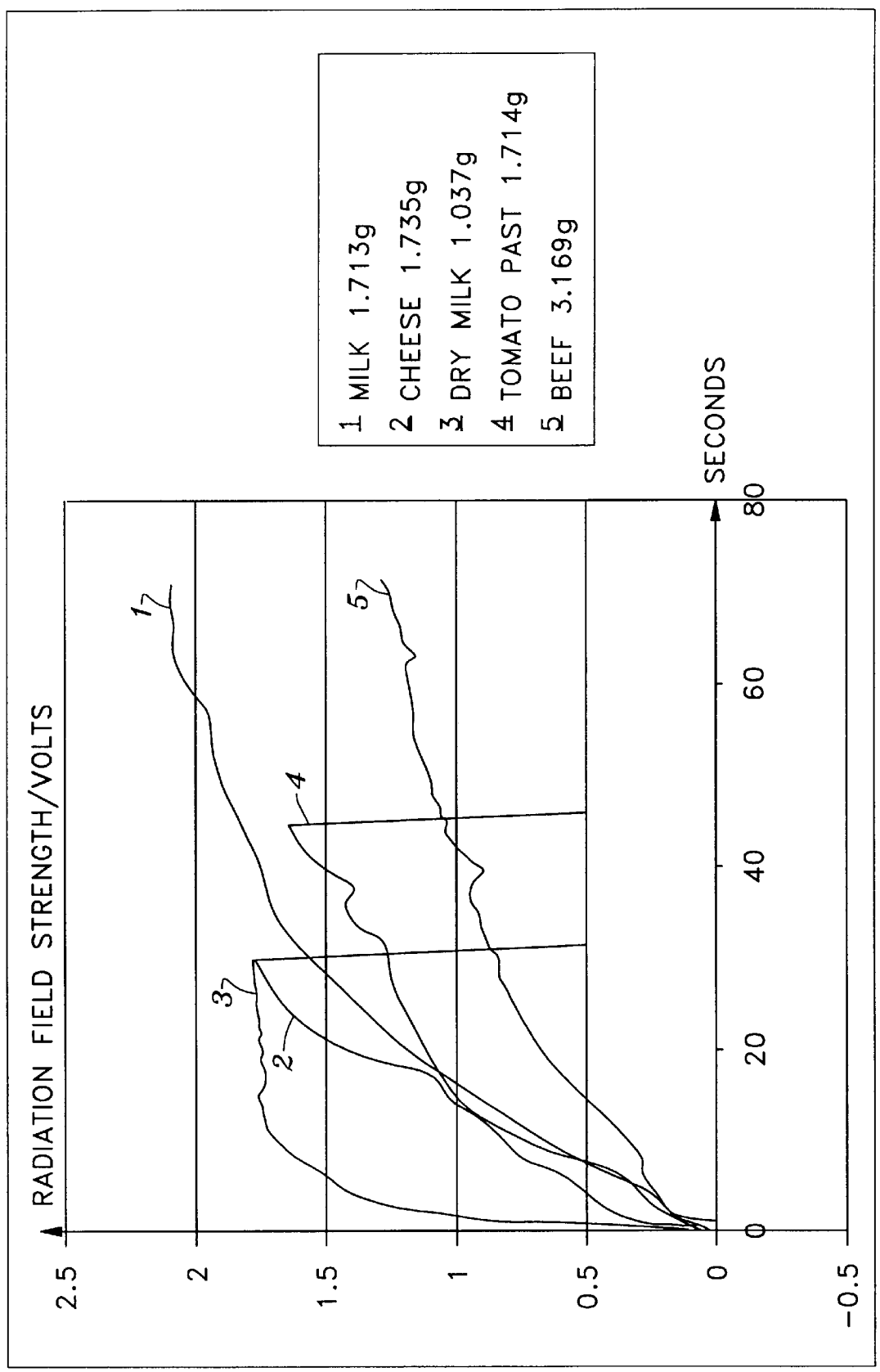
FIG. 28 is a graph of a plurality of field strength/voltage versus time curves of various samples.

For example, the microwave energy module can be used to detect an increase in energy which is unabsorbed by the sample and when this energy increase is at an empirically predetermined level over a period of time, the microwave power can be shut off (please see FIG. 28). Another paradigm includes using the microwave energy module 450 to detect an energy level which corresponds to a point on a energy curve which has a slope which is less than a slope predetermined through experimentation. Once this energy level is detected the microwave energy or magnetron is turned off. Therefore, the module 450 can be used to control the loss on drying process and the moisture content of the sample can be determined by weighing the sample before the process and after the process (i.e., only twice) for obtaining a percentage of moisture or volatiles in the sample.

Another further embodiment of the drying process includes initially weighing the sample being assayed and then rotating the sample while applying constant microwave energy into the analysis chamber 260 containing the sample and waiting for a signal from the microwave energy module 450 to stabilize on a high value (please see FIG. 28). It has been discovered that when the signal does not change, stabilizes on a high value, the load is not changing either (i.e., moisture from the load is not being driven off). Thus, this condition can be used to define an endpoint to the drying process wherein the magnetron is turned off and the rotation of the sample is stopped. The final weight of the sample is then measured and the moisture content calculated.

Figure 27:
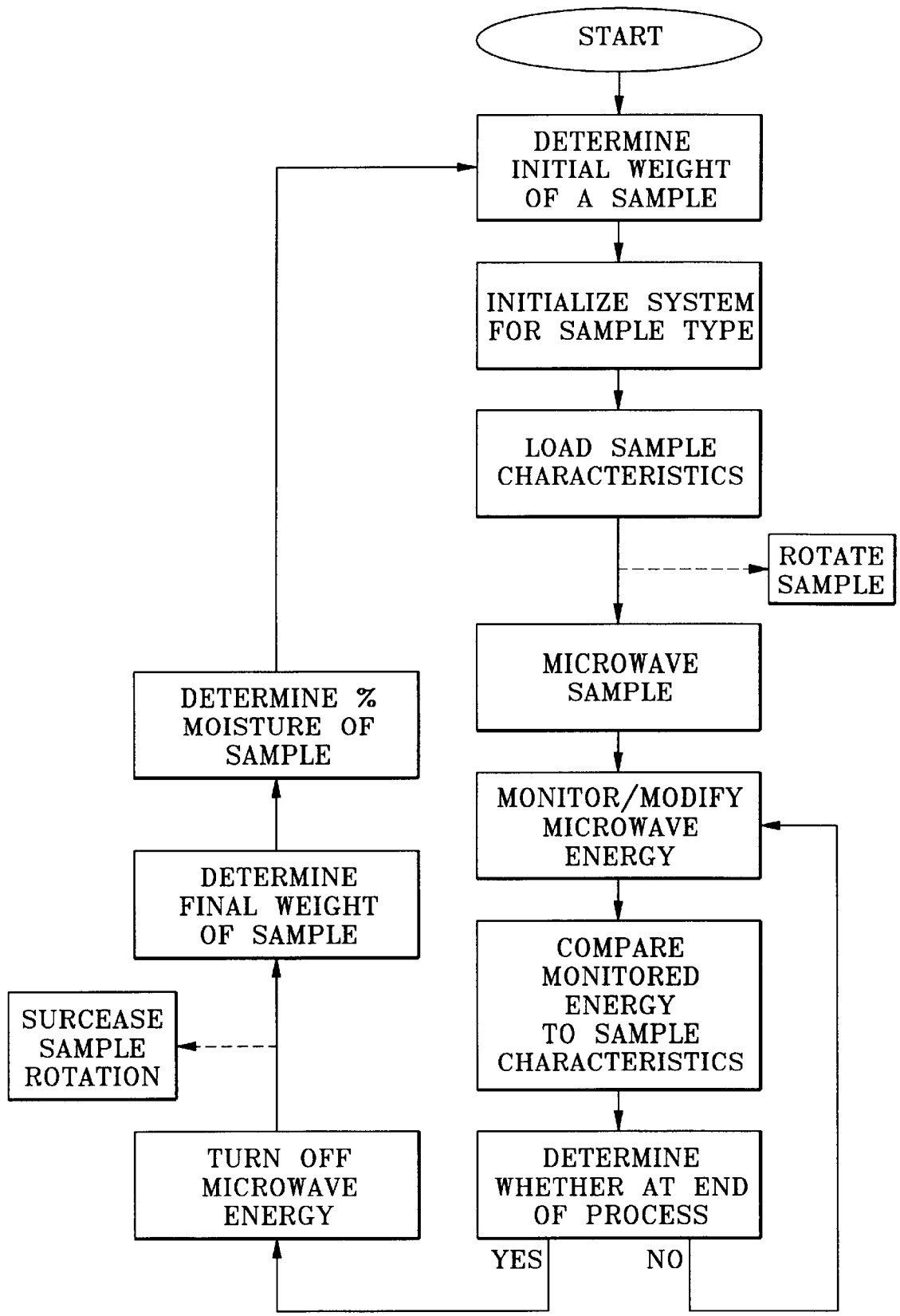
FIG. 27 is a flowchart of a drying process according to one embodiment of the instant invention.

Another further embodiment of the drying process includes the drying process being controlled by modifying the amount of microwave energy delivered to the chamber as a function of the monitored energy until the endpoint is reached (please see FIG. 27). After the endpoint is reached the engage/disengage servo motor 566 receives a signal for disengaging the rotation motor wheel 550 from contact with the rod wheel 548 thereby ceasing carriage rotation. The sample is then reweighed to obtain the final weight and the moisture content is calculated from the stored initial weight and the final weight.

Specifically, the output signal from microwave energy module 450 can be used for regulating the amount of microwave energy applied to the analysis chamber 260. Specifically, the sample can be placed between two glass pads and then located on the carriage 250 operatively disposed within the analysis chamber 260. The carriage 250 is operatively coupled to the top loading electronic balance 240 and the rotation means 450 via the two piece weighing rod 242. Thus, the balance can be used to determine the initial weight of the sample by being calibrated to take into account the weight of the glass pads. Once the initial weight of the sample is discerned the magnetron 170 can be turned on to apply microwave energy through the wave guide into the analysis chamber 260 and the sample can be rotated as delineated hereinabove. The microwave energy module 450 senses the energy within the chamber 260 and outputs a signal correlative thereto. This signal is then compared to one or more predetermined signal levels stored in the central processing unit 380 and/or memory. The central processing unit then communicates with the power control board 122 for regulating the amount of applied microwave energy from the magnetron 170 to the containment chamber 260 as a function of the comparison step thereby controlling the drying process of the sample. Once the central processing unit 380 receives a signal from the microwave energy module 450 which is correlative to an endpoint condition the central processing unit 380 signal control the power control board 122 to turn the magnetron 170 off and stop the rotation of the sample. The balance can then be used to determine the final weight of the sample and the moisture content can be calculated by the central processing unit 380 and then displayed via display 70.

Figure 30:
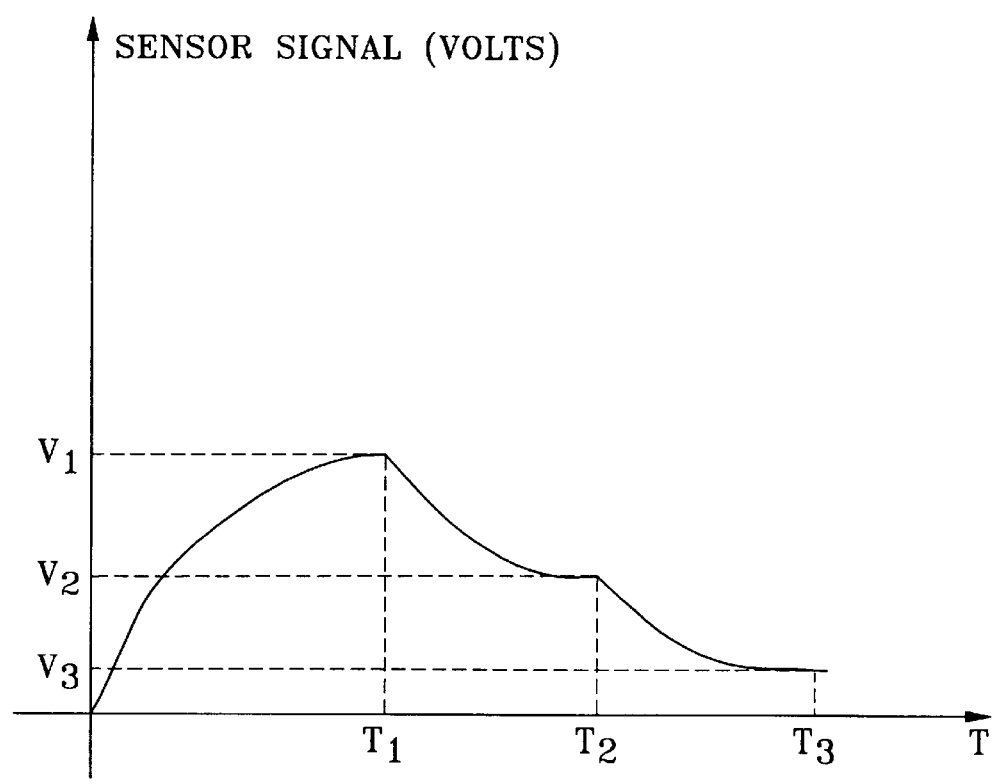
FIG. 30 is a characteristic graph showing sensor signal strength versus time when an applied microwave energy is regulated over subsequent periods of time.

More specifically, the initial weight of the sample can be determined and then a predetermined level of microwave energy can be applied to the sample within the chamber 260 as the sample is rotated. Next, a first interval of time between the initial application of microwave energy and when an outputted signal correlative to the sensed energy is at a first predetermined level of signal strength can be measured. Once this time is discerned the applied microwave energy can be regulated in such a way that the sensed signal correlative to the applied microwave energy is ramped down to subsequently decreasing ratios of the first predetermined signal level over subsequent intervals of time which are each a multiple of the first interval of time (please see FIG. 30). For example, the initial weight of the sample can be determined and then a predetermined level of microwave energy can be applied to the sample within the chamber 260 as the sample is rotated. Next, the time it takes the microwave energy module 450 to sense a predetermined level of signal strength can be measured. Once this time is discerned the applied microwave energy can be regulated in such a way that the signal correlative to the applied energy will ramp down to one-half of the predetermined signal level for an additional time T2 which is equal to the previously measured time T1. Subsequently, the microwave power can be regulated in such a way that the sensor signal will ramp down to one-fourth of the predetermined signal level for an additional time T3 which is a multiple of T1. Once this is completed the final weight of the sample can be determined and the loss on drying moisture content can be calculated.

Another further embodiment of the method for loss on drying can include the step of using a test sample for establishing an algorithm correlative to a change in radiation as function of the test sample and the algorithm including a benchmark correlative to an endpoint condition. Next, determine an initial weight of a subsequent sample before it is radiated. The subsequent sample is then radiated within the chamber and the radiation, correlative to an absorbability of the subsequent sample, is sensed by module 450 and compared to the algorithm for determining when a benchmark correlative to an endpoint condition is detected for signaling the magnetron to be turned off. The final weight of the sample is then determined and the moisture content calculated. Preferably, the subsequent sample is rotated while being radiated as described supra.

Another further embodiment of the method for loss on drying can include establishing a characteristic radiation curve of a sample type correlative of its radiation absorbability, radiating a sample contained within a chamber and comparing subsequently sensed levels of radiation within the chamber with the characteristic curve for determining an endpoint condition.

Figure 29:
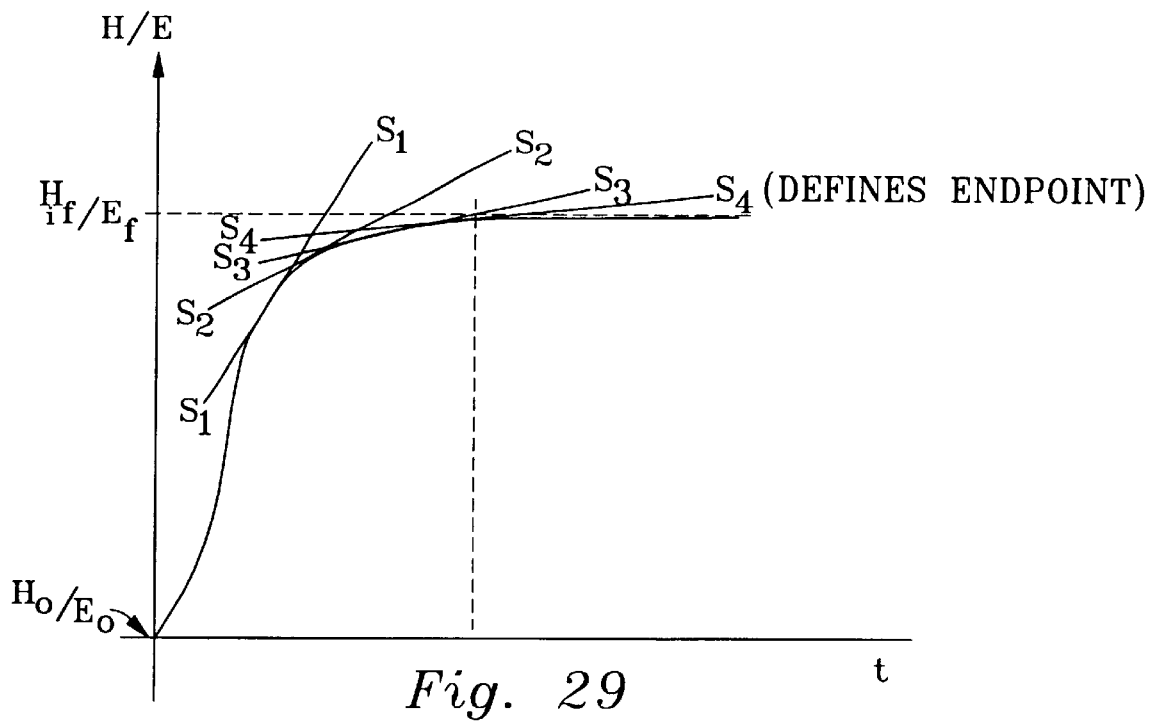
FIG. 29 is a graph of a characteristic field strength versus time curve with slope transitions shown for defining an endpoint according to one embodiment of the instant invention.

Another further embodiment of the method for loss on drying can include establishing a characteristic radiation curve of a sample type correlative of its radiation absorbability. Then, radiating a specimen of the sample type and developing a specimen radiation curve by monitoring a change in radiation correlative to radiation absorbability of the specimen. A transition of slope on the characteristic radiation curve is then compared with a transition of slope on the specimen radiation curve while continuing to radiate the specimen until a predetermined endpoint condition has been detected based on the comparison step (please see FIG. 29).

Once all of the moisture has been exhausted from the sample, it is possible to start extracting additional substances other then water should the power continued to be applied without a endpoint determination being seen. This of course alters the mass which introduces an error in the final moisture calculation. The instant invention solves this problem by providing the smoke/gas detector module 480 which detects the gases created when a sample begins to burn. The input of the smoke/gas detector module 480 is preferably coupled to the power control board which provides power thereto and the output of the smoke/gas is fed to the power control board 122 for providing closed loop control. Thus, when a low is indicated by the output of module 480 the magnetron is turned off. Specifically, the power control board provides the input signal for controlling the magnetron. The magnetron outputs energy to the chamber and if smoke/gas is detected by the smoke/gas detector module 480 a signal is fed back to the power control board for providing a closed loop system which controls the magnetron In addition to the gas detector module 480 described hereinabove, a microwave flash detector module 510 is provided for detecting the presence of light generated when a sample begins to ignite and signaling the power control board 122 to immediately disassociate the magnetron from delivering microwave power to the chamber 260. Although the possibility of a sample igniting in the chamber 260 while doing a loss on drying process is low, it does exist.

The input of the flash detector module 510 is preferably coupled to the power control board which provides power thereto and the output of the flash detector module 510 is fed to the power control board 122 for providing closed loop control. Specifically, the power control board provides the input signal for controlling the magnetron. The magnetron outputs energy to the chamber and if the presence of light is detected by the flash detector module 510 a signal is fed back to the power control board for providing a closed loop system which controls the magnetron.

The microwave moisture analyzer is a state of the art microprocessor based moisture/solids analyzer 10 which uses the principles of loss on drying (LOD) analysis. Samples are heated using microwave energy to liberate moisture or other volatiles until end point conditions are met. When the analyzer is turned on by placing the on/off switch on the back of the analyzer into the on position, the analyzer will proceed through a self diagnostic routine and then display a stand-by screen on preferably a backlit liquid crystal display 70. Preferably, the liquid crystal display 70 is a dot addressable device which allows the analyzer to convey a rich variety of detailed information in plain English descriptive prompts, menus, or help messages. The set-up of the microwave moisture analyzer is accomplished by merely selecting the appropriate routine from the menu driven software displayed on the LCD display 70. Drying parameters are easily entered through the soft keys 72, 74, 76, 78 or the numeric keypad either by touching the corresponding number or entering the exact value with the numeric keys. Preferably, the LCD display 70 will conveniently illustrate all of the drying parameters including units, temperatures and end point selections. The memory associated with the central processing unit can be used to store drying procedures with meaningful alpha-numeric program names while the recall routine allows easy selection. The simplicity of the soft keys and the numeric keypads and the display prompts make routine operations near-effortless. The microwave moisture analyzer automatically calculates and documents results on its internal printer. Preferably, a choice of printouts provide either a simple result or a format including selection of operator name, analyzer I.D., program name and drying parameters, and for true customization, a multi-line header. As mentioned, the microwave moisture analyzer features data storage and in addition has the ability to provide statistical evaluations of selected data.

More specifically, when the on/off switch on the back of the analyzer is placed into the on position the analyzer proceeds through a self diagnostic routine and then displays a stand-by screen to the user via the LCD display. A title line on the top of the stand-by screen identifies the specific screen displayed along with date and time. In addition, the bottom of the stand-by screen identifies four different options which may be selected via the associated soft keys disposed below each respective option. These options include a recall option, a set-up option, a data option and a paper feed option. When the soft key correlative to the set-up option is pressed a set-up screen will be displayed on the LCD which preferably includes seven menu driven choices. These seven menu driven choices can be either initiated via the numeric keypad or by using the directional arrow keys to scroll up and down the menu and then hitting the enter key to select the highlighted option. These seven options include a beeper option, a develop option, a security option, a calibrate option, a print-out option, a clock option and an output option. The bottom of the screen of the set-up display provides the user with an exit choice or a help choice which can be initiated by pressing the correlative soft key located directly there beneath. The beeper option allows the user to turn on or off a sound annunciation when either a key is pressed or when an end of test is discerned by the analyzer. The beeper screen incorporates a stand-by option displayed in the lower menu and can be used to go back to the stand-by screen by pressing the soft key associated therewith.

The second option of the set-up screen is preferably the develop option wherein drying procedures can be developed by optimizing the drying parameters for specific applications. Specifically, when the develop option is chosen a develop screen will be displayed with a plurality of selections to choice from. The selections may include units, power one, time one, power two, time two, slope, target and mode choices. Any one of these options may be initiated by either pressing the corresponding numeral on the numeric keypad which correlates to the option or by using the direction keys to scroll through the options and then hitting the enter key when the option which is desired is highlighted on the LCD screen display. The units option allows the user to select or change the units of measure depending on a specific application. Thus, when the units option is selected the display will change to the list of units available to the user which preferably includes five choices: a moisture choice, a solids choice, a volatiles choice and a MG/L choice. After a unit has been selected the display will return to the develop screen showing the new unit selected.

The power one option allows the user to set the power level to be used during a first time period. When the power one option is selected from the develop screen a power one screen will be displayed allowing the user to chose a power level between the range one to one hundred percent of the rated power output to the microwave containment chamber. Once the power is selected the analyzer will once again display the develop screen to allow the user to make a subsequent choice if the time in which the magnetron will be driven to provide the power one option is chosen by selecting the time one option of the development screen. This option provides a pop-up menu which allows the user to select a range of time of preferably between 0.1 minute and sixty minutes. A second power level may be chosen when using a two-step drying method. The second power level works identically to the first power level wherein the power level is selected by the user via a pop-up menu. Likewise, a time two option of the development screen allows the time at which the second power level will be driven to by chosen by the user as has been delineated for the time one option.

The next option on the develop screen is an endpoint option. In one embodiment, the endpoint option is a function which allows the user to select an algorithm based on the sample being assayed which provides an automatic endpoint to the test. The endpoint function is preferably based on an established algorithm correlative to a change in radiation within the chamber as a function of sample absorbability.

In another embodiment, the endpoint option is a function which allows the user to select or define a signal level in which the output of module 450 is compared to and which also allows the user to select or define how the applied microwave energy is regulated as a function of the comparison step for providing an automatic endpoint to the test.

In a further embodiment, the endpoint option is a function which allows the user to select a characteristic radiation curve of a sample type correlative of its radiation absorbability and then comparing subsequently sensed levels of radiation curve as monitored by the module 450 for providing an automatic endpoint to the test.

In a further embodiment, the endpoint option is a function which allows the user to select a transition of slope or an inflection of slope of the sensed radiation as monitored by the module 450 for providing an automatic endpoint to the test.

In each case the initial weight of the sample is determined prior to the sample being radiated and the final weight of the sample is determined after the endpoint condition is meet. The moisture content of the sample is then calculated.

The user may return to the develop screen by simply pressing the enter key after suing the slope option or by simply turning off the slope completely.

The next option of is a target option wherein the user can enter a target initial weight preferably in grams within a range of zero point one to thirty grams and then press the enter key to set the parameters.

The last option of the develop screen is a mode option wherein the user may select between a standard mode, a MG/L mode, a pre-dried pad mode or a syringe mode. Once the user has completed his development of the sample to be assayed he may simply use the save option displayed on the soft key menu by pressing the associated soft key. Once the save option has been initiated the user is allowed to select a location to store the develop program as a program number, for example one through ninety-nine. In addition, the user may specifically name the program via a pop-up program name showing the alphabet and various characters. The user uses the direction arrow keys to highlight the character on the pop-up menu and then presses and enter key to spell out the name of the program, this name is then saved using the soft menu save option. When the user has completed these functions the software will revert back to the standby screen wherein the soft menu includes a recall option, a set-up option, a data option and a paper feed option which may be initiated by activating any one of the soft keys associated therewith.

The set-up option includes a security option wherein the user can set up a security routine for precluding unauthorized personnel from using the analyzer. For example, the user can set up a specific password which must be entered prior to the analyzer being activated. This is done in the same manner as naming a program. In addition, the security menu includes option where programs can be cleared, data can be cleared, system information can be provided and programs can be alphabetized.

The set-up option also includes a calibration option wherein the precision balance can be calibrated. For example, once the calibrate option is displayed the user can place a predetermined amount of weight on the balance when prompted by the display and the analyzer will automatically recognize the weight and adjust the weight display to correspond thereto. For example, a fifty gram weight can be placed on the sample carriage when prompted by the display and will result in display a "calibration done" output on the LCD when the calibration has been successful.

The following outlines the typical steps used in developing an optimized drying procedure which is accurate and reproducible for a given type sample with typical range of moisture and a desired sample size. In general, a standard convection oven method is used as a reference method to determine the accuracy of the microwave analyzer method. Sequentially, various parameters of the drying procedure will be modified based on experiment test data from actual sample testing with the goal of meeting specific methods development objectives including accuracy, precision and analysis time.

First, a development sample is chosen which is representative of the sample requiring a moisture test method using the analyzer. This is a typical sample with a known moisture value as tested by the reference method which is chosen to do most of the methods development. The method should then be verified and modified based on a larger sample set with varying moisture levels across the typical moisture range to improve the method robustness.

Development Steps:
1) Sample preparation
2) Selecting the presentation technique of one or two glass pads
3) Optimizing sample size and weight
4) Selecting the optimum endpoint according to microwave energy field
5) Optimizing the drying power level for minimum analysis time
6) Developing a two step drying procedure Typically the sample will be prepared identically to that of the reference method to obtain good sample representation. Select one or two glass pads based on the sample consistency. Liquid samples will typically be dispensed onto a single pad, whereas samples of a paste consistency will be sandwiched between two pads. Start the drying procedure development by using the default drying conditions to test the development sample using a 2–5 g sample size using the determined presentation technique. Several replicates should be tested noting moisture recovery as compared to the known moisture value, reproducibility of test results, analysis time and sample appearance after testing.

A change to a larger sample size should be considered if the sample is heterogeneous and great representation is necessary to achieve better reproducibility. A change to a smaller sample size should be considered to reduce the analysis time.

A change to a lower power level should be considered if the sample after testing appears scrorched or a higher recovery than expected occurs. A change to a higher power level should be considered to reduce the analysis time. In some cases it may be advantageous to develop a two step drying procedure where the power level can be reduced to a lower level after the set corresponding period of Time 1.

Moreover, having thus described the invention, it should be apparent that numerous structural modifications and adaptations may be resorted to without departing from the scope and fair meaning of the instant invention as set forth hereinabove and as described hereinbelow by the claims. For example, an embodiment is contemplated once having had the benefit of the foregoing teachings, wherein a method for loss on drying includes the steps of placing a sample in a microwave, powering the microwave to dry the sample, monitoring and/or sensing the microwave energy within the microwave and weighing the sample either continuously or intermittently (e.g. at sensed endpoints) while powering the microwave. Alternatively, an embodiment is envisioned wherein a method for loss on drying may include the steps of placing a sample in a microwave and powering the microwave to dry the sample for an initial period of time and then intermittently or continuously weighing the sample while monitoring and/or sensing the microwave energy after the initial time to an endpoint condition. Therefore, the spirit and scope of the appended claims should not be limited to the description as set forth hereinabove.

We claim:

1. A loss on drying apparatus in which a sample is dried to determining its moisture content, comprising in combination:

a microwave chamber having an area to receive the sample;

a microwave energy source operatively coupled to said chamber for delivering microwave energy thereto for drying the sample therein;

at least one microwave energy sensor operatively disposed within said microwave chamber for monitoring changes in the sample's ability to lose moisture by measuring changes in microwave energy within said microwave chamber.

2. The apparatus of claim 1 further including weighing means operatively disposed within said microwave chamber.

3. The apparatus of claim 2 wherein said weighing means is used before a drying process to determine an initial weight of the sample.

4. The apparatus of claim 3 wherein said energy sensor monitors microwave energy within said microwave chamber for controlling said drying process of the sample contained within said microwave chamber.

5. The apparatus of claim 4 wherein said weighing means is used after said drying process to determine a final weight of the sample.

6. The apparatus of claim 5 further including means for determining a percentage of substances susceptible to evaporation in the sample.

7. The apparatus of claim 6 wherein said percentage of substances susceptible to evaporation in the sample is determined by the formula:

$$\% M = ((W_I - W_F)/W_I)(100)$$

where
 $\% M$ is said percentage of moisture in the sample,
 $W_I$ is said initial weight of the sample, and
 $W_F$ is said final weight of the sample.

8. The apparatus of claim 1 wherein said energy sensor is operatively coupled to said microwave energy source for controlling the delivery of microwave energy to said microwave chamber correlative to energy sensed by said sensor thereby controlling a drying process of said sample.

9. The apparatus of claim 8 wherein said energy sensor monitors microwave energy within said microwave chamber for determining when said drying process of the sample is complete.

10. The apparatus of claim 9 wherein said energy sensor is operatively coupled to said microwave energy source for turning said microwave energy source off when said energy sensor determines that said drying process of the sample is complete.

11. The apparatus of claim 1 wherein said microwave chamber is cylindrical in shape.

12. The apparatus of claim 11 including tuning rods disposed in said cylindrical microwave chamber.

13. The apparatus of claim 12 including first and second magnetic modes of microwave energy within said cylindrical microwave chamber, said first and second magnetic modes of microwave energy oriented transverse with respect to one another.

14. The apparatus of claim 13 including means for loading a sample from a top of said microwave chamber.

15. The apparatus of claim 14 including an attenuating stub in a microwave waveguide coupling said microwave energy source to said microwave chamber.

16. The apparatus of claim 15 including glass pads located in said microwave chamber to receive a sample to be dried.

17. The apparatus of claim 1 wherein said energy sensor senses microwave energy previously allocated to drying the sample.

18. The apparatus of claim 1 wherein said energy sensor is operatively coupled to said microwave energy source for turning said microwave energy source off when said energy sensor detects a predetermined energy level within said microwave chamber.

19. The apparatus of claim 1 wherein said energy sensor is operatively coupled to said microwave energy source for turning said microwave energy source off when at least one said energy sensor detects an energy increase level having a slope which is less than a certain predetermined slope of an energy curve.

20. The apparatus of claim 1 further including means for detecting radiant energy within said microwave chamber.

21. The apparatus of claim 20 wherein said means for detecting radiant energy includes means for detecting radiant energy in the form of light.

22. The apparatus of claim 1 further including means for detecting a gas within said microwave chamber.

23. A method determining the amount of liquid lost on drying of a specimen from which liquid is released, the steps including:
 placing the specimen to be dried in a cylinder microwave chamber;
 determining the specimen's weight;
 delivering microwave energy to the cylinder microwave chamber;
 monitoring changes of the microwave energy within the cylinder microwave chamber which correlates with liquid lost;
 controlling a drying process of the specimen as a function of the changes of the monitored microwave energy by altering the delivery of microwave energy to the cylinder microwave chamber; and
 determining the specimen's final weight after driving off the liquid.

24. The method of claim 23 further including the step of venting moisture from the microwave continuously during the drying process.

25. The method of claim 24 wherein the step of delivering microwave energy includes delivering first and second magnetic modes of microwave energy, one oriented transverse with respect to the other.

26. A method for loss on drying, the steps including:
 placing a specimen in a cylinder microwave chamber;
 delivering microwave energy to the cylinder microwave chamber;
 monitoring the microwave energy within the cylinder microwave chamber;
 controlling a drying process of the specimen as a function of the changes of the monitored microwave energy;
 venting moisture from the microwave continuously during the drying process;
 wherein the step of delivering microwave energy includes delivering first and second magnetic modes of microwave energy, one oriented transverse with respect to the other; and
 including the step of providing a first and a second tuning rod within the cylinder microwave chamber to promote a resonance condition and stirring of the microwave energy within the cylindrical microwave.

27. The method of claim 26 wherein monitoring the microwave energy includes sensing microwave energy previously allocated to drying the sample wherein the sensed microwave energy is correlative to the energy unabsorbed by the sample.

28. The method of claim 27 further including the step of surceasing the delivery of microwave energy to the cylinder microwave chamber when at least one microwave energy sensor detects an energy increase.

29. A method for loss on drying in which liquid in a sample is quantified by its removal, the steps including:
 placing the sample in a chamber;

weighing the sample to obtain an initial weight thereof;

applying microwave energy to a chamber containing the sample;

sensing changes in the microwave energy within the chamber for controlling a drying process of the sample to an endpoint at which negligible liquid remains by modifying the amount of applied microwave energy during the course of drying as a function of measured changes in the microwave energy being applied;

ceasing the microwave energy when the measured changes of the energy indicates a dry condition;

reweighing the sample at an end of the drying process to obtain a final weight thereof correlative of the amount of liquid surrendered during drying.

30. The method of claim 29 further including the step of determining a moisture content of the sample from the initial and final weights.

31. A method for loss on drying in which liquid is removed from a sample to dryness, the steps including:

applying microwave energy to the sample having a known weight and contained with in a chamber;

sensing the energy within the chamber and outputting a signal correlative to the sensed energy;

comparing the outputted signal to a predetermined signal level correlative to a dried sample surrendered;

regulating the amount of microwave energy applied as a function of the last name comparing until drying the sample has been completed.

32. The method of claim 31 further including the step of measuring a first interval of time between an initial application of microwave energy and when an outputted signal correlative to the sensed energy is at a first predetermined signal level.

33. A method for loss on drying, the steps including:

applying microwave energy to a sample having a known weight and contained with in a chamber;

sensing the energy within the chamber and outputting a signal correlative to the sensed energy;

comparing the outputted signal to a predetermined signal level;

regulating the applied microwave energy as a function of the last name comparing for drying the sample; and further including the step of measuring a first interval of time between an initial application of microwave energy and when an outputted signal correlative to the sensed energy is at a first predetermined signal level;

wherein the step of regulating the applied microwave energy includes ramping down the applied energy to a ratio of the first predetermined signal level.

34. The method of claim 33 including ramping down the applied energy over an interval of time substantially equal to the measured first interval of time.

35. A method for loss on drying, the steps including:

applying microwave energy to the sample having a known weight and contained with in a chamber;

sensing the energy within the chamber and outputting a signal correlative to the sensed energy;

comparing the outputted signal to a predetermined signal level;

regulating the applied microwave energy as a function of the last name comparing for drying the sample; and further including the step of measuring a first interval of time between an initial application of microwave energy and when an outputted signal correlative to the sensed energy is at a first predetermined signal level;

wherein the step of regulating the applied microwave energy includes ramping down the applied energy to a ratio of the first predetermined signal level over an interval which is a multiple of the measured first interval of time.

36. A method for loss on drying, the steps including:

applying microwave energy to the sample having a known weight and contained with in a chamber;

sensing the energy within the chamber and outputting a signal correlative to the sensed energy;

comparing the outputted signal to a predetermined signal level;

regulating the applied microwave energy as a function of the last name comparing for drying the sample; and further including the step of measuring a first interval of time between an initial application of microwave energy and when an outputted signal correlative to the sensed energy is at a first predetermined signal level;

wherein the step of regulating the applied microwave energy includes ramping down the applied energy to subsequently decreasing ratios of the first predetermined signal level over subsequent intervals of time which are each a multiple of the first interval of time.

37. A loss on drying apparatus, comprising in combination:

a microwave chamber having a circular bottom wall, and a cylindrical sidewall for receiving a sample;

a microwave energy source operatively coupled to said chamber for delivering microwave energy thereto for drying the sample therein;

at least one microwave energy sensor operatively disposed within said microwave chamber for sensing the amount of microwave energy which is not being absorbed by the sample, which is correlative of the sample's progressive drying, and means for rotating the sample within the microwave chamber during drying.

38. A method for loss on drying in which liquid is driven from a sample, the steps including:

placing the sample in an interior of a microwave;

delivering microwave energy to an interior of the microwave;

monitoring changes in the level of the microwave energy within the microwave;

rotating the sample within the microwave, and controlling the rate of drying of the sample as a function of the monitored microwave energy by altering the microwave energy delivered to the interior of the microwave.

39. A method for loss on drying in which liquid is released, the steps including:

placing a specimen to be dried in a microwave chamber;

delivering microwave energy to the microwave chamber;

monitoring changes of the microwave energy within the microwave chamber;

controlling a drying process of the specimen as a function of the changes of the monitored microwave energy by altering the delivery of microwave energy to the microwave chamber;

providing a first and a second tuning rod within the microwave chamber to promote a resonance condition and stirring of the microwave energy within the microwave chamber.

40. A method for loss on drying in which liquid is released, the steps including:

placing a specimen to be dried in a microwave chamber;

delivering microwave energy to the microwave chamber;

monitoring changes of the microwave energy within the microwave chamber;

controlling a drying process of the specimen as a function of the changes of the monitored microwave energy by altering the delivery of microwave energy to the microwave chamber;

wherein monitoring the microwave energy includes sensing microwave energy previously allocated to drying the sample wherein the sensed microwave energy is correlative to the energy unabsorbed by the sample.

41. A method for loss on drying in which liquid is released, the steps including:

placing a specimen to be dried in a microwave chamber;

delivering microwave energy to the microwave chamber;

monitoring changes of the microwave energy within the microwave chamber;

controlling a drying process of the specimen as a function of the changes of the monitored microwave energy by altering the delivery of microwave energy to the microwave chamber;

surceasing the delivery of microwave energy to the microwave chamber when at least one microwave energy sensor detects an energy increase.

42. A method for loss on drying in which liquid is removed from a sample to dryness, the steps including:

applying microwave energy to the sample having a known weight and contained with in a chamber;

sensing the energy within the chamber and outputting a signal correlative to the sensed energy;

comparing the outputted signal to a predetermined signal level correlative to a dried sample surrendered;

regulating the amount of microwave energy applied as a function of the last name comparing until drying the sample has been completed;

measuring a first interval of time between an initial application of microwave energy and when an outputted signal correlative to the sensed energy is at a first predetermined signal level; and ramping down the applied energy over an interval of time substantially equal to the measured first interval of time.

43. A loss on drying apparatus, comprising in combination:

a microwave chamber;

a microwave energy source operatively coupled to said chamber for delivering microwave energy thereto for drying a sample therein;

at least one microwave energy sensor operatively disposed within said microwave chamber;

wherein said energy sensor senses microwave energy previously allocated to drying the sample.

44. A loss on drying apparatus, comprising in combination:

a microwave chamber;

a microwave energy source operatively coupled to said chamber for delivering microwave energy thereto for drying a sample therein;

at least one microwave energy sensor operatively disposed within said microwave chamber; and detecting radiant energy within said microwave chamber;

wherein said means for detecting radiant energy includes means for detecting radiant energy in the form of light.

* * * * *